US012656349B2

(12) United States Patent
Naora et al.

(10) Patent No.: US 12,656,349 B2
(45) Date of Patent: Jun. 16, 2026

(54) MEASUREMENT OF BEVACIZUMAB-INSENSITIVE VASCULAR ENDOTHELIAL GROWTH FACTOR-A

(71) Applicant: Board of Regents, The University of Texas System, Austin, TX (US)

(72) Inventors: Honami Naora, Houston, TX (US); Song Yi Ko, Houston, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 49 days.

(21) Appl. No.: 17/769,826

(22) PCT Filed: Oct. 16, 2020

(86) PCT No.: PCT/US2020/055922
§ 371 (c)(1),
(2) Date: Apr. 18, 2022

(87) PCT Pub. No.: WO2021/076852
PCT Pub. Date: Apr. 22, 2021

(65) Prior Publication Data
US 2022/0390456 A1 Dec. 8, 2022

Related U.S. Application Data

(60) Provisional application No. 62/916,472, filed on Oct. 17, 2019.

(51) Int. Cl.
*G01N 33/53* (2006.01)
*A61K 45/06* (2006.01)
*C07K 16/22* (2006.01)
*G01N 33/575* (2026.01)
*G01N 33/74* (2006.01)

(52) U.S. Cl.
CPC ....... *G01N 33/57585* (2026.01); *A61K 45/06* (2013.01); *C07K 16/22* (2013.01); *G01N 33/74* (2013.01); *C07K 2317/24* (2013.01); *G01N 2333/475* (2013.01)

(58) Field of Classification Search
None
See application file for complete search history.

(56) References Cited

U.S. PATENT DOCUMENTS

| | | |
|---|---|---|
| 2013/0177554 A1 | 7/2013 | Delmar et al. |
| 2014/0341893 A1 | 11/2014 | Andres et al. |
| 2016/0122426 A1 | 5/2016 | Doh et al. |
| 2017/0184602 A1 | 6/2017 | Martini et al. |
| 2017/0281725 A1 | 10/2017 | Sims et al. |

OTHER PUBLICATIONS

Taraboletti et al. Neoplasia. 8(2): 96-103, 2006.*
Esser, (Esser, P. "The Surface/Volume Ratio in Sold Phase Assays", 2014 [retrieved on Nov. 13, 2024]. Retrieved from: assets. thermoscientific.com>Application-Notes).*

Papadopoulos et al. Angiogenesis 15: 171-185, 2012.*
Patuleia et al. (Cancers, 2022, 14, 159, https://doi.org/10.3390/cancers14010159).*
Hyodo et al. (European Journal of Cancer, 34(13): 2041-2045, 1998).*
Kut et al. (Brit. J. Can. 97: 978-985, 2007).*
Anderson, S. M. et al., "VEGF internalization is not required for VEGFR-2 phosphorylation in bioengineered surfaces with covalently linked VEGF," *Integr. Biol. (Camb)*, 3.9 (2011): 887-896.
Cao, Y. et al., Forty-year journey of angiogenesis translational research, *Sci. Transl. Med.*, 3.114rv3 (2011): 1-19.
Cao, Y, "VEGF-targeted cancer therapeutics-paradoxical effects in endocrine organs," *Nature Reviews Endocrinology*, 10 (2014): 530-539.
Chen, G. et al., "Exosomal PD-L1 contributes to immunosuppression and is associated with anti-PD-1 response," *Nature*, 560.7718 (2018): 382-386.
Eppler, S. M. et al., "A target-mediated model to describe the pharmacokinetics and hemodynamic effects of recombinant human vascular endothelial growth factor in humans," *Clinical Pharmacology & Therapeutics*, 72.1 (2002): 20-32.
Feng, Q. et al., "A class of extracellular vesicles from breast cancer cells activates VEGF receptors and tumour angiogenesis," *Nature Communications*, 8.14450 (2017): 1-17.
Ferrara, N. et al., "The biology of VEGF and its receptors," *Nature Medicine*, 9 (2003): 669-676.
Ferrara, N. et al., Discovery and development of bevacizumab, an anti-VEGF antibody for treating cancer, Nature Reviews Drug Discovery, 3 (2004): 391-400.
Ferrara, N., "Binding to the extracellular matrix and proteolytic processing: two key mechanisms regulating vascular endothelial growth factor action" *Mol. Biol. Cell.* 21.5 (2010): 687-690.
Frentzas, S. et al., "Vessel co-option mediates resistance to anti-angiogenic therapy in liver metastases," *Nat. Med.*, 22 (2016): 1294-1302.
Hedge, P. S. et al., "Predictive Impact of Circulating Vascular Endothelial Growth Factor in Four Phase III Trials Evaluating Bevacizumab," *Clinical Cancer Research*, 19.4 (2013): 929-937.
Hicklin, D. J. et al., "Role of the vascular endothelial growth factor pathway in tumor growth and angiogenesis," *Journal of Clinical Oncology*, 23.5 (2005): 1011-1027.
Incio, J. et al., Obesity promotes resistance to anti-VEGF therapy in breast cancer by up-regulating IL-6 and potentially FGF-2, *Sci. Transl. Med.*, 10.eaag0945 (2018): 1-14.

(Continued)

*Primary Examiner* — Christine J Saoud
(74) *Attorney, Agent, or Firm* — pH IP Law

(57) ABSTRACT

Provided herein are methods for predicting whether a cancer patient will respond to treatment with bevacizumab based on determining a level of small extracellular vesicle (sEV)-associated VEGF in the patient. Also provided are methods of treating patients with either bevacizumab or a VEGFR tyrosine kinase inhibitor, a VEGFR neutralizing antibody, or a VEGF ligand trap based on the level of small extracellular vesicle (sEV)-associated VEGF in the patient.

3 Claims, 63 Drawing Sheets

(56) References Cited

OTHER PUBLICATIONS

Iwai, T. et al., "Continuous administration of bevacizumab plus capecitabine, even after acquired resistance to bevacizumab, restored anti-angiogenic and antitumor effect in a human colorectal cancer xenograft model," *Oncol. Rep.*, 36 (2016): 626-632.

Iwamoto, H. et al., "Cancer lipid metabolism confers antiangiogenic drug resistance," Cell Metabolism, 28 (2018): 104-117.

Jonasch, E. et al., "Phase II presurgical feasibility study of bevacizumab in untreated patients with metastatic renal cell carcinoma," *J. Clin. Oncol.*, 27.25 (2009): 4076-4081.

Kanada, M. et al., "Differential fates of biomolecules delivered to target cells via extracellular vesicles," *Proc. Natl. Acad. Sci. USA*, 112.12 (2015): E1433-1442.

Ko, S. Y. et al., "Abstract 783: Cancer cell-derived extracellular vesicles stimulate tumor angiogenesis by delivering VEGF to endothelial cells," *Cancer Res.*, 77, 13 Suppl. (2017):1.

Ko, S. Y. et al., "Cancer-derived small extracellular vesicles promote angiogenesis by heparin-bound, bevacizumab-insensitive VEGF, independent of vesicle uptake," *Communications Biology*, 2.386 (2019): 1-17.

Lambrechts, D. et al., "Markers of Response for the Antiangiogenic," *Journal of Clinical Oncology*, 31.9 (2013): 1219-1230.

Miles, D. et al., "Bevacizumab plus paclitaxel versus placebo plus paclitaxel as first-line therapy for HER2-negative metastatic breast cancer (MERiDiAN): A double-blind placebo-controlled randomised phase III trial with prospective biomarker evaluation," *Eur. J. Cancer*, 70 (2017): 146-155.

Mok, T. et al., "A correlative biomarker analysis of the combination of bevacizumab and carboplatin-based chemotherapy for advanced nonsquamous non-small-cell lung cancer: results of the phase II randomized ABIGAIL study (BO21015)," *J. Thorac. Oncol.*, 9.6 (2014): 848-855.

Muller, Y. A. et al., "VEGF and the Fab fragment of a humanized neutralizing antibody: crystal structure of the complex at 2.4 Å resolution and mutational analysis of the interface," *Structure*, 6.9 (1998): 1153-1167.

Muller, L. et al., "Tumor-derived exosomes regulate expression of immune function-related genes in human T cell subsets," *Sci. Rep.*, 6.20254 (2016): 1-13.

Paggetti, J. et al., "Exosomes released by chronic lymphocytic leukemia cells induce the transition of stromal cells into cancer-associated fibroblasts," *Blood*, 126.9 (2015): 1106-1117.

Pötgens, A. J. G. et al., "Covalent dimerization of vascular permeability factor/vascular endothelial growth factor is essential for its biological activity. Evidence from Cys to Ser mutations," *J. Biol. Chem.*, 269.52 (1994): 32879-32885.

Shibuya, M. et al., "Vascular Endothelial Growth Factor (VEGF) and Its Receptor (VEGFR) Signaling in Angiogenesis: A Crucial Target for Anti- and Pro-Angiogenic Therapies," *Genes & Cancer*, 2.12 (2011): 1097-1105.

Shojaei, F. et al., "Tumor refractoriness to anti-VEGF treatment is mediated by CD11b+Gr1+ myeloid cells," *Nat. Biotechnol.*, 25.8 (2007): 911-920.

Skog, J. et al., "Glioblastoma microvesicles transport RNA and proteins that promote tumour growth and provide diagnostic biomarkers," *Nat. Cell Biol.*, 10.12 (2008): 1470-1476.

Tang, M. K. S. et al., "Soluble E-cadherin promotes tumor angiogenesis and localizes to exosome surface," *Nat. Commun.*, 9.2270 (2018): 1-15.

Tanne, J. H., "FDA cancels approval for bevacizumab in advanced breast cancer," *BMJ*, 343.d7684 (2011).

Théry, C. et al., "Minimal information for studies of extracellular vesicles 2018 (MISEV2018): a position statement of the International Society for Extracellular Vesicles and update of the MISEV2014 guidelines," *J. Extracell. Vesicles*, 7.1535750 (2018): 1-43.

Treps, L. et al., "Glioblastoma stem-like cells secrete the pro-angiogenic VEGF—A factor in extracellular vesicles," *J. Extracell. Vesicles*, 6.1359479 (2017): 1-12.

Van Cutsem, E. et al., "Bevacizumab in combination with chemotherapy as first-line therapy in advanced gastric cancer: a biomarker evaluation from the AVAGAST randomized phase III trial," *J. Clin. Oncol.*, 30 (2012): 2119-2127.

Wijelath, E. et al., "Multiple mechanisms for exogenous heparin modulation of vascular endothelial growth factor activity," *J. Cell. Biochem.*, 111.2 (2010): 461-468.

Xu, R. et al., "Extracellular vesicles in cancer—implications for future improvements in cancer care," *Nat. Rev. Clin. Oncol.*, 15.10 (2018): 617-638.

Zhao, C. et al., "Hypoxic glioblastoma release exosomal VEGF—A induce the permeability of blood-brain barrier," *Biochem. Biophys. Res. Commun.*, 502.3 (2018): 324-331.

* cited by examiner

FIG. 2A

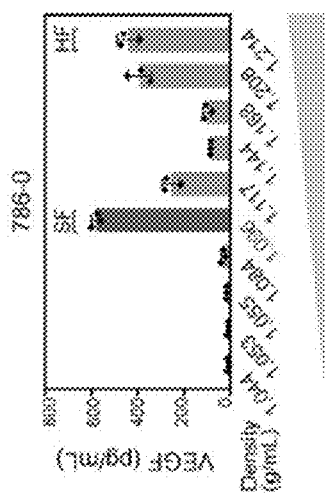
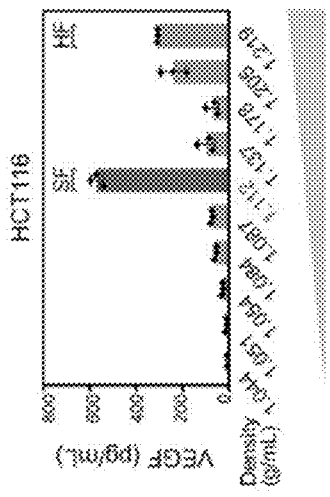
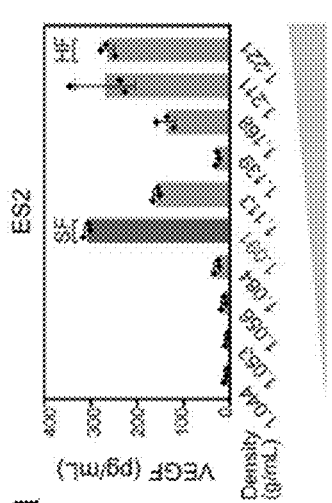
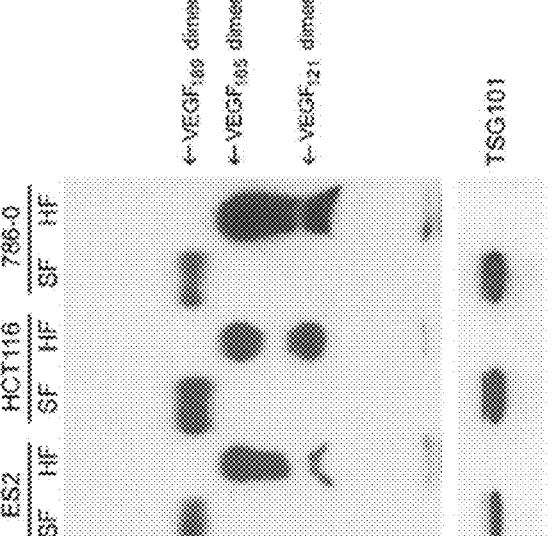
FIGS. 16A-16B

MEASUREMENT OF BEVACIZUMAB-INSENSITIVE VASCULAR ENDOTHELIAL GROWTH FACTOR-A

REFERENCE TO RELATED APPLICATIONS

The present application is a national phase application under 35 U.S.C. § 371 of International Application No. PCT/US2020/055922, filed Oct. 16, 2020, which claims the priority benefit of U.S. provisional application No. 62/916,472, filed Oct. 17, 2019, the entire contents of each of which are incorporated herein by reference.

STATEMENT REGARDING FEDERALLY SPONSORED RESEARCH

This invention was made with government support under grant number CA207034 awarded by the National Institutes of Health. The government has certain rights in the invention.

BACKGROUND

1. Field

The present invention relates generally to the fields of medicine and oncology. More particularly, it concerns methods for selecting patients with cancer for treatment with bevacizumab.

2. Description of Related Art

Bevacizumab is a humanized monoclonal antibody to human vascular endothelial growth factor (VEGF), a growth factor that stimulates blood vessel formation (i.e. angiogenesis). Bevacizumab is used to treat several types of cancer. A major limitation of bevacizumab is the lack of biomarkers that can reliably predict clinical response. Baseline (i.e. pre-treatment) levels of total circulating VEGF have been found to correlate with outcomes of cancer patients following bevacizumab treatment in some studies (Van Cutsem et al., 2012; Mok et al., 2014), but not in other studies (Hegde et al., 2013; Miles et al., 2017). As such, methods for determining whether a cancer patient will respond to treatment with bevacizumab are needed.

As such, provided herein are methods for selecting cancer patients for treatment with bevacizumab based on levels of circulating small extracellular vesicle-associated VEGF (sEV-VEGF), which were approximately 5-fold higher in cancer patients with progressing disease than in those with stable or regressing disease.

In one embodiment, provided herein are methods for measuring a level of bevacizumab-insensitive VEGF in a biological sample, the methods comprising (a) determining an amount of biologically active VEGF that is present in the sample; (b) determining an amount of bevacizumab-sensitive VEGF that is present in the sample; and (c) calculating a $\Delta$VEGF value by subtracting the amount of bevacizumab-sensitive VEGF from the amount of biologically active VEGF, wherein the $\Delta$VEGF value represents the level of bevacizumab-insensitive VEGF in the biological sample. In some aspects, the amount of biologically active VEGF that is present in the sample is determined by determining the amount of VEGF that is able to bind to a VEGF receptor (VEGFR). In various aspects, the VEGFR is VEGFR1, VEGFR2, or VEGFR1/R2-Fc. In some aspects, the amount of bevacizumab-sensitive VEGF that is present in the sample is determined by determining the amount of VEGF that is able to bind to bevacizumab. In various aspects; the biological sample is less than 1 mL, less than 750 μL, less than 500 μL, or less than 250 μL in volume. In various aspects, the biological sample is plasma, serum, ascites, peritoneal fluid, nipple aspirates, or urine. In various aspects, the methods can be performed in less than 1 day, less than 18 hours, less than 12 hours, or less than 6 hours.

In one embodiment, provided herein are methods of classifying a patient having a cancer; the method comprising: (a) obtaining a biological sample from the patient; (b) measuring a level of bevacizumab-insensitive VEGF in the sample; and (c) classifying the patient as having a bevacizumab-sensitive cancer if the level of bevacizumab-insensitive VEGF is not elevated relative to a reference level or classifying the patient as having a bevacizumab-resistant cancer if the level of bevacizumab-insensitive VEGF is elevated relative to a reference level. In some aspects, the level of bevacizumab-insensitive VEGF in the sample is measured using a method of any one of the present embodiments. In various aspects, the reference level is a level in a healthy patient or a level in a patient with stable or regressive cancer.

In one embodiment, provided herein are methods of classifying a patient having a cancer; the method comprising: (a) obtaining a biological sample from the patient; (b) measuring a level of small extracellular vesicle-associated VEGF (sEV-VEGF) in the sample; and (c) classifying the patient as having a bevacizumab-sensitive cancer if the level of sEV-VEGF is not elevated relative to a reference level or classifying the patient as having a bevacizumab-resistant cancer if the level of sEV-VEGF is elevated relative to a reference level. In various aspects, the reference level is a level in a healthy patient or a level in a patient with stable or regressive cancer.

In one embodiment, provided herein are methods of selecting a treatment for a patient having a cancer, the method comprising: (a) determining a level of bevacizumab-insensitive VEGF in a sample obtained from the patient; and (b) selecting the patient for treatment with bevacizumab if the level of bevacizumab-insensitive VEGF is not elevated relative to a reference level or selecting the patient for treatment with a VEGFR tyrosine kinase inhibitor, a VEGFR neutralizing antibody, or a VEGF ligand trap if the level of bevacizumab-insensitive VEGF is elevated relative to a reference level. In some aspects, the level of bevacizumab-insensitive VEGF in the sample is measured using a method of any one of the present embodiments. In various aspects, the reference level is a level in a healthy patient or a level in a patient with stable or regressive cancer.

In one embodiment, provided herein are methods of selecting a treatment for a patient having a cancer, the method comprising (a) determining a level of small extracellular vesicle-associated VEGF (sEV-VEGF) in a sample obtained from the patient, and (b) selecting the patient for treatment with bevacizumab if the level of sEV-VEGF is not elevated relative to a reference level or selecting the patient for treatment with a VEGFR tyrosine kinase inhibitor, a VEGFR neutralizing antibody, or a VEGF ligand trap if the level of sEV-VEGF is elevated relative to a reference level. In some aspects, step (a) comprises (i) obtaining or having obtained a biological sample from the patient; and (ii) performing or having performed an assay on the biological sample to determine the level of sEV-VEGF present in the sample. In various aspects, the reference level is a level in a healthy patient or a level in a patient with stable or regressive cancer.

In various aspects, the biological sample is plasma, serum, ascites, peritoneal fluid, nipple aspirates, or urine. In some aspects, the methods further comprise administering a therapeutically effective amount of bevacizumab to a patient classified as having a bevacizumab-sensitive cancer. In some aspects, the methods further comprise administering a therapeutically effective amount of a VEGFR tyrosine kinase inhibitor, a VEGFR neutralizing antibody, or a VEGF ligand trap to a patient classified as having a bevacizumab-resistant cancer.

In various aspects, the methods further comprise administering at least a second anti-cancer therapy to the patient. In some aspects, the second anti-cancer therapy is a surgical therapy, chemotherapy, radiation therapy, cryotherapy, hormonal therapy, toxin therapy, immunotherapy, or cytokine therapy.

In various aspects, the patient has previously undergone at least one round of anti-cancer therapy. In various aspects, the patient has not previously undergone anti-cancer therapy. In various aspects, the patient has previously failed to respond to treatment. In various aspects, the patient has relapsed following treatment. In various aspects, the patient is a human.

In various aspects, the methods further comprise reporting the classification or selection of the patient. In some aspects, the reporting comprises preparing a written or electronic report. In further aspects, the methods comprise providing the report to the patient, a doctor, a hospital, or an insurance company.

In various aspects, the methods further comprise performing the classification or selection a second time. In some aspects, the second time is during a course of bevacizumab treatment.

In one embodiment, provided herein are methods of treating a patient having a cancer, the method comprising administering a therapeutically effective amount of bevacizumab to the patient, wherein the patient's level of bevacizumab-insensitive VEGF is not elevated relative to a reference level. In some aspects, the level of bevacizumab-insensitive VEGF in the sample is measured using a method of any one of the present embodiments. In various aspects, the reference level is a level in a healthy patient or a level in a patient with stable or regressive cancer.

In one embodiment, provided herein are methods of treating a patient having a cancer, the method comprising administering a therapeutically effective amount of bevacizumab to the patient, wherein the patient's level of sEV-VEGF is not elevated relative to a reference level.

In one embodiment, provided herein are methods of treating a patient having a cancer, the method comprising: (a) determining a level of bevacizumab-insensitive VEGF in a sample obtained from the patient; (b) selecting or having selected the patient for treatment with bevacizumab when the level of bevacizumab-insensitive VEGF is not elevated relative to a reference level; and (c) administering or having administered to the selected patient a therapeutically effective amount of bevacizumab. In some aspects, step (a) comprises (i) obtaining or having obtained a biological sample from the patient; and (ii) performing or having performed an assay on the biological sample to determine the level of bevacizumab-insensitive VEGF. In some aspects; the level of bevacizumab-insensitive VEGF in the sample is measured using a method of any one of the present embodiments.

In one embodiment, provided herein are methods of treating a patient having a cancer, the method comprising: (a) determining a level of small extracellular vesicle-associated VEGF (sEV-VEGF) in a sample obtained from the patient; (b) selecting or having selected the patient for treatment with bevacizumab when the level of sEV-VEGF is not elevated relative to a reference level; and (c) administering or having administered to the selected patient a therapeutically effective amount of bevacizumab. In some aspects, step (a) comprises (i) obtaining or having obtained a biological sample from the patient; and (ii) performing or having performed an assay on the biological sample to determine the level of sEV-VEGF.

In one embodiment, provided herein is the use of bevacizumab in the manufacture of a medicament for the treatment of a patient having an non-elevated level of sEV-VEGF relative to a reference level.

In one embodiment, provided herein is bevacizumab for use in the treatment of a patient having an non-elevated level of sEV-VEGF relative to a reference level.

In one embodiment, provided herein are methods of treating a patient having a cancer, the method comprising administering a therapeutically effective amount of a VEGFR tyrosine kinase inhibitor, a VEGFR neutralizing antibody, or a VEGF ligand trap to the patient; wherein the patient's level of bevacizumab-insensitive VEGF is elevated relative to a reference level. In some aspects, the level of bevacizumab-insensitive VEGF in the sample is measured using a method of any one of the present embodiments.

In one embodiment, provided herein are methods of treating a patient having a cancer, the method comprising administering a therapeutically effective amount of a VEGFR tyrosine kinase inhibitor, a VEGFR neutralizing antibody, or a VEGF ligand trap to the patient, wherein the patient's level of sEV-VEGF is elevated relative to a reference level.

In one embodiment, provided herein are methods of treating a patient having a cancer, the method comprising: (a) determining a level of bevacizumab-insensitive VEGF in a sample obtained from the patient; (b) selecting or having selected the patient for treatment with a VEGFR tyrosine kinase inhibitor, a VEGFR neutralizing antibody, or a VEGF ligand trap when the level of bevacizumab-insensitive VEGF is elevated relative to a reference level; and (c) administering or having administered to the selected patient a therapeutically effective amount of a VEGFR tyrosine kinase inhibitor, a VEGFR neutralizing antibody, or a VEGF ligand trap. In some aspects, step (a) comprises (i) obtaining or having obtained a biological sample from the patient; and (ii) performing or having performed an assay on the biological sample to determine the level of bevacizumab-insensitive VEGF. In some aspects; the level of bevacizumab-insensitive VEGF in the sample is measured using a method of any one of the present embodiments.

In one embodiment, provided herein is the use of a VEGFR tyrosine kinase inhibitor, a VEGFR neutralizing antibody, or a VEGF ligand trap in the manufacture of a medicament for the treatment of a patient having an elevated level of bevacizumab-insensitive VEGF relative to a reference level.

In one embodiment, provided herein is a VEGFR tyrosine kinase inhibitor, a VEGFR neutralizing antibody, or a VEGF ligand trap for use in the treatment of a patient having an elevated level of bevacizumab-insensitive VEGF relative to a reference level.

In one embodiment; provided herein are methods of treating a patient having a cancer, the method comprising: (a) determining a level of small extracellular vesicle-associated VEGF (sEV-VEGF) in a sample obtained from the patient; (b) selecting or having selected the patient for treatment with a VEGFR tyrosine kinase inhibitor, a VEGFR neutralizing antibody, or a VEGF ligand trap when the level of sEV-VEGF is elevated relative to a reference level; and (c) administering or having administered to the selected patient a therapeutically effective amount of a VEGFR tyrosine kinase inhibitor, a VEGFR neutralizing antibody, or a VEGF ligand trap in some aspects, step (a) comprises (i) obtaining or having obtained a biological sample from the patient; and (ii) performing or having performed an assay on the biological sample to determine the level of sEV-VEGF.

In one embodiment, provided herein is the use of a VEGFR, tyrosine kinase inhibitor, a VEGFR neutralizing antibody, or a VEGF ligand trap in the manufacture of a medicament for the treatment of a patient having an elevated level of sEV-VEGF relative to a reference level.

In one embodiment, provided herein is a VEGFR tyrosine kinase inhibitor, a VEGFR neutralizing antibody, or a VEGF ligand trap for use in the treatment of a patient having an elevated level of sEV-VEGF relative to a reference level.

In various aspects, the methods further comprise administering at least a second anti-cancer therapy to the patient. In some aspects, the second anti-cancer therapy is a surgical therapy, chemotherapy, radiation therapy, cryotherapy, hormonal therapy, toxin therapy, immunotherapy, or cytokine therapy.

In various aspects, the patient has previously undergone at least one round of anti-cancer therapy. In various aspects, the patient has not previously undergone anti-cancer therapy. In various aspects, the patient has previously failed to respond to treatment. In various aspects, the patient has relapsed following treatment. In various aspects, the patient is a human. In various aspects, the reference level is a level in a healthy patient or a level in a patient with stable or regressive cancer.

In various aspects, the methods further comprise reporting the selection of the patient. In some aspects, the reporting comprises preparing a written or electronic report. In further aspects, the methods comprise providing the report to the patient, a doctor, a hospital, or an insurance company.

In various aspects, the methods further comprise performing the selection a second time. In some aspects, the second time is during a course of bevacizumab treatment.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, the variation that exists among the study subjects, or a value that is within 10% of a stated value.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1A) Immunoblot of TSG101 and flotillin-1 in fractions of the indicated buoyant densities that were isolated from media conditioned by ovarian (ES2), colorectal (HCT116) and renal (786-0) cancer cell lines and from ovarian cancer patient ascites. (FIG. 1B) Immunogold labeling of CD63 on vesicles in sEV fractions (i.e. density of 1.09 to 1.13 g/ml). Scale bar=1.00 nm. (FIGS. 1C-1F) Human umbilical vein endothelial cells (HUVEC) were pretreated with endocytosis inhibitors (chlorpromazine, CPL; dynasore, DYN) or with dimethyl sulfoxide (DMSO) solvent, and then stimulated with sEVs of ES2, HCT116 and 786-0 cells. Shown are numbers (FIG. 1C) and representative images (FIG. 1D) of migrating HUVEC at 5 h after stimulation, and numbers (FIG. 1E) and representative images (FIG. 1F) of tubes formed at 4 h after stimulation. In FIGS. 1C and 1E, the bars in each group represent, from left to right, DMSO, CPZ, and DYN. Mean±SD of n=4 independent experiments are shown. Scale bar=100 μm. (FIGS. 1G-1H) HUVEC were treated as in FIG. 1C and evaluated for uptake of PKH2.6 dye-labeled sEVs by flow cytometry at 5 h thereafter. Shown are mean fluorescence intensity (MFI) values of PKH26 fluorescence detected in HUVEC in n=3 independent experiments (FIG. 1G) and representative histogram plots (FIG. 1H). In FIG. 1H, the plot that is shifted to the right of the others is ES2 sEV+ DMSO, Gating strategy and contour plots are shown in FIG. 10B and FIG. 11B, respectively. P<0.01, *P<0.001, ****P<0.0001, by ANOVA with Bonferroni's corrections; one-way in FIG. 1G, two-way in FIGS. 1C&E. ns: not significant.

FIGS. 2A-2D. VEGF is present on the surface of cancer cell-derived sEVs. (FIG. 2A) Detection of angiogenesis-related proteins in sEVs of ES2 cells by antibody (Ab) array. (FIG. 2B) Levels of angiogenic factors detected by enzyme-linked immunosorbent assays (ELISA) in lysates of sEVs (grey bars) and on the surface of equivalent amounts of intact sEVs (magenta bars) of ES2, HCT116, and 786-0 cells. CD63 and TSG101 were assayed as positive and negative controls for sEV surface protein, respectively. The bars in each pair represent, from left to right, sEV lysate and intact sEV. Shown are mean±SD of n=3 independent experiments. *P<0.05, P 0.01, **P<0,0001, by two-sided unpaired t-test. (FIG. 2C) To detect sEV surface protein by flow cytometry, microbeads were coupled to the indicated Ab, incubated with sEVs of parental (VEGF+/+) and VEGF-deficient (VEGF−/−) HCT116 cells and then stained with exo-FITC dye to label sEV membrane. Binding of Ab to protein on the surface of sEVs was evaluated by analyzing exo-FITC fluorescence in the gated population of Ab-coupled microbeads. Shown are representative histogram plots of fluorescence. In each of the right-hand plots, the line that is shifted to the tight of the others represents VEGF$^{+/+}$ sEV. Gating strategy, contour plots and MFI values of n=3 independent experiments are shown in FIG. 13A-13C. (FIG. 2D) Immunogold labeling of VEGF on sEVs isolated from parental cancer cell lines and from ovarian cancer patient ascites. Scale bar=100 nm.

(FIG. 3A) Immunoblot of phosphorylated VEGF receptor 2 (p-VEGFR2) and total VEGF receptor 2 (VEGFR2) in HUVEC at 5 min following stimulation with sEVs of ES2, HCT116 and 786-0 cells or with recombinant VEGF$_{165}$ (rVEGF$_{165}$). (FIGS. 3B-3E) HUVEC were pretreated with inhibitors of VEGFR tyrosine kinase activity (FIGS. 3B,3C) and with neutralizing Ab to VEGFR2 (FIGS. 3D, 3E), stimulated with sEVs or rVEGF$_{165}$, and then assayed for tube formation at 4 h thereafter. In FIG. 3B, the bars in each group represent, from left to right, DMSO, Axitinib, and Vandetanib. In FIG. 3D, the bars in each pair represent, from left to right, Control Ig and VEGFR2 Ab. In FIGS. 3B&3D, shown are mean±SD of n=4 independent experiments. In FIGS. 3C&3E, shown are representative images of tube formation. Scale bar=100 μm. (FIG. 3F) VEGF levels in conditioned media (CM) of ES2 and HCT116 cells that were depleted of sEVs (sEV-dep) or left non-depleted (whole). The bars in each pair represent, from left to right, Whole and sEV-dep. Shown are mean±SD of n=3 independent experiments. (FIGS. 3G-3I) HUVEC were stimulated with whole and sEV-depleted conditioned media and then assayed for VEGFR2 phosphorylation (FIG. 3G) and tube formation (FIGS. 3H,3I). In FIG. 3H, the bars in each pair represent, from left to right, Whole and sEV-dep. In FIG. mean±SD of n=4 independent experiments. In (FIG. 3I), representative images of tube formation. Scale bar=100 μm, P<0.01, *P<0.001, ****P<0.0001, by two-way ANOVA with Bonferroni's corrections in FIGS. 3B,3D,3H, and by two-sided unpaired t-test in FIG. 3F.

(FIGS. 4A-4C) HUVEC were stimulated with equivalent amounts of sEVs of VEGF$^{+/+}$ cancer cells, sEVs of VEGF$^{-/-}$ cancer cells or rVEGF$_{165}$, and then assayed for VEGFR2 phosphorylation (FIG. 4A) and tube formation (FIGS. 4B,4C). In FIG. 4B, mean±SD of n=4 independent experiments. In FIG. 4C, representative images of tube formation. Scale bar=100 μm. (FIGS. 4D-4F) Nude mice were inoculated intraperitoneally (i.p.) with ES2 VEGF$^{-/-}$ cells that stably expressed green fluorescent protein (CEP). At 7 days thereafter when tumors were palpable, mice were randomized into groups (n=6 mice per group) and then administered equivalent amounts of sEVs of ES2 VEGF$^{+/+}$ cells or sEVs of ES2 VEGF$^{-/-}$ cells, 3 times a week for 2 weeks. Negative and positive control groups of tumor-bearing mice were administered saline and rVEGF$_{165}$, respectively. In FIG. 4D, representative images of GFP-expressing tumors in the abdominal cavity viewed under a fluorescence stereomicroscope. Arrows indicate tumors on the momentum. Scale bar=10 mm. In FIG. 4E, immuno-fluorescence staining of the endothelial cell marker CD31 (red) in sections of omental tumors (Ome T) adjacent to the pancreas (Pane). Scale bar=100 μm. In FIG. 4F, amount of i.p. tumor burden, numbers of intratumoral CD31$^+$ cells and volume of ascites in each mouse in each of the groups. I.p. tumor burden is expressed as % of area of GFP fluorescence in the abdominal cavity. Numbers of CD31$^+$ cells were scored in 5 random 100× fields per omental tumor section and an average score was determined for each mouse. Error bars in FIG. 4F represent SD. *P<0.001, **P<0.0001, by one-way ANOVA with Bonferroni's corrections in FIGS. 4B&F.

(FIG. 5A) Immunoblot of cellular VEGF in lysates of cells of parental cancer cell lines that were treated with brefeldin A to block protein secretion. Recombinant VEGF proteins were included as controls. Overexposure shows VEGF$_{121}$ and VEGF$_{165}$ dimers. (FIG. 5B) Immunoblot of VEGF in sEVs isolated from the same cell lines as in FIG. 5A but without brefeldin A treatment. (FIG. 5C) Immunoblot of VEGF in tumor tissues (T) of 3 patients with ovarian cancer and in sEVs isolated from ascites of the same patients. (FIG. 5D) Immunoblot of VEGF in sEVs isolated from serum or plasma of 5 patients with colorectal carcinoma (CRC) and 2 patients with renal cell carcinoma (RCC). TSG101 was assayed as a control in FIGS. 5C&D.

(FIG. 6A.) VEGF levels in conditioned media and sEVs of ES2 VEGF$^{-/-}$ and HCT116 VEGF$^{-/-}$ cells stably transfected with VEGF$_{121}$, VEGF$_{165}$ or VEGF$_{189}$. TSG101 was assayed in sEVs as a control. The bars in each group represent, from top to bottom, Non-transfected, Transfected with VEGF$_{121}$, Transfected with VEGF$_{165}$, and Transfected with VEGF$_{189}$. Mean±SD of n=3 independent experiments are shown. (FIGS. 6B,6C) VEGF levels in whole and sEV-depleted conditioned media of VEGF$^{-/-}$ cells transfected with VEGF$_{189}$ (FIG. 613) and VEGF$_{121}$ (FIG. 6C). Mean±SD of n=3 independent experiments are shown. (FIG. 6D) Conditioned media of non-transfected VEGF$^{-/-}$ cells was incubated with recombinant VEGF$_{189}$ (rVEGF$_{189}$) that was added at a concentration equivalent to the VEGF concentration in conditioned media of VEGF$_{189}$-transfected VEGF$^{-/-}$ cells (2500 μg/ml for ES2; 1500 pg/ml for HCT116; see data in FIG. 6A). Thereafter, sEVs were isolated. Amounts of VEGF$_{189}$ detected in these sEVs were compared with VEGF content in sEVs secreted by VEGF$_{189}$-transfected VEGF$^{-/-}$ cells. Mean±SD of n=3 independent experiments are shown. (FIG. 6E) Levels of human VEGF$_{189}$ in conditioned media and sEVs of CHO-K1 and pgsD-677 cells stably transfected with human VEGF$_{189}$. Mean±SD of n=3 independent experiments are shown. (FIGS. 6F,6G) PKE167-labeled sEVs of parental ES2 cells were pretreated with heparinase, chondroitinase or no enzyme, and then incubated with VEGF Ab coupled to microbeads. VEGF on the surface of sEVs was detected by flow cytometric analysis of PKH67 fluorescence in Ab-coupled microbeads (solid histograms), Dotted histograms show background fluorescence when sEVs were incubated with control Ig-coupled beads. As a negative control for enzymatic digestion, the same approach was used to detect the transmembrane protein CD63. In FIG. 6F, representative histogram plots. In FIG. 6G, MFI values of n=3 independent experiments (mean±SD). Contour plots are shown in FIG. 17. (FIG. 6H) rVEGF$_{189}$ and sEVs with an equivalent content of VEGF were added to healthy donor plasma. Following incubation at 37° C. for the indicated times; VEGF levels in plasma were assayed. Shown are mean±SD of n=2 independent experiments. P<0.01, *P<0.001, ****P<0.0001, by one-way ANOVA with Bonferroni's corrections in FIGS. 6A&G, by two-sided unpaired t-test in FIGS. 6B-6E.

(FIGS. 7A,7B) rVEGF$_{189}$ was captured by high molecular weight (HMW) heparin or by VEGF capture Ab (positive control), and then incubated with bevacizumab or VEGFR1/R2-Fc, where VEGFR1/F2-Fc is a chimeric protein that consists of the ligand-binding domains of VEGFR1 and VEGFR2 fused to Fc portion of human Ig Bevacizumab bound to VEGF$_{189}$ and VEGFR1/R2-Fc bound to VEGF$_{189}$ were detected by anti-human IgG. In FIG. 7A, experimental scheme. In FIG. 7B, relative levels of bevacizumab bound to VEGF$_{189}$ and VEGFR1/R2 bound to VEGF$_{189}$. In FIG. 7B, each pair of bars represents, from left to right; VEGF capture Ab and HMW heparin. Shown are mean±SD of n=6 independent experiments. (FIGS. 7C,7D) Microbeads were coupled to bevacizumab, incubated with sEVs of VEGF$^{+/+}$ cells or sEVs of VEGF$^{-/-}$ cells; and then stained with exo-FITC dye to label sEV membrane. The same procedure was performed using microbeads coupled to VEGFR1/R2-Fc (positive control). Binding of bevacizumab and VEGFR1/R2-Fc to VEGF on the surface of sEVs was evaluated by flow cytometric analysis of exo-FITC fluorescence in the gated population of microbeads. In FIG. 7C, representative histogram plots; in the bottom two panels, the right shifted line represents ES2 VEGF$^{+/+}$ sEV. In the top two panels of FIG. 7D, the bars in each group represent, from left to right, No sEV, ES2 VEGF$^{+/+}$ sEV, and ES2 VEGF$^{-/-}$ sEV. In the bottom two panels of FIG. 7D, the bars in each group represent, from left to right, No sEV, HCT116 VEGF$^{+/+}$ sEV, and HCT116 VEGF$^{-/-}$ sEV. in FIG. 7D, MFI values of n=3 independent experiments (mean±SD). Gating strategy is shown in FIG. 13A. Contour plots are shown in FIG. 19A. (FIG. 7E) Bevacizumab and VEGFR1/R2-Fc were incubated with recombinant VEGF and with sEVs that have a VEGF content equivalent to the range of amounts of recombinant VEGF. Following incubation, levels of unbound bevacizumab and unbound VEGFR1/R2-Fc were assayed. Shown are mean±SD of n=3 independent experiments. (FIGS. 7F-7H) HUVEC were stimulated with sEVs or rVEGF$_{189}$ that were pre-incubated with control Ig, bevacizumab or VEGFR1/R2-Fc, and then assayed for phosphorylated and total VEGFR2 (FIG. 7F) and tube formation (FIGS. 7G,7H). In FIG. 7G, the bars in each group represent, from left to right, Control Ig, Bevacizumab, and VEGFR1/R2-Fc. In FIG. 7G, mean±SD of n=3 independent experiments. In FIG. 7H, representative images of tube formation. Scale bar=100 μm. *P<0.05, *P<0.001, P<0.0001 by ANOVA with Bonferroni's corrections; one-way in FIG. 7D; two-way in FIGS. 7B&G**.

(FIGS. 8A-8E) Nude mice were inoculated i.p. with GFP-expressing ES2 VEGF$^{-/-}$ cells. At 7 days thereafter when tumors were palpable, mice were randomized into groups (n=6 mice per group) and then administered sEVs of ES2 VEGF$^{+/+}$ cells in combination with either normal human IgG (negative control) or bevacizumab, or rVEGF$_{189}$ in combination with either normal human IgG (negative control) or bevacizumab, 3 times a week for 2 weeks. In FIG. 8A, representative images of GFP-expressing tumors in the abdominal cavity. Arrows indicate tumors on the momentum. Scale bar=10 mm. In FIG. 8B, immunofluorescence staining of CD31 (red) in sections of omental tumors (Ome T) adjacent to the pancreas (Pane). Scale bar=100 μm. Amount of i.p. tumor burden (FIG. 8C), numbers of intratumoral CD31$^{+}$ cells (FIG. 8D) and volume of ascites (FIG. 8E) in each mouse in control (Cont) and bevacizumab (Bev) treatment groups. *P<0.001, P<0.0001, by two-sided unpaired t-test. (FIGS. 8F,8G) Baseline (i.e. pre-treatment) plasma levels of total VEGF (FIG. 8F) and sEV-VEGF (FIG. 8G**) in 17 patients with newly diagnosed metastatic renal cell carcinoma who were treated presurgically with single-agent bevacizumab for 8 weeks and thereafter restaged. P values were determined by Mann-Whitney U-test.

(FIG. 9A) Immunoblots of TSG101, flotillin-1, HSP70, α-actinin-4, HSP90B1 (also known as GP96, endoplasmin) and calnexin in cellular extracts of ES2, HCT116 and 786-0 cells (Cell), and in lysates of EVs of buoyant densities ranging from 1.09 to 1.13 g/mL that were isolated from media conditioned by these cells (sEV). (FIG. 9B) EVs of buoyant densities of 1.09 to 1.13 g/mL were evaluated for particle size distribution by nanoparticle tracking analysis. Each plot shows the combined result of 10 replicate measurements.

(FIG. 10A) Representative images of PKH26 fluorescence detected by fluorescence microscopy in HUVEC. Nuclei were visualized by staining with 4',6-diamidino-2-phenyl-indole dihydrochloride (DAN). Scale bar=20 μm. (FIGS. 10B-10D) Evaluation of sEV uptake by flow cytometry. Shown are forward and side scatter analysis indicating the gating used to select the population of live HUVEC within which PKH26 fluorescence was analyzed (FIG. 10B), representative contour plots of PKH26 fluorescence detected in HUVEC (FIG. 10C), and mean fluorescence intensity (MFI) values of n=3 independent experiments (mean±SD) (FIG. 10D). A minimum of 10,000 gated events were analyzed for each sample.

(FIG. 11A) Representative images of PKH26 fluorescence detected by fluorescence microscopy in HUVEC. Scale bar=20 μm. (FIG. 11B) Representative contour plots of PKH26 fluorescence detected in HUVEC by flow cytometry.

FIGS. 12A-120. Analysis of isogenic VEGF$^{+/+}$ and VEGF$^{-/-}$ cancer cell lines. (FIGS. 12A-12C) Confirmation of lack of VEGF in ES2 cells in which the VEGFA gene was deleted by CRISPR/Cas9 gene editing and in a previously generated HCT116 VEGF$^{-/-}$ cell line (Dang et al., 2006). Shown are immunoblots of VEGF in cellular extracts (FIG. 12A), levels of VEGF in conditioned media (FIG. 1211), and amounts of VEGF in sEVs of parental (VEGF$^{+/+}$) and VEGF$^{-/-}$ cell lines (FIG. 12C). Mean±SD of n=3 independent experiments are shown in FIGS. 12B&12C. **P<0.0001, by two-sided unpaired t-test. (FIG. 12D) Evaluation of particle size distribution of sEVs of VEGF$^{-/-}$ cancer cells by nanoparticle tracking analysis. Each plot shows the combined result of 10 replicate measurements. Particle size distribution of sEVs of parental lines is shown in FIG. 9B**.

(FIG. 13A) Representative example of forward and side scatter analysis indicating the gating used to select the population of singlet Ab-coupled microbeads within which exo-FITC fluorescence was analyzed. A minimum of 10,000 gated events were analyzed for each sample. (FIG. 13B) Representative contour plots of exo-FITC fluorescence. (FIG. 13C) MFI values of n=3 independent experiments (mean±SD). The bars in each group represent, from top to bottom, No sEV, VEGF$^{+/+}$ sEV, and VEGF$^{-/-}$ sEV.  P<0.01, * P<0001, **** P<0,0001, by one-way ANOVA with Bonferroni's corrections.

(FIG. 14A) To optimize flow cytometry settings for sEV detection, size marker beads of different diameters (50 nm, 100 nm, 200 nm, 500 nm) were acquired. Shown are forward and side scatter analyses indicating the populations of beads. (FIG. 14B) Isolated sEVs were acquired using the same settings as in FIG. 14A. Shown is a representative example of forward and side scatter analysis indicating the gating used to select the population of sEVs. (FIG. 14C) To optimize settings for detecting proteins on the surface of sEVs by flow cytometry, sEVs were directly stained with phycoerythrin/Cy7 (PE/Cy7)-conjugated isotype control in combination with fluorescein isothiocyanate (FITC)-conjugated isotype control, CD63 Ab, CD81 Ab or CD9 Ab. FITC and PE/Cy7 fluorescence were analyzed within the gated population of sEVs. A minimum of 10,000 gated events were analyzed for each sample. Shown are representative contour plots of staining detected in sEVs of SKOV3 cells. Percentages of sEVs in each quadrant are indicated. (FIGS. 14D-14E) sEVs were directly stained with phycoerythrin (PE)-conjugated VEGF Ab or isotype control in combination with PE/Cy7-conjugated CD63 Ab (positive control) or isotype control. PE and PE/Cy7 fluorescence were analyzed within the gated population of sEVs. A minimum of 10,000 gated events were analyzed for each sample. Shown are representative contour plots of staining detected in sEVs of ES2 VEGF$^{+/+}$ and VEGF$^{-/-}$ cells (FIG. 14D) and sEVs of HCT116 VEGF$^{+/+}$ and VEGF$^{-/-}$ cells (FIG. 14E). Percentages of sEVs in each quadrant are indicated.

(FIG. 15A) Total volume of ascites in each mouse. (FIG. 15B) Concentrations of tumor-derived sEV-VEGF and stroma-derived sEV-VEGF in ascites of each mouse were determined by isolating sEVs from ascites and then assaying VEGF in sEVs by human- and mouse-specific VEGF ELISA, respectively. **** P<0.0001, by two-sided paired t-test.

FIGS. 16A-16B. Analysis of VEGF in fractions isolated by density gradient ultracentrifugation. (FIG. 16A) Fractions of the indicated buoyant densities (1.0 mL in volume) were isolated by density gradient ultracentrifugation from media conditioned by ES2, HCT116 and 786-0 cells. A 100 µL aliquot of each fraction was evaluated for VEGF content by ELISA. Shown are mean±SD of n=3 independent assays. (FIG. 16B) Immunoblot of VEGF in fractions within the buoyant density range of sEVs (SF) and in fractions of the highest buoyant density (HF). Specific fractions are indicated in FIG. 16A. Equivalent volumes of each fraction (40 µL) were assayed. TSG101 was assayed as a control.

(FIGS. 18A-18C) To confirm that binding of bevacizumab to VEGF can be detected by flow cytometry, isogenic VEGF$^{+/+}$ and VEGF$^{-/-}$ cancer cells were treated with brefeldin A, permeabilized and then incubated with control Ig, bevacizumab or VEGFR1/R2-Fc. Binding to intracellular VEGF was detected by staining with Peridinin-Chlorophyll-Protein (PerCP)-conjugated anti-human Ig. Shown are a representative example of forward and side scatter analysis indicating the gating used to select the population of permeabilized cancer cells within which intracellular staining was analyzed (FIG. 18A), representative histogram plots of intracellular staining (FIG. 18B), and MFI values of n=3 independent experiments (mean±SD) (FIG. 18C). In FIG. 18B, in the two left panels, the left shifted line represents Control Ig. In FIG. 18C, the bars in each group represent, from left to right, Control Ig, Bevacizumab, and VEGFR1/R2-Fc. ** P<0.0001, by two-way ANOVA with Bonferroni's corrections. A minimum of 10,000 gated events were analyzed for each sample. (FIG. 18**D) To confirm that bevacizumab was coupled to microbeads that were used for incubation with sEVs, microbeads were stained with anti-bevacizumab Ab and staining evaluated by flow cytometry (solid histogram). Dotted histogram indicates staining of beads with isotype control.

(FIG. 19A) To evaluate the ability of bevacizumab to bind sEV-VEGF, microbeads were coupled to bevacizumab, incubated with sEVs of VEGF$^{+/+}$ cells or sEVs of VEGF$^{-/-}$ cells (negative control) and then stained with exo-FITC dye to label sEV membrane. The same procedure was performed using microbeads coupled to VEGFR1/R2-Fc (positive control). Binding of bevacizumab and VEGFR1/R2-Fc to sEV-VEGF was assayed by flow cytometric analysis of exo-FITC fluorescence in the gated population of microbeads. Gating strategy is shown in FIG. 13A. A minimum of 10,000 gated events were analyzed for each sample. Shown are representative contour plots of exo-FITC; fluorescence. (FIGS. 19B-19C) To evaluate the ability of bevacizumab to neutralize sEV-VEGF under conditions where soluble VEGF and sEVs carrying VEGF are co-secreted, conditioned media was collected from parental ES2 and HCT116 cells and either depleted of sEVs or left non-depleted (i.e. whole). As a control, rVEGF$_{189}$ was added to sEV-depleted media at a concentration equivalent to the concentration of sEV-VEGF in whole media (i.e. 400 pg/mL, refer FIG. 3F). In FIG. 19B, whole and sEV-depleted media were incubated with bevacizumab (20 ng/mL) and thereafter assayed for levels of unbound bevacizumab. Shown are mean±SD of n=4 independent experiments.  P<0.01,  P<0,0001, by one-way ANOVA with Bonferroni's corrections. in FIG. 19**C, HUVEC were stimulated with whole and sEV-depleted conditioned media (CM) of parental ES2 cells with the addition of bevacizumab or control Ig, and then assayed for VEGFR2 phosphorylation by immunoblot.

(FIG. 20A) Volumes of s.c. tumors at pre- and post-treatment time-points. (FIG. 20B) VEGF levels in whole plasma. (FIG. 20C) VEGF levels in sEV-depleted plasma (representing non-sEV-VEGF). (FIG. 20D) Levels of sEV-VEGF estimated from the difference between VEGF levels in whole and sEV-depleted plasma. In FIGS. 20A-20D, the bars in each pair represent; from left to right, Control Ig and Bevacizumab. * P<0.05,  P<0.01, * P<0.001, by one-way ANOVA with Bonferroni's corrections.

(FIG. 21A) Immunoblots of TSG101, flotillin-1, HSP70, α-actinin-4, HSP90B1 and calnexin in sEVs isolated from plasma samples of 5 patients (lanes 4 to 8). Included as controls are sEVs that were isolated from 786-0 renal cancer cells by using ExoQuick reagent (lane 3) and by density gradient ultracentrifugation (lane 2). Cellular extract of 786-0 cells was included as a positive control for non-sEV markers (lane 1). (FIG. 21B) Evaluation of particle size distribution of sEVs isolated from plasma samples of 4 patients by nanoparticle tracking analysis. Each plot shows the combined result of 10 replicate measurements.

FIG. 24. Cohort 1. Patients newly diagnosed with advanced-stage ovarian or fallopian tube carcinoma who were treated with bevacizumab in combination with chemotherapy following tumor-debulking surgery.

FIG. 25A-25C. Correlations between progression-free survival (PFS) and VEGF levels in Cohort 1. Levels of VEGF capable of binding to VEGFR1/R2-Fc (FIG. 25A), levels of VEGF capable of binding to bevacizumab (FIG. 25B), and ΔVEGF values (FIG. 25C) were determined in baseline (i.e. pre-treatment) serum samples of patients in Cohort 1 by using the immunoassays shown in FIG. 22, and thereafter evaluated for correlations with PFS. Correlation coefficients were determined by Spearman test.

DETAILED DESCRIPTION

Cancer cell-derived sEVs can stimulate endothelial cell migration and tube formation independently of uptake. These responses are mediated by the 189 amino acid, heparin-bound isoform of VEGF that, unlike other common isoforms of VEGF, is enriched on the surface of sEVs. Furthermore, sEV-associated VEGF (sEV-VEGF) is highly stable and not neutralized by the therapeutic VEGF antibody bevacizumab. As such, elevated levels of sEV-VEGF contribute, at least in part, to the resistance of tumors to bevacizumab. Therefore, detection of sEV-VEGF in body fluids (i) can be performed prior to cancer treatment as a method of identifying cancer patients who would likely benefit from treatment with bevacizumab and also (ii) can be performed during the course of bevacizumab treatment as a method of monitoring response to this treatment.

I. ASPECTS OF THE PRESENT INVENTION sEV-mediated intercellular communication has been described in diverse contexts including the tumor microenvironment, and predominantly thought to occur through uptake of vesicular cargo by recipient cells (Xu et al., 2018; Fang et al., 2018; Paggetti et al., 2015; Skog et al., 2008; Zhou et al., 2014; Hsu et al., 2017). However, recent studies have shown that sEVs can also signal to recipient cells via proteins on the vesicular surface, such as PD-L1 and E-cadherin (Chen et al., 2018; Tang et al., 2018). Several growth factors including VEGF have been detected in cancer cell-derived sEVs and have been assumed to be luminal constituents (Paggetti et al., 2015; Skog et al., 2008). VEGF has been implicated in the angiogenic activity of these sEVs (Treps et al., 2017; Zhao et al., 2018), but there has been no explanation as to how this ligand elicits its signals if it is encapsulated within sEVs and then internalized in recipient cells.

Figure 5A:
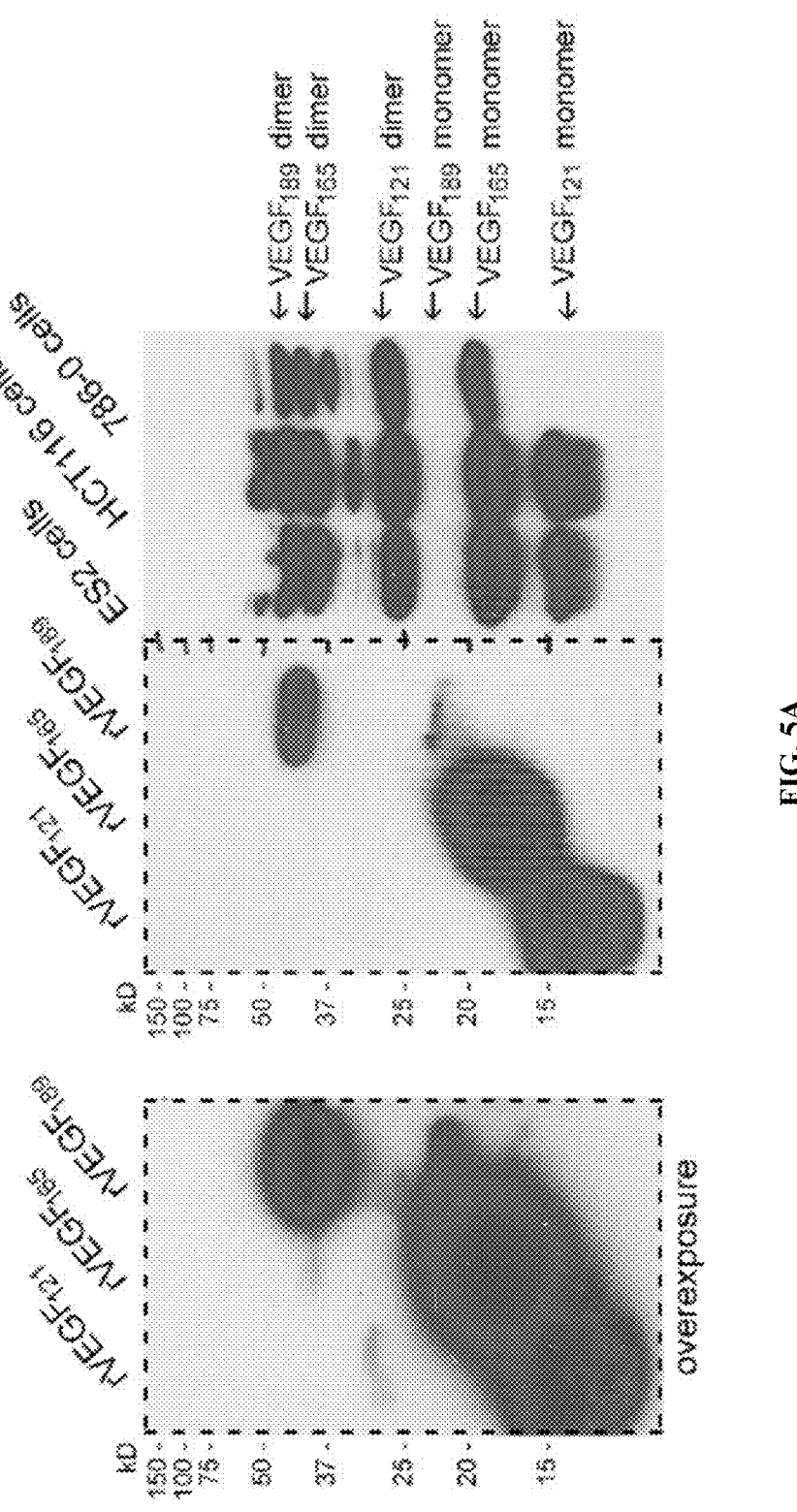
FIGS. 5A-5D. sENT-VEGF predominantly comprises of dimeric VEGF$_{189}$.
Figure 5B:
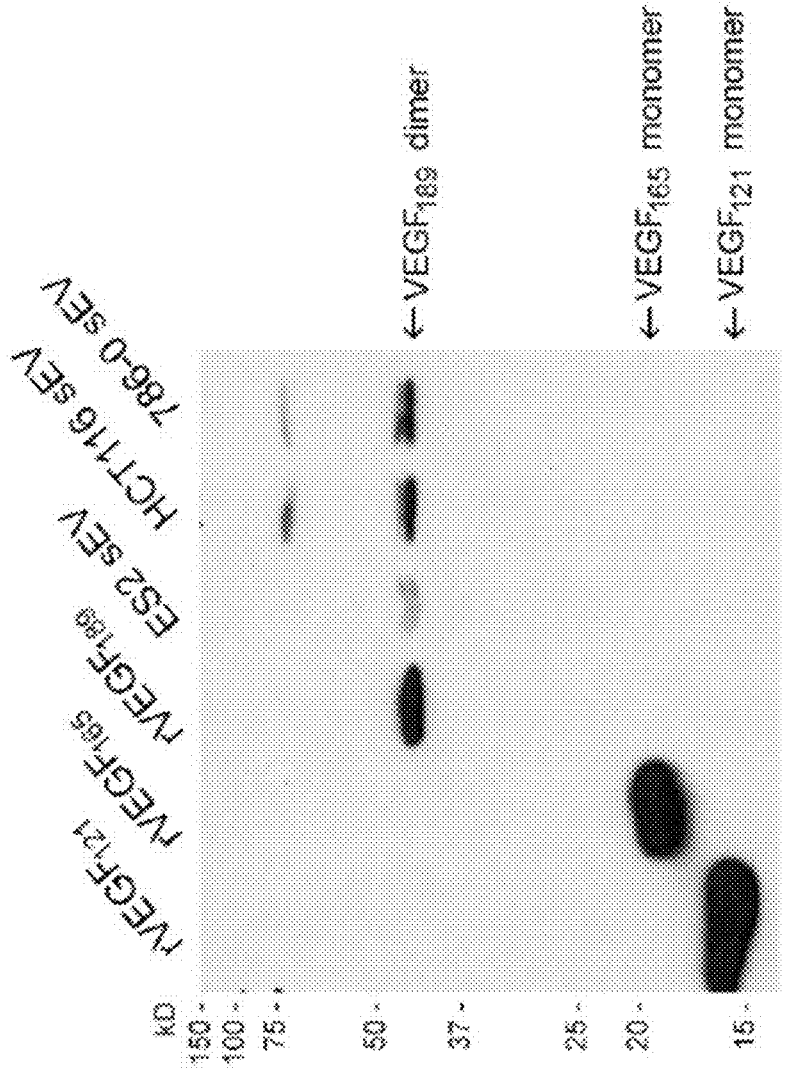
Figure 5C:
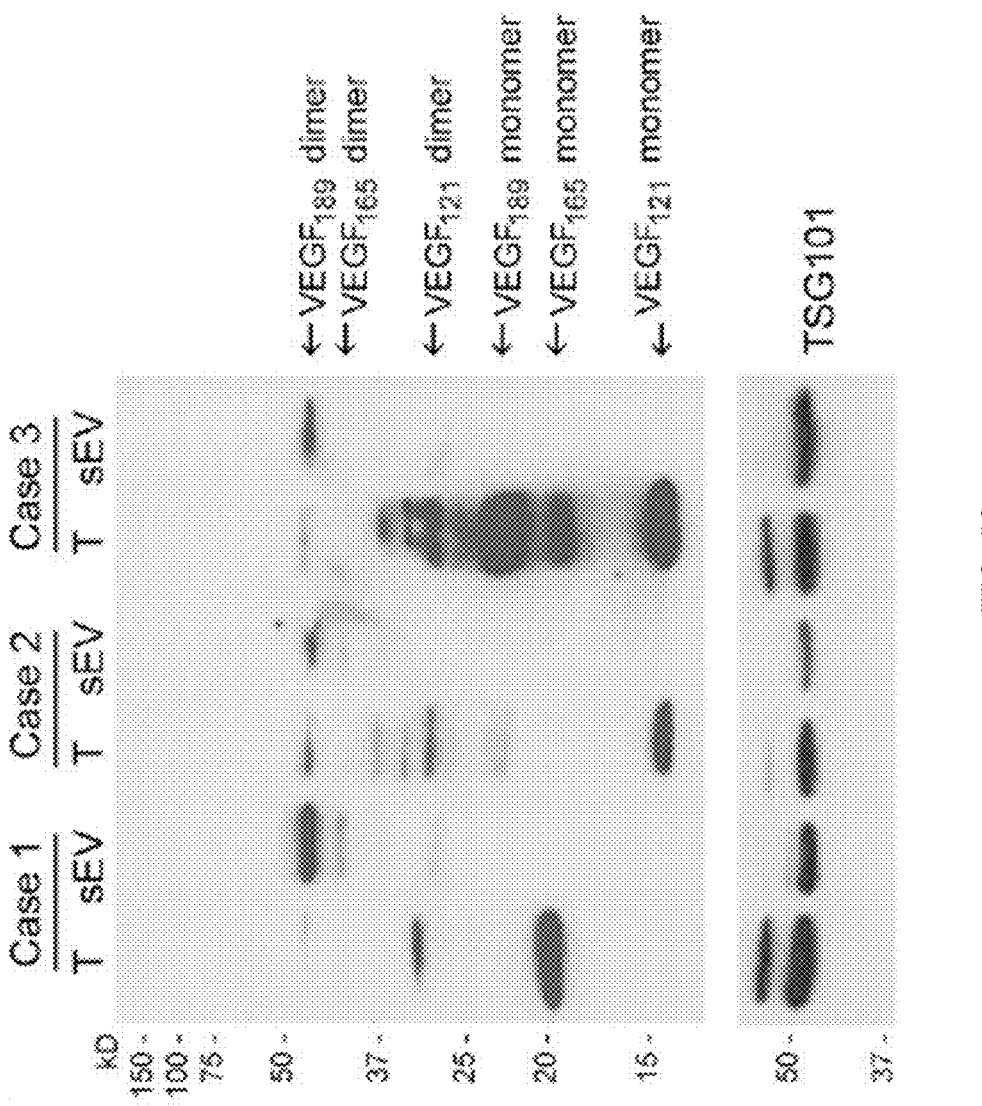
Figure 5D:
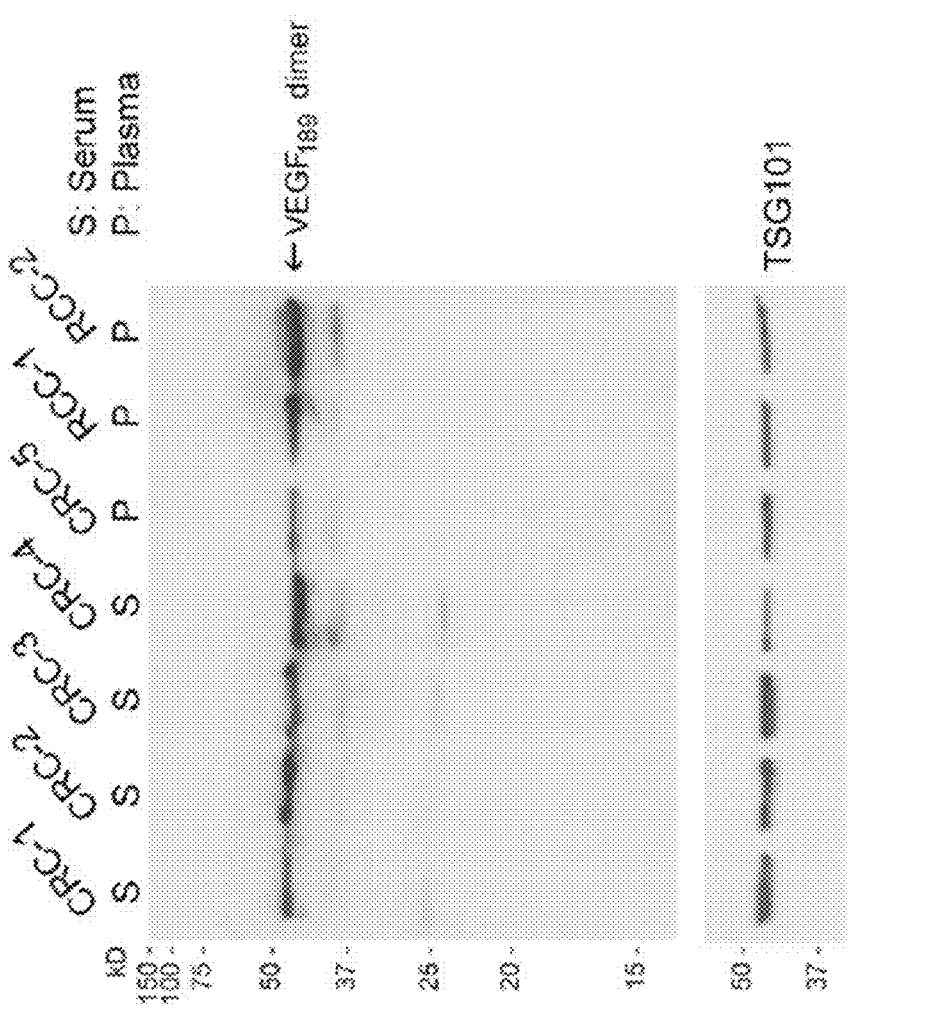

Herein, it is shown that cancer cell-derived sEVs can stimulate endothelial cell migration and tube formation independently of uptake, and that these responses are mediated by heparin-bound VEGF on the surface of sEVs. These findings that sEV-VEGF is signaling-competent is consistent with a report that heparin-bound VEGF can activate VEGFR2 phosphorylation and that this activation does not require VEGF internalization (Anderson et at, 2011), It is increasingly recognized that the molecular composition of sEVs is distinct from the cellular profile (Xu et al., 2018), but little is known as to whether and how highly related proteins are differentially localized to sEVs. The present study shows that sEV-VEGF predominantly comprises $VEGF_{189}$ in its active dimeric form and that $VEGF_{189}$, but not two other major isoforms ($VEGF_{121}$ and $VEGF_{165}$), preferentially localizes to sEVs. $VEGF_{189}$ has substantially higher affinity for heparin than $VEGF_{165}$, and $VEGF_{121}$ does not bind heparin (Ferrara et al., 2003). The notion that $VEGF_{189}$ preferentially localizes to sEVs, at least in part, because of its high affinity for heparin is supported by the present findings that the $VEGF_{189}$ content is substantially reduced in sEVs of cells that are deficient in heparan sulfate biosynthesis and that heparinase removes $VEGF_{189}$ from the surface of sEVs (FIGS. 6E-G). Although $VEGF_{189}$ can bind to sEVs post-secretion, post-secretion binding only partially explained the presence of $VEGF_{189}$ in sEVs (FIG. 6D). Intriguingly, Feng and colleagues identified that breast cancer cell-derived large EVs (lEV) of 0.5 to 1.0 μm in diameter contain a 90 kD form of VEGF ($VEGF_{90K}$) that comprises of crosslinked $VEGF_{165}$ bound to heat shock protein 90 (Feng et al., 2017). Notably, the authors neither detected other forms of VEGF in lEVs nor detected $VEGF_{90K}$ in breast cancer sEVs (Feng et al., 2017). Similarly, the present studies did not detect $VEGF_{90K}$ in sEVs isolated from other cancer cell types and from body fluids of cancer patients (FIGS. 5B-D). The differences between the present findings in sEVs and those of Feng and colleagues in lEVs implicate that different isoforms of VEGF are sorted by distinct mechanisms, resulting in compartmentalization into different types of EVs.

Figure 2A:
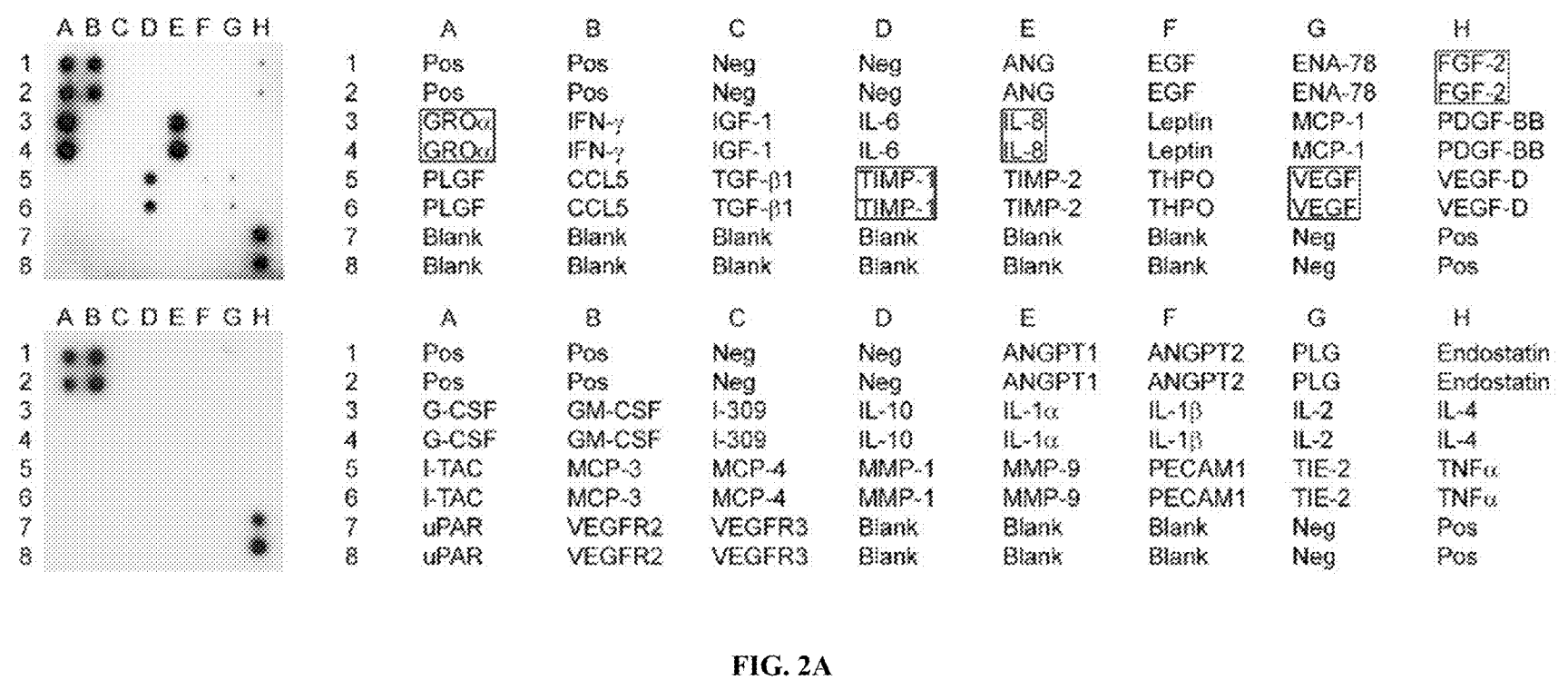
Figure 2B:
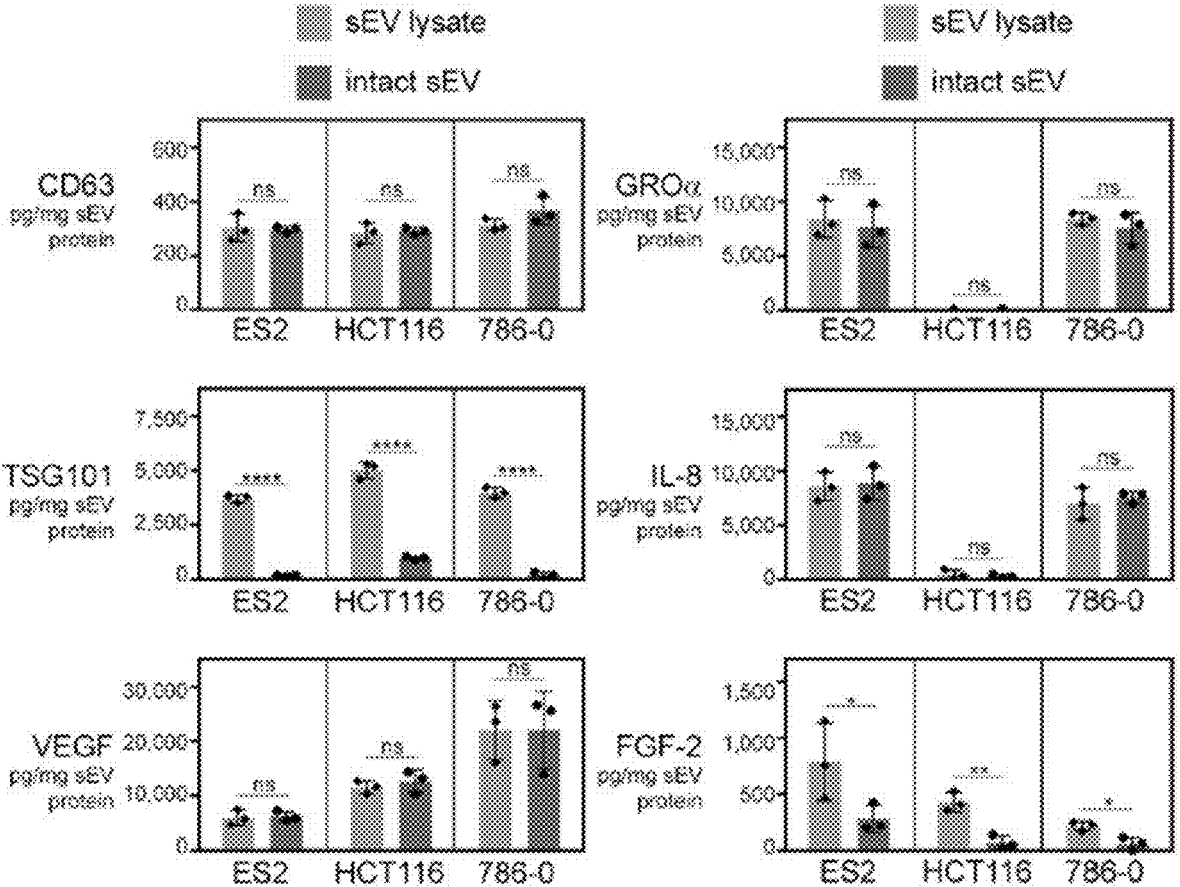

The finding that VEGF associates with the sEV surface via heparin-binding raises the possibility that other growth factors that bind heparin, such as GROα, IL-8 and FGF-2 (Wang et al., 2003; Spillmann et al., 1998; Rapraeger et al., 1991), are similarly localized. The present studies detected GROα and IL-8 in sEVs of some cancer cell lines and these ligands mostly localized on the surface (FIG. 2B). In contrast, most of the FGF-2 detected in sEVs was not surface-associated (FIG. 2B), This finding might be explained by the non-classical secretion of FGF-2. Whereas many other growth factors undergo endoplasmic reticulum-to-Golgi trafficking, FGF-2 lacks a signal peptide and is instead recruited to the inner leaflet of the plasma membrane (La Venuta et al., 2015). Once there, FGF-2 undergoes oligomerization that in turn causes formation of membrane pores, enabling FGF-2 to cross the membrane (La Venuta et al., 2015). FGF-2 is also released from cells in ectosomes that bud from the plasma membrane and range from 100 to 1000 nm in diameter (Taverna et al., 2003). It is possible that the present sEV preparations not only included exosomes but also small ectosomes. The formation of ectosomes through outward budding of the plasma membrane could explain why FGF-2 is encapsulated in these EVs rather than located on the EV surface.

Figure 15A:
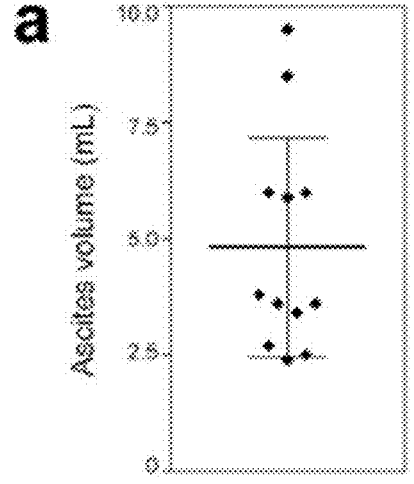
FIGS. 15A-15B. Levels of tumor-derived and stroma-derived sEV-VEGF in the parental ES2 xenograft model. Ascites was collected from female nude mice (n=12) at 3 weeks following i.p. injection of parental (i.e. VEGF$^{+/+}$) ES2 cells.
Figure 15B:
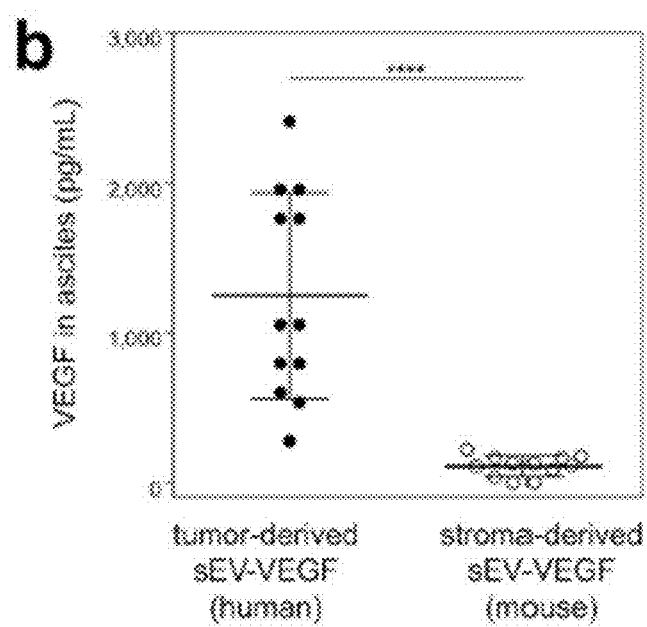

Although functions of sEV cargo have been increasingly studied, the physiological relevance of levels of many of these constituents is unclear. sEV-VEGF constituted one-third of the total VEGF secreted by cancer cells that were presently analyzed (FIG. 3F) and up to one-third of the total VEGF in ascites of mice and women with ovarian cancer (Table 1). Furthermore, analysis of xenograft models indicated that almost all sEV-VEGF was tumor-derived (FIG. 15B). Although several growth factors have been detected in cancer-derived sEVs (Skog et al., 2008), it has been unclear as to whether vesicular localization alters properties of the ligands. VEGF has a short half-life, as is the case for most growth factors (Eppler et al., 2002). Notably, interaction of $VEGF_{189}$ with the surface of sEVs profoundly increases ligand half-life (FIG. 611). It has been thought that $VEGF_{189}$, by virtue of being membrane/matrix-bound, acts locally whereas $VEGF_{121}$, by virtue being freely secreted, mediates long-range signaling (Ferrara; 2010). That sEV-VEGF predominantly comprises $VEGF_{189}$ and is signaling-competent, highly stable and present in the peripheral circulation of tumor-bearing mice and cancer patients collectively support the possibility that $VEGF_{189}$, through being conveyed on secreted sEVs, also mediates long-range signaling. Additional long-range signaling, mediated by sEV-VEGF, might provide a strong advantage to tumors and particularly for metastasis.

Figures 7A, 7B:
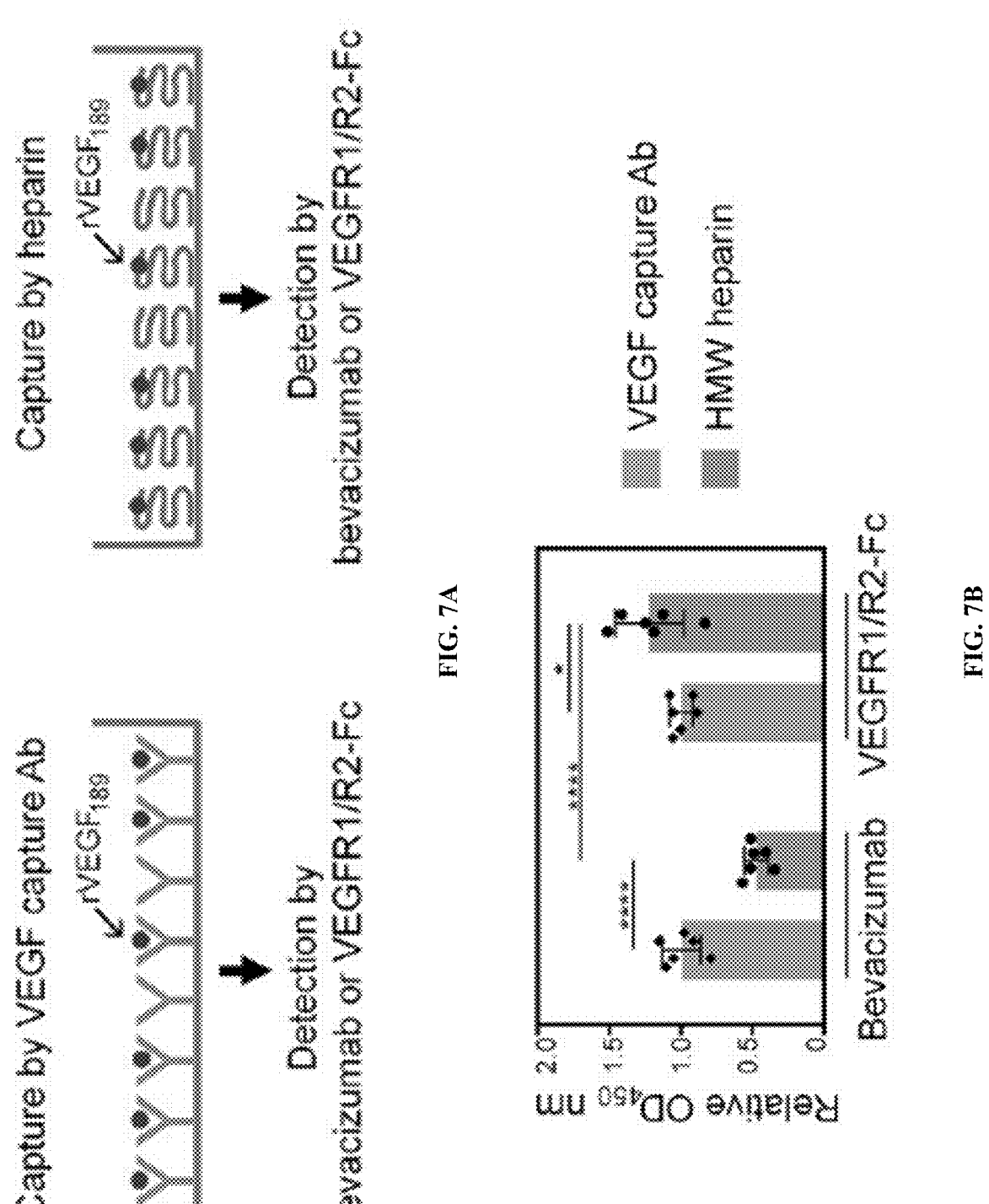
FIGS. 7A-7H. Heparin-bound sEV-VEGF is not neutralized by bevacizumab in vitro.

Another significant outcome of the finding that cancer cell-derived sEVs contain heparin-bound, signaling-competent VEGF is the impact on responsiveness of tumors to bevacizumab. Bevacizumab was initially approved for treatment of metastatic colorectal cancer and subsequently approved for several other solid tumors including ovarian cancer and metastatic renal cell carcinoma (Ferrara et al., 2005; Cao et al., 2011). However, the clinical benefit of bevacizumab has not been as promising as first expected and its approval for treatment of metastatic breast cancer was withdrawn due to modest benefits and significant adverse effects (Twine, 2011). Resistance of tumors to anti-VEGF therapy has been attributed to several mechanisms that are independent of VEGF signaling. These include the utilization by tumors of existing vasculature (Frentzas et al., 2016), and of alternative angiogenic pathways such as those mediated by Bv8 which is secreted by infiltrating myeloid cells (Shojaei et al., 2007) and by adipose tissue-derived IL-6 and FGF-2 (Incio et al., 2018). Resistance to anti-VEGF therapy has also been attributed to hypoxia-triggered metabolic reprogramming and increased uptake of free fatty acid that fuels tumor growth (Iwamoto et al., 2018). Poor outcomes can also stem from effects of anti-VEGF therapy on the endocrine system (Cao, 2014). The present finding that sEV-VEGF is not neutralized by bevacizumab implicate that resistance to bevacizumab might also stem in part from the failure of this agent to recognize its target molecule. Bevacizumab has been thought to neutralize all isoforms of VEGF, but prior studies have largely focused on characterizing the binding of this agent to soluble VEGF. Several residues in the β5-sheet, β5-β6 loop and β6-sheet of VEGF are critical for forming a high-affinity complex with bevacizumab (Muller et al., 1998). Intriguingly, interaction of VEGF with HMW heparin substantially decreases the β-sheet content of VEGF and increases its α-helix content (Wijelath et al., 2010). Binding of bevacizumab to $VEGF_{189}$ was substantially reduced when $VEGF_{189}$ was engaged with HMW heparin (FIG. 7B). The inability of bevacizumab to neutralize sEV-VEGF might therefore stem; at least in part, from conformational change in this ligand that is induced through its interaction with heparin.

Figures 8A, 8B:
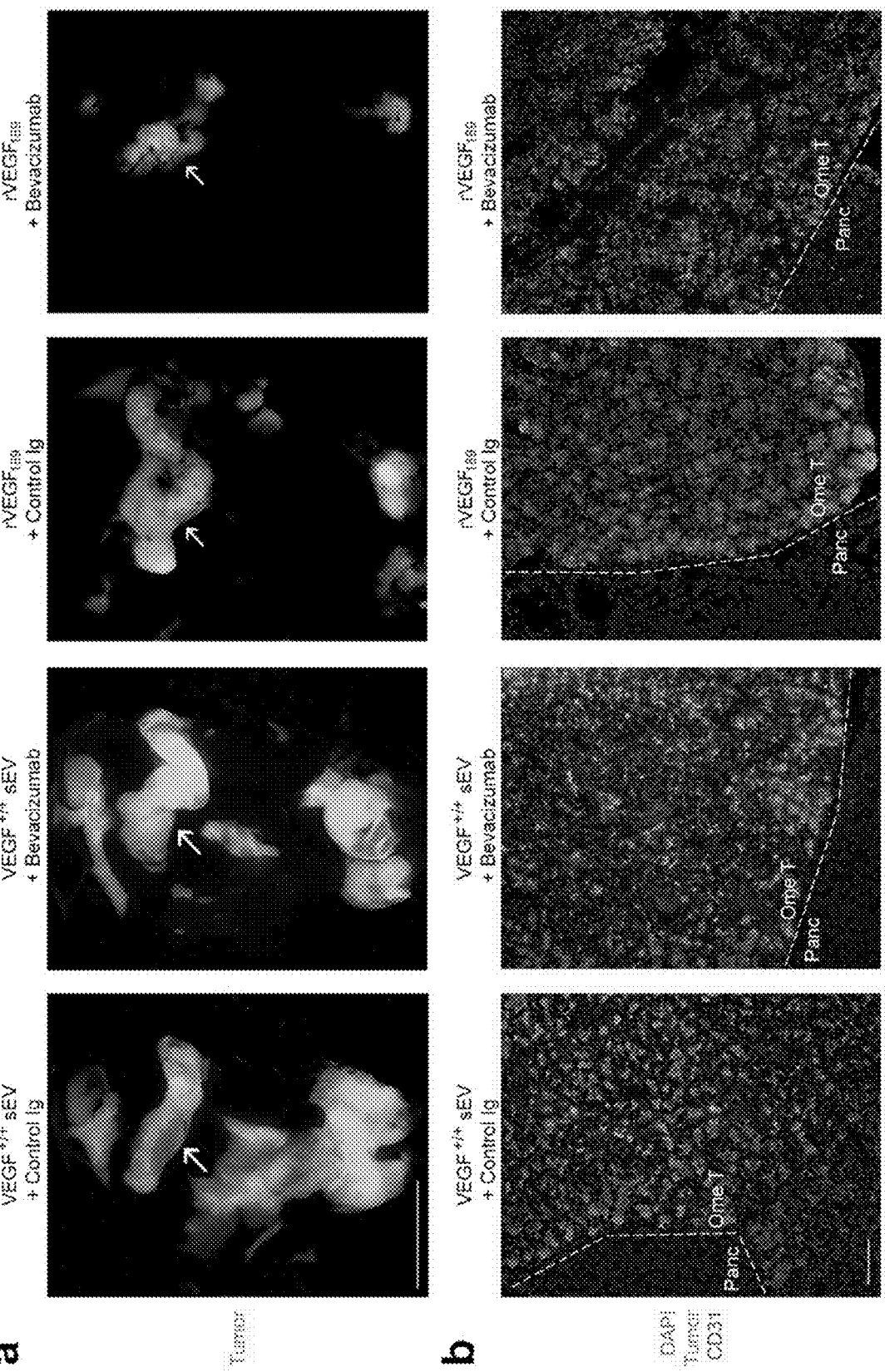
FIGS. 8A-8G. sEV-VEGF is not neutralized by bevacizumab in vivo and is associated with disease progression in bevacizumab-treated cancer patients.
Figures 8C, 8D, 8E, 8F, 8G:
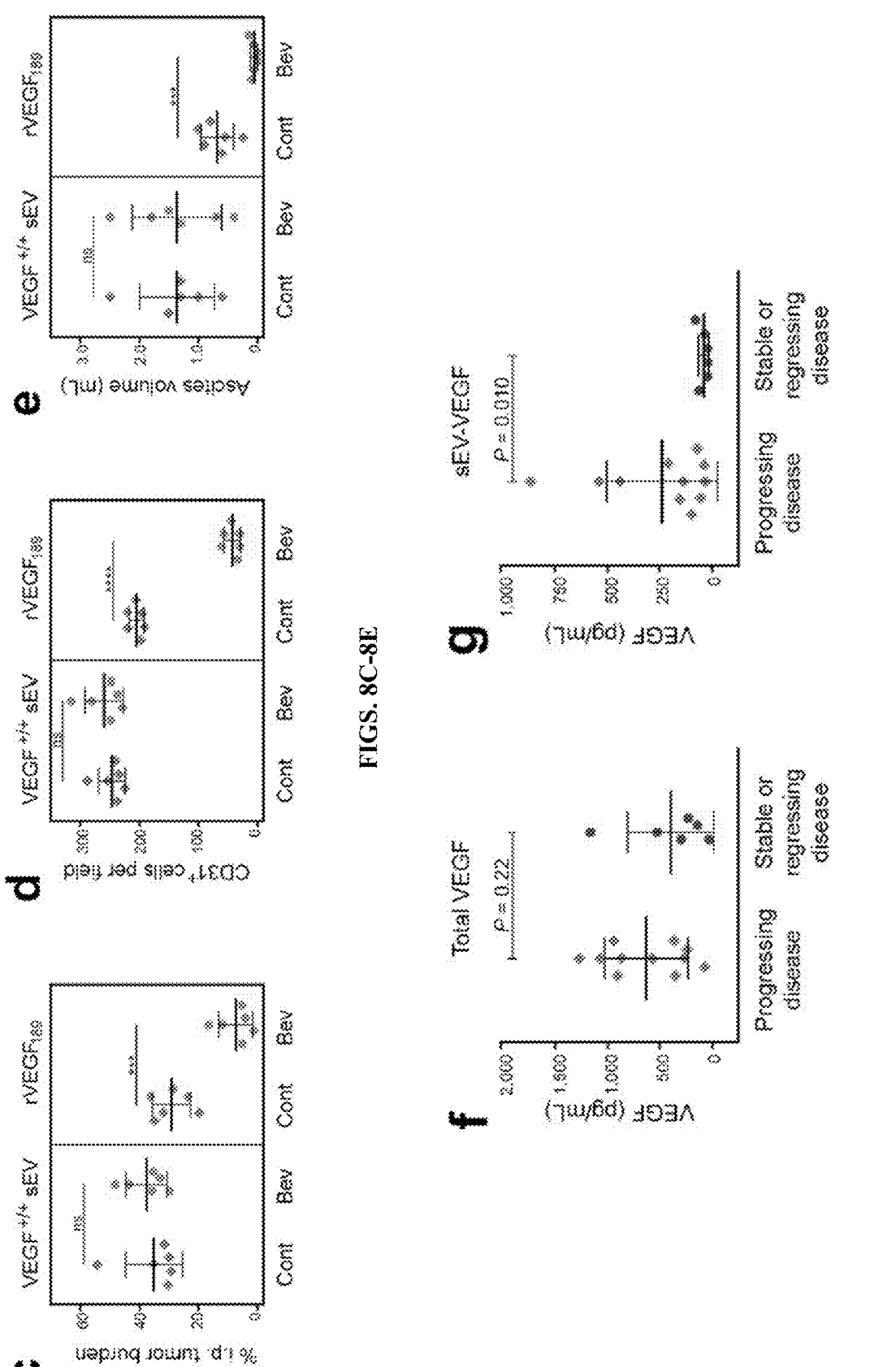

A limitation of bevacizumab has been the lack of robust biomarkers that can predict clinical response (Cao et al., 2011; Lambrechts et al., 2013). Whereas some studies have found that baseline plasma levels of total VEGF correlate with outcomes following bevacizumab treatment (Van Cutsem et al., 2012; Mok et al., 2014), there are several other reports that baseline levels of total VEGF are not predictive of bevacizumab treatment benefit (Lambrechts et al., 2013; Hodge et al., 2013; Miles et al., 2017). In an independent cohort of patients with renal cell carcinoma who received bevacizumab monotherapy, no significant difference in baseline levels of total VEGF was found between patients who had progressing disease and those who had stable or regressing disease (FIG. 8F). In contrast, baseline levels of sEV-VEGF were approximately 5-fold higher in patients with progressing disease than in those with stable or regressing disease (FIG. 8G). Intriguingly, 1EV-associated $VEGF_{90K}$ has also been found to be bevacizumab-insensitive (Feng et al., 2017). However, it is as yet unclear whether this form of VEGF is present in body fluids of cancer patients and to what extent it contributes to the total circulating VEGF.

In summary, the present study shows that $VEGF_{189}$, but not two other major isoforms of VEGF, is selectively enriched in cancer cell-derived sEVs, associates with the surface of sEVs via heparin-binding, and can be delivered in signaling-competent form by sEVs to endothelial cells independently of EV uptake. The present study also shows that interaction of $VEGF_{189}$ with the surface of sEVs profoundly increases ligand half-life, and that sEV-VEGF is not neutralized by bevacizumab. These findings implicate that resistance of tumors to bevacizumab might stem in part from the ability of cancer cell-derived sEVs to deliver biologically active VEGF to recipient cells without being recognized by the neutralizing agent. These findings suggest that baseline levels of sEV-VEGF might be more informative for bevacizumab treatment benefit than levels of total VEGF. Furthermore, the present findings that the activity of sEV-VEGF can be blocked by VEGFR tyrosine kinase inhibitors or VEGFR2 neutralizing Ab raise the possibility that treatment with these inhibitors rather than bevacizumab might be beneficial for patients who have elevated sEV-VEGF levels.

II. SMALL EXTRACELLULAR VESICLES (SEVS)

It is widely recognized that the tumor microenvironment is modulated by cancer cells to support tumorigenesis and that this stromal reprogramming is coordinated by direct cell-to-cell contact and/or soluble factors Manahan & Weinberg, 2011). A classic example of this phenomenon is the orchestration by cancer-derived factors of endothelial cell growth, migration and assembly into vessels that in turn supply oxygen and nutrients to sustain tumor growth (Hanahan & Weinberg, 2011). Increasing evidence indicates that stromal reprogramming is also coordinated by extracellular vesicles (EVs) secreted by cancer cells. EVs are membranous structures that encapsulate biomolecular cargo such as RNA and proteins, and are often more highly secreted by cancer cells than by normal cells (Xu et al., 2018). EVs vary in size and biogenesis. EVs include apoptotic bodies that are typically 1 to 5 μm in diameter, and ectosomes that form through budding of the plasma membrane and range from 100 to 1000 nm in diameter (Xu et al., 2018; Thery et al., 2018). Exosomes are EVs that derive from multivesicular endosomes and range from 30 to 150 nm in diameter (Xu et al., 2018; Thery et al, 2018). Because of the difficulty in defining the sub-cellular origin of an EV, a size-based EV nomenclature has been recommended (Thery et al., 2018). The most studied type of EV are small EVs (sEVs) that are less than 200 nm in diameter (Thery et al., 2018). sEVs that are secreted by cancer cells can suppress immune cell function (Muller et al., 2016; Chen et al., 2018), and induce fibroblasts and mesenchymal stem cells to acquire an inflammatory phenotype (Fang et al., 2018; Paggetti et al., 2015). Furthermore, several studies have shown that cancer cell-derived sEVs stimulate endothelial cell migration and vessel formation (Paggetti et al., 2015; Skog et al., 2008; Zhou et al., 2014; Hsu et al., 2017).

In a number of studies, the biological responses to sEVs have been attributed to constituents of their luminal cargo; such as microRNAs, and the activity of these constituents is contingent upon uptake of sEVs by recipient cells (Fang et al., 2018; Paggetti et al., 2015; Skog et al., 2008; Zhou et al., 2014; Hsu et al., 2017). However, the significance of sEV-mediated RNA transfer has been questioned by studies that analyzed the stoichiometry of microRNAs and sEVs and the fate of sEV RNA in recipient cells (Chevillet et al., 2014; Kanada et al., 2015). Furthermore, there is evidence that sEVs can deliver signals to various immune cells independently of uptake (Muller et al., 2016; Segura et al., 2007). These findings suggest that sEVs might mediate intercellular communication in the tumor microenvironment through mechanisms other than transferring their luminal cargo into recipient cells.

The term "small extracellular vesicles" (sEVs) encompasses extracellular vesicles that are less than 200 nm diameter and includes exosomes.

III. METHODS OF TREATMENT AND METHODS OF DETECTION

The present invention provides methods of selecting a treatment for a disease patient as well as methods of treating a patient with a disease with the selected treatment. The disease may be a cancer. Alternatively, the disease may be any disease for which bevacizumab or derivatives of bevacizumab are used as treatment, such as, for example, eye diseases (e.g., macular degeneration and/or retinal edema). The methods involve determining the level of small extracellular vesicle (sEV)-associated VEGF (henceforth termed sEV-VEGF) in the patient. The treatment for the patient is determined based on the level of sEV-VEGF in the patient. Patients with higher levels of sEV-VEGF are more likely to be non-responsive to treatment with bevacizumab. As such, those patients are selected for treatment with a VEGFR tyrosine kinase inhibitor, a VEGFR2 neutralizing antibody, or a VEGF ligand trap. A higher level of sEV-VEGF may be a level that is elevated relative to a level seen in patients with cancer that is stable or regressive. On the other hand, patients with lower levels of sEV-VEGF are more likely to respond to treatment with bevacizumab. As such, those patients are selected for treatment with bevacizumab.

VEGFR tyrosine kinase inhibitors include, for example, axitinib, sunitinib, cabozantinib, pazopanib, sorafenib, cediranib, tivozanib, lenvatinib, motesanib, ponatinib, regorafenib, vandetanib, ZM323881, GW654652, GW612286, GW695612, SU5416, SU1498, SU6668, SU5402, and PTK787/ZK222584, VECiFR2 neutralizing antibodies include, for example, MAB3572 or a humanized version of MAB357, DC101 or a humanized version of DC101, and AF357 or a humanized version of AF357. The term "VEGF ligand trap" as used herein means a protein, such as a fusion molecule, that binds to VEGF and is capable of neutralizing, blocking, inhibiting, abrogating, reducing or interfering with VEGF activities. A VEGF ligand trap may include a fusion of two VEGF binding domains (e.g., VEGFR1 domain 2, VEGFR2 domain 3) that prevent VEGF from binding to VEGF receptors. VEGF ligand traps include, for example, aflibercept.

Such treatment may also be in combination with another therapeutic regime, such as chemotherapy or immunotherapy. The classification of a given cancer may change over time as well, such that the present methods regarding selecting an appropriate treatment will need to be performed more than once, such as repeating the methods during the course of treatment with bevacizumab.

A. Detection

In some aspects, the present disclosure concerns methods for detecting the level of sEV-VEGF in a patient. Alternative, as discussed further in Example 11, the level of sEV-VEGF can be approximated without having to isolate sEVs. This is done by performing parallel immunoassays one to detect the amount of VEGF in the sample that binds to bevacizumab and a second to detect that amount of VEGF in the sample that binds to VEGF receptors (e.g., using VEGFR1/R2-Fc). Then the amount of bevacizumab-bound VEGF is subtracted from the amount of receptor-bound VEGF to determine an amount of VEGF that cannot be neutralized by bevacizumab, which approximates the level of sEV-VEGF.

A wide variety of assay formats are contemplated for detecting protein products, including immunohistochemistry, enzyme linked immunosorbent assay (ELISA), radioimmunoassay (RIA), immunoradiometric assay, fluoroimmunoassay, chemiluminescent assay, bioluminescent assay, dot blotting, FACS analyses, and Western blot to mention a few. The steps of various useful immunodetection methods have been described in the scientific literature. In general, the immunobinding methods include obtaining a sample to be tested, and contacting the sample with an antibody specific for the protein to be detected (i.e., VEGF), as the case may be, under conditions effective to allow the formation of immunocomplexes. In general, the detection of immunocomplex formation is well known in the art and may be achieved through the application of numerous approaches. These methods are generally based upon the detection of a label or marker, such as any of those radioactive, fluorescent, biological and enzymatic tags. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

As used herein, the term "sample" refers to any sample suitable for the detection methods provided by the present invention. The sample may be any sample that includes material suitable for detection or isolation. Sources of samples include blood, pleural fluid, peritoneal fluid, urine, saliva, malignant ascites, broncho-alveolar lavage fluid, synovial and bronchial washes. In one aspect, the sample is a blood sample, including, for example, whole blood or any fraction or component thereof. A blood sample suitable for use with the present invention may be extracted from any source known that includes blood cells or components thereof, such as venous, arterial, peripheral, tissue, cord, and the like. For example, a sample may be obtained and processed using well-known and routine clinical methods (e.g., procedures for drawing and processing whole blood). In one aspect, an exemplary sample may be peripheral blood drawn from a subject with cancer. In some aspects, the biological sample comprises a plurality of cells. In certain aspects, the biological sample comprises fresh or frozen tissue. In specific aspects, the biological sample comprises formalin fixed, paraffin embedded tissue. In some aspects, the biological sample is a tissue biopsy, fine needle aspirate, nipple aspirate, blood, serum, plasma, cerebral spinal fluid, urine, stool, saliva, circulating tumor cells, exosomes, or aspirates and bodily secretions, such as sweat.

B. Treatment

The term "subject" or "patient" as used herein refers to any individual to which the subject methods are performed. Generally the patient is human, although as will be appreciated by those in the art, the patient may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of patient.

"Treatment" and "treating" refer to administration or application of a therapeutic agent to a subject or performance of a procedure or modality on a subject for the purpose of obtaining a therapeutic benefit of a disease or health-related condition. For example, a treatment may include administration chemotherapy, immunotherapy, radiotherapy, performance of surgery, or any combination thereof.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example; treatment of cancer may involve, for example, a reduction in the invasiveness of a tumor, reduction in the growth rate of the cancer, or prevention of metastasis. Treatment of cancer may also refer to prolonging survival of a subject with cancer.

Likewise, an effective response of a patient or a patient's "responsiveness" to treatment refers to the clinical or therapeutic benefit imparted to a patient at risk for, or suffering from, a disease or disorder. Such benefit may include cellular or biological responses, a complete response, a partial response, a stable disease (without progression or relapse), or a response with a later relapse. For example, an effective response can be reduced tumor size or progression-free survival in a patient diagnosed with cancer.

The term "cancer," as used herein, may be used to describe a solid tumor, metastatic cancer, or non-metastatic cancer. In certain embodiments, the cancer may originate in the bladder, blood, bone, bone marrow, brain, breast, colon, esophagus, duodenum, small intestine, large intestine, colon; rectum, anus, gum, head, kidney, liver, lung, nasopharynx, neck, ovary, pancreas, prostate, skin, stomach, testis, tongue, or uterus.

The cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchioloalveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; pagers disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor; malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. Nonetheless, it is also recognized that the present invention may also be used to treat a non-cancerous disease (e.g., a fungal infection, a bacterial infection, a viral infection, a neurodegenerative disease, and/or a genetic disorder).

Regarding neoplastic condition treatment, depending on the stage of the neoplastic condition, neoplastic condition treatment involves one or a combination of the following therapies: surgery to remove the neoplastic tissue, radiation therapy, and chemotherapy. Other therapeutic regimens may be combined with the administration of the anticancer agents, e.g., therapeutic compositions and chemotherapeutic agents. For example, the patient to be treated with such anti-cancer agents may also receive radiation therapy and/or may undergo surgery.

For the treatment of disease, the appropriate dosage of a therapeutic composition will depend on the type of disease to be treated, as defined above, the severity and course of the disease, previous therapy, the patient's clinical history and response to the agent, and the discretion of the physician. The agent may be suitably administered to the patient at one time or over a series of treatments.

C. Combination Therapy

The methods and compositions, including combination therapies, enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. A tissue, tumor, or cell can be contacted with one or more compositions or pharmacological formulation(s) comprising one or more of the agents or by contacting the tissue, tumor, and/or cell with two or more distinct compositions or formulations. Also, it is contemplated that such a combination therapy can be used in conjunction with radiotherapy, surgical therapy, or immunotherapy.

Administration in combination can include simultaneous administration of two or more agents in the same dosage form, simultaneous administration in separate dosage forms, and separate administration. That is, the subject therapeutic composition and another therapeutic agent can be formulated together in the same dosage form and administered simultaneously. Alternatively, subject therapeutic composition and another therapeutic agent can be simultaneously administered, wherein both the agents are present in separate formulations. In another alternative, the therapeutic agent can be administered just followed by the other therapeutic agent or vice versa. In the separate administration protocol, the subject therapeutic composition and another therapeutic agent may be administered a few minutes apart, or a few hours apart, or a few days apart.

An anti-cancer first treatment may be administered before, during, after, or in various combinations relative to a second anti-cancer treatment. The administrations may be in intervals ranging from concurrently to minutes to days to weeks. In embodiments where the first treatment is provided to a patient separately from the second treatment, one would generally ensure that a significant period of time did not expire between the time of each delivery, such that the two compounds would still be able to exert an advantageously combined effect on the patient, in such instances, it is contemplated that one may provide a patient with the first therapy and the second therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

In certain embodiments, a course of treatment will last 1-90 days or more (this such range includes intervening days). It is contemplated that one agent may be given on any day of day 1 to day 90 (this such range includes intervening days) or any combination thereof, and another agent is given on any day of day 1 to day 90 (this such range includes intervening days) or any combination thereof. Within a single day (24-hour period), the patient may be given one or multiple administrations of the agent(s). Moreover, after a course of treatment, it is contemplated that there is a period of time at which no anti-cancer treatment is administered. This time period may last 1-7 days, and/or 1-5 weeks, and/or 1-12 months or more (this such range includes intervening days), depending on the condition of the patient, such as their prognosis, strength, health, etc. It is expected that the treatment cycles would be repeated as necessary.

Various combinations may be employed. For the example below a subtype-specific anti-cancer therapy is "A" and another anti-cancer therapy is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/AA/A A/B/A/A A/A/B/A

Administration of any compound or therapy of the present invention to a patient will follow general protocols for the administration of such compounds, taking into account the toxicity, if any, of the agents. Therefore, in some embodiments there is a step of monitoring toxicity that is attributable to combination therapy.

1. Chemotherapy

A wide variety of chemotherapeutic agents may be used in accordance with the present invention. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, Or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carhoquone, meturedopa, and uredopa; ethylenimines and methylamelamines, including altretamine, triethylenemelamine, trietyl enephosphoramide, triethiylenethiophosphoramide, and trimethylolomel amine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocartnycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estratnustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaII and calicheamicin omegaII); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin); epirubicin, esorubicin, idarubicin, marcellomycin, mitomycins, such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, and zorubicin; antimetabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine; 6-azauridine, carmofur; cytarabine; dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as folinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor US 2000; difluoromethylornithine (MEM); retinoids, such as retinoic acid; capecitabine; PARP inhibitors, such as olaparib, rucaparib, niraparib; talazoparib, BMN673, iniparib, CEP 9722, or ABT888 (veliparab); CDK4/6 inhibitors, such as ribociclib, ademaciclib, or trilaciclib; androgen inhibitor and antiandrogens, such as cyproterone acetate; megestrol acetate, chlormadinone acetate, spironolactone, oxendolone, osaterone acetate, flutamide; bicalutamide, nilutamide, topilutamide, enzalutamide, apalutamide, dienogest, drospirenone, medrogestone, nomegestrol acetate, promegestone, trimegeston, ketoconazole, abiraterone acetate, seviteronel, aminoglutethimide, finasteride, dutasteride, epristeride, alfatradiol, saw palmetto extract (Serenoa repens), medrogestone, and bifluranol; carboplatin, procarbazine, plicomycin, gemcitabien, navelbine, farnesyl-protein tansferase inhibitors, transplatinum, and pharmaceutically acceptable salts, acids, or derivatives of any of the above.

2. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted; and the uptake by the neoplastic cells.

3. Immunotherapy

The skilled artisan will understand that immunotherapies may be used in combination or in conjunction with methods of the embodiments. In the context of cancer treatment, immunotherapeutics, generally, rely on the use of immune effector cells and molecules to target and destroy cancer cells. Rituximab (RITUXAN®) is such an example. The immune effector may be; for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2; IL-4, IL-12; GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis, Plasmodium falciparum*, dinitrochlorobenzene, and aromatic compounds (U.S. Pat. Nos. 5,801,005 and 5,739, 169; Hui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNT, IL-1, Th-2, and p53 (Qin et al., 1998; Austin-Ward and Villaseca; 1998; U.S. Pat. Nos. 5,830,880 and 5,846,945); and monoclonal antibodies; e.g.; anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

In some embodiments, the immunotherapy may be an immune checkpoint inhibitor. Immune checkpoints either turn up a signal (e.g., co-stimulatory molecules) or turn down a signal. Immune checkpoints either turn up a signal (e.g., co-stimulatory molecules) or turn down a signal. Immune checkpoint proteins that may be targeted by immune checkpoint blockade include adenosine A2A receptor (A2AR), B7-H3 (also known as CD276), B and T lymphocyte attenuator (BMA); CCL5, CD27, CD38, CD8A, CMKLR1, cytotoxic T-lymphocyte-associated protein 4 (CTLA-4, also known as CD152), CXCL9; CXCR5, glucocorticoid-induced tumour necrosis factor receptor-related protein (GITR), HLA-DRB1, ICOS (also known as CD278), HLA-DQA1, HLA-E, indoleamine 2,3-dioxygenase 1 (IDO1), immunoglobulin (KIR), lymphocyte activation gene-3 (LAG-3, also known as CD223), Mer tyrosine kinase (MerTK), NKG7, OX40 (also known as CD134), programmed death 1 (PD-1), programmed death-ligand 1 (PD-L1, also known as CD274), PDCD1LG2, PSMB10; STAT1, T cell immunoreceptor with Ig and ITIM. domains (TIGIT), T-cell immunoglobulin domain and mucin domain 3 (TIM-3), V-domain Ig suppressor of T cell activation (VISTA, also known as C10orf54); and 4-1BB (CD137). In particular, the immune checkpoint inhibitors target the PD-1 axis and/or CTLA-4.

The immune checkpoint inhibitors may be drugs, such as small molecules, recombinant forms of ligand or receptors, or antibodies, such as human antibodies (e.g., International Patent Publication WO2015/016718; Pardoll, *Nat Rev Cancer*, 12(4): 252-264, 2012; both incorporated herein by reference). Known inhibitors of the immune checkpoint proteins or analogs thereof may be used, in particular chimerized, humanized, or human forms of antibodies may be used. As the skilled person will know, alternative and/or equivalent names may be in use for certain antibodies mentioned in the present disclosure. Such alternative and/or equivalent names are interchangeable in the context of the present disclosure. For example, it is known that lambrolizumab is also known under the alternative and equivalent names MK-3475 and pembrolizumab.

In some embodiments, a PD-1 binding antagonist is a molecule that inhibits the binding of PD-1 to its ligand binding partners. In a specific aspect, the PD-1 ligand binding partners are PD-L1 and/or PD-L2. In another embodiment, a PD-L1 binding antagonist is a molecule that inhibits the binding of PD-L1 to its binding partners. In a specific aspect, PD-L1 binding partners are PD-1 and/or B7-1. In another embodiment, a PD-L2 binding antagonist is a molecule that inhibits the binding of PD-L2 to its binding partners. In a specific aspect, a PD-L2 binding partner is PD-1. The antagonist may be an antibody, an antigen binding fragment thereof, an immunoadhesin, a fusion protein, or an oligopeptide. Exemplary antibodies are described in U.S. Pat. Nos. 8,735,553, 8,354,509, and 8,008,449, all of which are incorporated herein by reference. Other PD-1 axis antagonists for use in the methods provided herein are known in the art, such as described in U.S. Patent Application Publication Nos. 2014/0294898, 2014/022021, and 2011/0008369, all of which are incorporated herein by reference.

In some embodiments, a PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the PD-1 binding antagonist is an immunoadhesin (e.g., an immunoadhesin comprising an extracellular or RD-1 binding portion of PD-L1 or PD-L2 fused to a constant region (e.g., an Fc region of an immunoglobulin sequence)). In some embodiments, the PD-1 binding antagonist is AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, is an anti-PD-1 antibody, described in WO2009/114335. CT-OH, also known as hBAT or hBAT-1, is an anti-PD-1 antibody described in WO2009/101611. AMP-224, also known as B7-DCIg, is a PD-L2-Fc fusion soluble receptor described in WO2010/027827 and WO2011/066342.

Another immune checkpoint protein that can be targeted in the methods provided herein is the cytotoxic T-lymphocyte-associated protein 4 (CTLA-4), also known as CD152.

The complete cDNA sequence of human CTLA-4 has the Genbank accession number L15006. CTLA-4 is found on the surface of T cells and acts as an "off" switch when bound to CD80 or CD86 on the surface of antigen-presenting cells. CTLA-4 is similar to the T-cell co-stimulatory protein, CD28, and both molecules bind to CD80 and CD86; also called. B7-1 and B7-2 respectively, on antigen-presenting cells. CTLA-4 transmits an inhibitory signal to T cells, whereas CD28 transmits a stimulatory signal. Intracellular CTLA-4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a humanized antibody, or a chimeric antibody); an antigen binding fragment thereof, an immunoadhesin, a fusion protein, or oligopeptide. Anti-human-CTLA-4 antibodies (or VII and/or VL domains derived therefrom) suitable for use in the present methods can be generated using methods well known in the art. Alternatively, art recognized anti-CTLA-4 antibodies can be used. For example, the anti-CTLA-4 antibodies disclosed in U.S. Pat. No. 8,119,129; PCT Pubin. Nos. WO 01/14424, WO 98/42752, WO 00/37504 (CP675, 206, also known as tremelimumab; formerly ticilimumab); U.S. Pat. No. 6,207,156; Hurwitz et al. (1998) *Proc Natl Acad Sci USA*, 95(17): 10067-10071; Camacho et al. (2004) J Clin Oncology, 22(145): Abstract No. 2505 (antibody CP-675206); and Mokyr et al. (1998) Cancer Res, 58:5301-5304 can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Application No. WO2001/014424, WO2000/037504, and U.S. Pat. No. 8,017,114; all incorporated herein by reference.

An exemplary anti-CTLA-4 antibody is ipilimumab (also known as 10D1, MDX-010, MDX-101, and Yervoy®) or antigen binding fragments and variants thereof (see, e.g., WO 01/14424). In other embodiments, the antibody comprises the heavy and light chain CDRs or VRs of ipilimumab. Accordingly, in one embodiment, the antibody comprises the CDR1, CDR2, and CDR3 domains of the VIA region of ipilimumab, and the CDR1, CDR2, and CDR3 domains of the VL region of ipilimumab. In another embodiment, the antibody competes for binding with and/or binds to the same epitope on CTLA-4 as the above-mentioned antibodies. In another embodiment, the antibody has an at least about 90% variable region amino acid sequence identity with the above-mentioned antibodies (e.g., at least about 90%, 95%, or 99% variable region identity with ipilimumab). Other molecules for modulating CTLA-4 include CTLA-4 ligands and receptors such as described in U.S. Pat. Nos. 5,844,905, 5,885,796 and International Patent Application Nos. WO1995001994 and WO1998042752; all incorporated herein by reference, and immunoadhesins such as described in U.S. Pat. No. 8,329,867, incorporated herein by reference.

Another immune checkpoint protein that can be targeted in the methods provided herein is lymphocyte-activation gene 3 (LAG-3), also known as CD223. The complete protein sequence of human LAG-3 has the Genbank accession number NP-002277. LAG-3 is found on the surface of activated T cells, natural killer cells, B cells, and plasmacytoid dendritic cells. LAG-3 acts as an "off" switch when bound to MHC class II on the surface of antigen-presenting cells. Inhibition of LAG-3 both activates effector T cells and inhibitor regulatory T cells. In some embodiments, the immune checkpoint inhibitor is an anti-LAG-3 antibody (e.g., a human antibody, a humanized antibody, or a chimeric antibody), an antigen binding fragment thereof, an immunoadhesin, a fusion protein, or oligopeptide. Anti-human-LAG-3 antibodies (or VH and/or VL domains derived therefrom) suitable for use in the present methods can be generated using methods well known in the art. Alternatively, art recognized anti-LAG-3 antibodies can be used. An exemplary anti-LAG-3 antibody is relatlimab (also known as BMS-986016) or antigen binding fragments and variants thereof (see, e.g., WO 2015/116539). Other exemplary anti-LAG-3 antibodies include TSR-033 (see, e.g., WO 2018/201096), MK-4280, and REGN3767. MGD013 is an anti-LAG-3/PD-1 bispecific antibody described in WO 2017/019846. FS118 is an anti-LAG-3/PD-L1 bispecific antibody described in WO 2017/220569.

Another immune checkpoint protein that can be targeted in the methods provided herein is V-domain Ig suppressor of T cell activation (VISTA), also known as C10orf54. The complete protein sequence of human VISTA has the Genbank accession number NP_071436. VISTA is found on white blood cells and inhibits T cell effector function. In some embodiments, the immune checkpoint inhibitor is an anti-VISTA3 antibody (e.g., a human antibody, a humanized antibody, or a chimeric antibody), an antigen binding fragment thereof, an immunoadhesin, a fusion protein, or oligopeptide. Anti-human-VISTA antibodies (or VII and/or VL domains derived therefrom) suitable for use in the present methods can be generated using methods well known in the art. Alternatively, art recognized anti-VISTA antibodies can be used. An exemplary anti-VISTA antibody is JNJ-61610588 (also known as onvatilimab) (see, e.g., WO 2015/097536, WO 2016/207717, WO 2017/137830, WO 2017/175058). VISTA can also be inhibited with the small molecule CA-170, which selectively targets both PD-L1 and VISTA (see, e.g., WO 2015/033299, WO 2015/033301).

Another immune checkpoint protein that can be targeted in the methods provided herein is indoleamine 2,3-dioxygenase (IDO) The complete protein sequence of human IDO has Genbank accession number NP_002155. In some embodiments, the immune checkpoint inhibitor is a small molecule IDO inhibitor. Exemplary small molecules include BMS-986205, epacadostat (INCB24360), and navoximod (GDC-0919).

Another immune checkpoint protein that can be targeted in the methods provided herein is CD38. The complete protein sequence of human CD38 has Genbank accession number NP_001766. In some embodiments, the immune checkpoint inhibitor is an anti-CD38 antibody (e.g., a human antibody, a humanized antibody, or a chimeric antibody), an antigen binding fragment thereof, an immunoadhesin, a fusion protein, or oligopeptide. Anti-human-CD38 antibodies (or VH and/or VL domains derived therefrom) suitable for use in the present methods can be generated using methods well known in the art. Alternatively, art recognized anti-CD38 antibodies can be used. An exemplary anti-CD38 antibody is daratumumab (see, e.g., U.S. Pat. No. 7,829, 673).

Another immune checkpoint protein that can be targeted in the methods provided herein is ICOS, also known as CD278. The complete protein sequence of human ICOS has Genbank accession number NP_036224. In some embodiments, the immune checkpoint inhibitor is an anti-ICOS antibody (e.g., a human antibody, a humanized antibody, or a chimeric antibody), an antigen binding fragment thereof, an immunoadhesin, a fusion protein, or oligopeptide. Anti-human-ICOS antibodies (or VII and/or VL domains derived therefrom) suitable for use in the present methods can be generated using methods well known in the art. Alternatively, art recognized anti-ICOS antibodies can be used. Exemplary anti-ICOS antibodies include JTX-2011 (see, e.g., WO 2016/154177, WO 2018/187191) and GSK3359609 (see, e.g., WO 2016/059602).

Another immune checkpoint protein that can be targeted in the methods provided herein is T cell immunoreceptor with Ig and ITIM domains (TIGIT). The complete protein sequence of human TIGIT has Genbank accession number NP_776160. In some embodiments, the immune checkpoint inhibitor is an anti-TIGIT antibody (e.g., a human antibody, a humanized antibody, or a chimeric antibody), an antigen binding fragment thereof, an immunoadhesin, a fusion protein, or oligopeptide. Anti-human-TIGIT antibodies (or VII and/or VL domains derived therefrom) suitable for use in the present methods can be generated using methods well known in the art. Alternatively, art recognized anti-TIGIT antibodies can be used. An exemplary anti-TIGIT antibody is MK-7684 (see, e.g., WO 2017/030823, WO 2016/028656).

Another immune checkpoint protein that can be targeted in the methods provided herein is OX40, also known as CD134. The complete protein sequence of human OX40 has Genbank accession number NP_003318. In some embodiments, the immune checkpoint inhibitor is an anti-OX40 antibody (e.g., a human antibody, a humanized antibody, or a chimeric antibody), an antigen binding fragment thereof, an immunoadhesin, a fusion protein, or oligopeptide. Anti-human-OX40 antibodies (or VH and/or VL domains derived therefrom) suitable for use in the present methods can be generated using methods well known in the art. Alternatively, art recognized anti-OX40 antibodies can be used. An exemplary anti-OX40 antibody is PF-04518600 (see, e.g., WO 2017/130076). ATOR-1015 is a bispecific antibody targeting CTLA4 and OX40 (see, e.g., WO 2017/182672, WO 2018/091740, WO 2018/202649, WO 2018/002339).

Another immune checkpoint protein that can be targeted in the methods provided herein is glucocorticoid-induced tumour necrosis factor receptor-related protein (GITR), also known as TNFRSF18 and AITR. The complete protein sequence of human GITR has Genbank accession number NP_004186. In some embodiments, the immune checkpoint inhibitor is an anti-GUR antibody (e.g., a human antibody, a humanized antibody, or a chimeric antibody), an antigen binding fragment thereof, an immunoadhesin, a fusion protein, or oligopeptide. Anti-human-t antibodies (or VII and/or VL domains derived therefrom) suitable for use in the present methods can be generated using methods well known in the art. Alternatively, art recognized anti-GITR antibodies can be used. An exemplary anti-GITR antibody is TRX518 (see, e.g., WO 2006/105021).

Another immune checkpoint protein that can be targeted in the methods provided herein is T-cell immunoglobulin and mucin-domain containing-3 (TIM3), also known as HAVCR2. The complete protein sequence of human TIM3 has Genbank accession number NP_116171. In some embodiments, the immune checkpoint inhibitor is an anti-TB/13 antibody (e.g., a human antibody, a humanized antibody, or a chimeric antibody), an antigen binding fragment thereof, an immunoadhesin, a fusion protein, or oligopeptide. Anti-human-TIM3 antibodies (or VH and/or VL domains derived therefrom) suitable for use in the present methods can be generated using methods well known in the art. Alternatively; art recognized anti-TIM3 antibodies can be used. Exemplary anti-TIM3 antibodies include LY3321367 (see, e.g., WO 2018/039020), MBG453 (see, e.g., WO 2015/117002) and TSR-022 (see, e.g., WO 2018/085469).

Another immune checkpoint protein that can be targeted in the methods provided herein is 4-1BB, also known as CD137, TNFRSF9, and ILA. The complete protein sequence of human 4-1BB has Genbank accession number NP_901552. In some embodiments, the immune checkpoint inhibitor is an anti-4-1BB antibody (e.g., a human antibody, a humanized antibody, or a chimeric antibody), an antigen binding fragment thereof, an immunoadhesin, a fusion protein, or oligopeptide. Anti-human-4-1BB antibodies (or VII and/or VL domains derived therefrom) suitable for use in the present methods can be generated using methods well known in the art. Alternatively, art recognized anti-4-1BB antibodies can be used. An exemplary anti-4-1BB antibody is PF-05082566 (utomilumab; see, e.g., WO 2012/032433).

In some embodiment, the immune therapy could be adoptive immunotherapy, which involves the transfer of autologous antigen-specific T cells generated ex vivo. The T cells used for adoptive immunotherapy can be generated either by expansion of antigen-specific T cells or redirection of T cells through genetic engineering (Park, Rosenberg et al. 2011). Isolation and transfer of tumor specific T cells has been shown to be successful in treating melanoma. Novel specificities in T cells have been successfully generated through the genetic transfer of transgenic T cell receptors or chimeric antigen receptors (CARs) (Jena, Dotti et al, 2010). CARs are synthetic receptors consisting of a targeting moiety that is associated with one or more signaling domains in a single fusion molecule. In general, the binding moiety of a CAR consists of an antigen-binding domain of a single-chain antibody (scFv), comprising the light and variable fragments of a monoclonal antibody joined by a flexible linker. Binding moieties based on receptor or ligand domains have also been used successfully. The signaling domains for first generation CARs are derived from the cytoplasmic region of the CD3zeta or the Fc receptor gamma chains. CARs have successfully allowed T cells to be redirected against antigens expressed at the surface of tumor cells from various malignancies including lymphomas and solid tumors (Jena, Dotti et al. 2010).

In one embodiment, the present application provides for a combination therapy for the treatment of cancer wherein the combination therapy comprises adoptive T cell therapy and a checkpoint inhibitor. In one aspect, the adoptive T cell therapy comprises autologous and/or allogenic T-cells. In another aspect, the autologous and/or allogenic T-cells are targeted against tumor antigens.

4. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present invention, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 9, 10, 11, or 12 months. These treatments may be of varying dosages as well.

5. Other Agents

It is contemplated that other agents may be used in combination with certain aspects of the present invention to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present invention to improve the treatment efficacy.

IV. KITS

Kits are envisioned containing diagnostic agents, therapeutic agents, and/or other therapeutic and delivery agents. The kit may comprise reagents capable of use in determining the level of sEV-VEGF in a sample, the level of biologically active VEGF in a sample, and/or the level of VEGF that is available to bind bevacizumab in a sample. The kit may also comprise a suitable container means, which is a container that will not react with components of the kit, such as an eppendorf tube, a syringe, a bottle, or a tube. The container may be made from sterilizable materials such as plastic or glass. The kit may further include an instruction sheet that outlines the procedural steps of the methods, such as the same procedures as described herein or are otherwise known to those of ordinary skill.

V. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Materials and Methods

Reagents.

Sources of Ab were as follows: anti-VEGF (for detection: R&D Systems MAB2931, Thermo Fisher Scientific P802, Abcam ab52917, ab183100; for capture: R&D Systems MAB293; for neutralization (bevacizumab): Genentech);

anti-VEGF-phycoerythrin (PE) (Abeam ab209439); anti-VEGFR2 (for detection: Cell Signaling Technology 9698; for neutralization: R&D Systems MAB3572); anti-phospho-VEGFR2 (Tyr1175); anti-calnexin (Cell Signaling Technology 3770; 2679); anti-CD63 (for flow cytometry: BD Biosciences 556019; for immunogold labeling: System Biosciences EXOAB-CD63A-1); an ti-CD63-PE/Cy7, anti-CD63-FITC, anti-CD81-FITC, anti-CD9-FITC (BioLegend 353010, 353005, 349503, 312103); anti-flotillin-1, anti-HSP70 (BD Biosciences 610820, 610607); anti-TSG101, anti-$\alpha$-actinin-4, anti-CD31, anti-UP (Abeam ab125011, ab108198, ab28364, ab5450); anti-HSP90B1 (Enzo Life Sciences ADI-SPA-850); anti-bevacizumab (Abnova mab11128); anti-actin, anti-human IgG (Fc specific)-horseradish peroxidase (HRP) (Sigma-Aldrich A1978, A0170); normal human IgG (Innovative Research IR-HU-GF-ED); normal mouse IgG (Thermo Fisher Scientific 10400C); 10 nm anti-rabbit IgG gold conjugate (Electron Microscopy Sciences 25109); other secondary Ab (BioLegend 409312, 400126; BD Biosciences 340272; Abeam ab97263, ab97198, ab97223; Jackson ImmunoResearch 115-035-166, 111-035-144; Santa Cruz Biotechnology se-3739). Concentrations of Ab used in assays described below. ELISA kits were as follows: human VEGF, GRO$\alpha$, IL-8 and FGF-2, mouse YEE& (R&D Systems DVE00, DGR00B, D8000C, DFB50, MMV00), human CD63, TSG101 (LSBio LS-F11093, LS-F8581). VEGFR1/R2-Fc (Aflibercept, Regeneron Pharmaceuticals) was provided by a M. Brown (Houston Methodist Hospital). Other reagents were as follows: recombinant $VEGF_{121}$ (Shenandoah Biotechnology); recombinant $VEGF_{165}$ (BioLegend); recombinant $VEGF_{189}$, dynasore (R&D Systems); axitinib, vandetanib (Cell Signaling Technology); DMSO, chlorpromazine, heparinase I and III blend from *Flavobacterium heparimum*, chondroitinase ABC from *Proteus vulgaris*, DAN (Sigma-Aldrich); fractionated heparan sulfate polymer (molecular weight approximately 40 kDa) (Amsbio).

Cell Culture.

Culture media was purchased from Corning. HUVEC were purchased from American Type Culture Collection (ATCC) and cultured in Medium 199 supplemented with 20% fetal bovine serum (FBS), endothelial cell growth supplement (50 $\mu$g/mL) (Millipore), L-glutamine and penicillin-streptomycin on plates coated with 0.1% gelatin (Sigma-Aldrich). Parental ES2, SKOV3, HCT116 and 786-0 cell lines were purchased from ATCC, confirmed to be free of *mycoplasma* contamination and authenticated by short tandem repeat analysis. Cancer cell lines were cultured in McCoy's 5A medium (E52, SKOV3) or DMEM (HCT116, 786-0) supplemented with 10% MS and penicillin-streptomycin. HCT116 VEGF$^{-/-}$ cells were generated in a previous study by targeting exon 2 of the VEGFA gene for disruption with an adeno-associated virus knockout construct (Dang et al., 2006). GFP-expressing ES2 VEGF$^{-/-}$ cells were generated in this study by CRISPR/Cas9 gene editing using the human VEGFA. gene knockout kit (Origene). Briefly, ES2 cells were co-transfected with VEGFA sgRNA. plasmid and donor vector that contains predesigned homologous sequences flanking the GFP and puromycin resistance selection cassette. Individual clones, derived from single GFP-expressing cells, were selected with puromycin (0.5 $\mu$g/mL) and screened by ELISA to confirm VEGFA gene knockout. CHO-K1 and pgsD-677 cell lines were purchased from ATCC and cultured in Ham's F-12 medium supplemented with 10% FBS and penicillin-streptomycin. In VEGF reconstitution experiments, 293T cells (purchased from ATCC) were transfected with lentiviral constructs encoding $VEGF_{121}$, $VEGF_{165}$ and $VEGF_{189}$ (Genecopoeia) by using Lipofectamine 3000 (Thermo Fisher Scientific). At 2 days thereafter, supernatants containing lentiviral particles were harvested and used to infect ES2 $VEGF^{-/-}$, HCT116 $VEGF^{-/-}$, CHO-K1 and pgsD-677 cells.

Clinical Specimens.

Studies using human tissue specimens were approved by the Institutional Research Board of the University of Texas MD Anderson Cancer Center (UTMDACC) and the Institutional Research Board of the University of Chicago. Full informed consent was obtained from all human subjects. All specimens used in this study were residual and not necessary for diagnosis. To analyze cellular VEGF and sEV-VEGF, specimens of tumor tissue and ascites of women with ovarian carcinoma were obtained from the Ovarian Cancer Tumor Bank at the University of Chicago. Serum and plasma samples of individuals with colorectal and renal cell carcinoma were obtained from the National Cancer Institute-supported Cooperative Human Tissue Network, Residual blood samples from healthy adult donors were provided by the UTMDACC Blood Bank. To analyze relationships between VEGF levels and outcomes following bevacizumab treatment, residual plasma samples from study NCT0013217 (Jonasch et al., 2009) were obtained from the Eckstein Tissue Acquisition Laboratory at UTMDACC. These samples were collected from patients who were enrolled in study NCT00113217 at UTMDACC between March 2005 and March 2008, Collection, processing and analysis of plasma samples were performed at UTMDACC. Of the 27 patients with newly diagnosed metastatic renal cell carcinoma who were treated presurgically with single-agent bevacizumab and thereafter restaged in study NCT00113217 (Jonasch et al., 2009), residual baseline plasma samples were available for 17 evaluable patients with Stage IV disease. To eliminate bias, all assays of VEGF levels in plasma samples were performed blinded to clinical data.

Animal Studies.

Animal studies were conducted in compliance with protocols approved by the UTMDACC Institutional Animal Care and Use Committee. Four-week-old female nude mice (purchased from UTMDACC animal facility) were used to propagate xenografts. To evaluate VEGF levels in ascites, mice were inoculated i.p, with $1 \times 10^6$ ES2 $VEGF^{+/+}$ cells, and euthanized by $CO_2$ asphyxiation upon formation of morbid ascites (median survival time of 3 weeks), To evaluate the effects of sEVs, mice were inoculated i.p. with $2 \times 10^6$ GFP-expressing ES2 $VEGF^{-/-}$ cells. At 7 days thereafter when tumors were palpable, mice were randomized into groups (n=6 mice per group) and administered either phosphate-buffered saline (PBS), sEVs of ES2 $VEGF^{+/+}$ cells or of ES2 $VEGF^{-/-}$ cells (500 μg per animal) or recombinant human VEGF (5 ng per animal), alone or in combination with normal human IgG (5 mg/kg) or bevacizumab (5 mg/kg). Mice were treated with these agents i.p. 3 times a week for 2 weeks and thereafter euthanized. A 5 mg/kg dose of bevacizumab has been used by other investigators to treat mice with xenografts derived from ES2 $VEGF^{+/+}$ cells (Tsujioka et al., 2011). The 6 doses of sEVs at 500 μg per dose was based on the average volume of ascites and concentration of tumor-derived sEV-VEGF in ascites that forms in mice with i.p. xenografts derived from ES2 $VEGF^{+/+}$ cells (FIGS. 15A, 15B). Following euthanasia, volumes of ascites were measured. GFP-expressing tumors were visualized under a Leica MZMLIII stereomicroscope equipped with a GFP filter set and digital camera. Images were captured by using Picture Frame software (Optronics). Tumor burden was quantified by measuring areas of fluorescence signals within the abdominal cavity in captured images by using Image Pro Plus software (Media Cybernetics) as performed previously (Ko et al., 2009). To visualize intratumoral blood vessels, sections of omental tumor tissues, frozen in Optimal Cutting Temperature compound (Thermo Fisher Scientific), were stained with Ab to GFP (1:500 dilution) and CD31 (1:50 dilution) and with DAPI, and viewed under a Nikon 80i fluorescence microscope. Numbers of intratumoral $CD31^+$ cells were counted in 5 random 100× fields per section and an average score was determined for each mouse. To evaluate circulating VEGF levels, mice were inoculated s.c. with $5 \times 10^6$ ES2 $VEGF^{+/+}$ cells or HCT116 $VEGF^{+/+}$ cells. At 7 days thereafter when tumors were palpable, blood samples were collected retro-orbitally. Mice were then randomized into groups (n=3 to 4 mice per group) and administered either normal human IgG (5 mg/kg) or bevacizumab (5 mg/kg) i.p. 3 times for one week followed by retro-orbital blood collection. Volumes of s.c. tumors were calculated from 2 perpendicular measurements of tumor diameters taken using calipers. Pre- and post-treatment plasma samples were pre-cleared with Protein G Sepharose 4 Fast Flow (GE Healthcare) at 4° C. for 16 h to remove Ab-bound VEGF and thereafter were assayed for VEGF by ELISA.

Isolation of sEVs.

In all experiments, sEVs were isolated from conditioned media and body fluids (with the exception of plasma samples in FIG. 8G) by the following procedure. Conditioned media was prepared by culturing cancer cells in media containing 2% FBS for 48 h. For each batch preparation of sEVs, a total of 360 mL of conditioned media collected from 20×150 mm dishes of cells at 90% confluence was used. For each purification of sEVs from biological fluid, a 1 mL sample of fluid was used. Conditioned media and biological fluids were centrifuged at 2,400×g at 4° C. for 10 min to remove intact cells and cell debris. Thereafter, supernatants were filtered through a 0.2 μm pore size filter to exclude particles of >200 nm in diameter and then concentrated using a Centricon® Plus-70 centrifugal filter unit with a 100 kD nominal molecular weight limit (Millipore) to exclude soluble proteins of <100 kD in size. To prepare the discontinuous iodixanol gradient, solutions of iodixanol were prepared by diluting a stock solution of OptiPrep™ (60% (w/v) aqueous iodixanol, Axis-Shield PoC) in buffer containing 0.25 M sucrose, 10 mM Tris-HCl (pH 7.4) and 1 mM EDTA. Concentrated conditioned media and biological fluids were mixed with 1.5 mL of Optiprep™ stock solution on the bottom of a 14×95 mm polyallomer ultracentrifuge tube (Beckman Coulter). The gradient was formed by stepwise layering of 3.0 mL of 40% (w/v) iodixanol solution, 2.5 mL each of 20% (w/v) and 10% (w/v) iodixanol solutions and 2.0 mL of 5% (w/v) iodixanol solution. Centrifugation was performed at 200,000×g at 4° C. for 18 h. Ten gradient fractions of 1.0 mL were collected from the top to bottom. The density of each fraction was determined from absorbance readings at 244 nm using a standard curve generated from serial dilutions of iodixanol solution (Schroder et al., 1997). Individual fractions were washed with PBS. concentrated by using Centricon® filter units, and suspended in PBS for further analysis. Because volumes of plasma samples of bevacizumab-treated patients were small (200 μL), sEVs were isolated from these samples (FIG. 8G) by using ExoQuick reagent (System Biosciences). Briefly, plasma samples were centrifuged at 3,000×g for 15 minutes to remove cells and debris. Samples (100 μL) were then diluted with the addition of 400 μL, PBS and 120 μL precipitation solution, vortexed and incubated at 4° C. for 16 h. Thereafter, sEVs were precipitated by centrifugation at 1,500×g for 30 min and suspended in PBS for further analysis.

Depletion of sEVs.

Samples of plasma and ascites (diluted 1:10 in PBS) and conditioned media were centrifuged at 2,400×g at 4° C. for 10 min to remove intact cells and cell debris. Thereafter, supernatants were filtered through a 0.2 μm pore size filter to remove larger particles. A 300 μL aliquot of filtrate was retained for analysis of VEGF. The remainder of the filtrate was centrifuged at 100,000×g at 4° C. for 18 h to remove sEVs. Thereafter, the supernatant (comprising of sEV-depleted sample) was assayed for VEGF.

Particle Size Analysis.

Particle size distribution of purified sEVs was evaluated by nanoparticle tracking analysis using a Nanosight LM10 (Malvern) by Alpha Nano Tech LLC, For each batch purification of sEVs, an average of $2×10^9$ vesicles was isolated. Ten replicate measurements were made for an individual batch of sEVs.

Immunogold Labeling and Transmission Electron Microscopy.

For immunogold labeling, carbon-coated, formvar-coated nickel grids (200 mesh) were treated with poly-L-lysine for 30 min, Samples were then loaded and allowed to absorb for 1 h. Grids were placed into buffer containing 2% bovine serum albumin (BSA) and 0.1% saponin for 20 min, and then placed into CD63 Ab (1:5 dilution) or VEGF Ab (1:10 dilution) at 4° C. for 16 h. Control grids were incubated without primary Ab. Thereafter, grids were rinsed with PBS and floated on drops of anti-rabbit IgG labeled with 10 nm gold particles (1:20 dilution) for 2 h at room temperature (RT). Following washing with PBS, grids were placed in 1% glutaraldehyde for 5 min and washed in $H_2O$. Grids were stained for contrast for 1 min with 1% uranyl acetate and allowed to dry. Samples were evaluated under a JEM 1010 transmission electron microscope (JEOL USA, Inc.) at an accelerating voltage of 80 Kv. Images were obtained by using the ANT Imaging System (Advanced Microscopy Techniques Corp.).

Fluorescence labeling of sEVs. sEVs were incubated with PKH67 green or PKH26 red fluorescent linker dye (Sigma-Aldrich) (1:500 dilution) in a final volume of 100 μL at RT for 10 min. Reactions were stopped by adding 100 μL of 5% BSA in PBS. sEVs were precipitated using Exoquick-TC solution (System Biosciences) and resuspended in PBS. As described further below, sEVs were also labeled with exo-FITC dye (Systems Biosciences).

Analysis of sEV Uptake.

HUVEC ($10^5$ cells) were incubated with PKH26-labeled sEVs (100 μg/mL) at 37° C. for times indicated in the legends. As a negative control, HUVEC were incubated with PKH26 linker dye precipitated with Exoquick-TC solution without sEVs to exclude the presence of aggregates of linker dye. Uptake of sEVs in HUVEC was visualized under a Nikon 80i fluorescence microscope attached to a digital camera. Images were captured by using NIS Element BR 4 software (Nikon). Uptake of sEVs was also evaluated by measuring PKH26 fluorescence intensity in the gated population of viable HUVEC by using a FACSCalibur™ cytometer equipped with CellQuest™ Pro software (BD Biosciences). A minimum of 10,000 gated events was analyzed for each sample. Three independent experiments were performed for each assay.

Treatment of Cells with Inhibitors.

Uptake of sEVs was blocked by treating HUVEC with chlorpromazine (15 μM) or dynasore (50 μM) for 30 min prior to addition of sEVs. As a negative control, HUVEC were pretreated with DMSO solvent (0.1%). VEGFR signaling was blocked by treating HUVEC with axitinib (1 nM) or vandetanib (1 μM) for 2 h or with neutralizing Ab to VEGFR2 (250 ng/mL) for 1 h prior to addition of sEVs or recombinant VEGF. In other experiments, sEVs (100 μg/mL) or recombinant VEGF (1 ng/mL) were incubated with either normal human IgG, bevacizumab or VEGFR1/ R2-Fc (50 ng/mL) for 16 h. Thereafter, mixtures were added to HUVEC cultures. To detect intracellular VEGF, cancer cells where indicated were incubated at 37° C. for 6 h with brefeldin A (BioLegend) (5 μg/mL) to block protein secretion and then harvested.

Tube Formation Assay.

Wells of 96-well plates were coated with growth factor-reduced Matrigel (BD Biosciences) (50 μL/well) and incubated at 37° C. for 30 min. HUVEC ($10^4$ cells/well) were then seeded in FBS-free Medium 199 without or with addition of sEVs (100 μg/mL) or recombinant VEGF (1 ng/mL), or seeded in whole or sEV-depleted conditioned media. Following incubation at 37° C. for 4 h, capillary tube structures were visualized under a Nikon TS100 light microscope attached to a digital camera. In each experiment, images of 2 to 3 random 100× fields of each well were captured by using NIS Element BR 4 software (Nikon). The number of tubes in each field was quantified by using NIH Image) software with Angiogenesis Analyzer plugin, and an average calculated for each well. Three to 4 independent experiments were performed for each assay, where each experiment used a different batch of sEVs.

Migration Assay.

sEVs (100 μg/mL) or recombinant VEGF (1 ng/mL) were suspended in Medium 199 and added to the lower chamber of 24-well transwell chambers (Corning). HUVEC ($10^5$ cells/well) were seeded in the upper chamber and incubated at 37° C. for 5 h. Migrating cells were then fixed, stained with crystal violet solution (Sigma-Aldrich) and visualized under a Nikon TS100 light microscope attached to a digital camera. In each experiment, images of 2 to 3 random 100× fields of each well were captured by using NIS Element BR 4 software. The number of migrating cells in each field was manually counted, and an average calculated for each well. Four independent experiments were performed for each assay, where each experiment used a different batch of sEVs.

Immunoblot Analysis.

Extracts were prepared by lysing whole cells and sEVs in M-PER buffer (Thermo Fisher Scientific). Protein concentrations of lysates were determined by Bradford assay (Bio-Rad). Lysates were separated by SDS-polyacrylamide gel electrophoresis under non-reducing conditions to detect VEGF and under reducing conditions to detect other proteins, and then transferred to polyvinylidene difluoride membrane (GE Healthcare). Membranes were blocked with 5% non-fat milk in Tris-buffered saline with 0.1% Tween-20 (TBS-T), incubated with primary Ab at 4° C. for 16 h, and then washed with TBS-T buffer. Primary Ab were used at the following dilutions: 1:1000 (for Ab to TSG101, α-actinin-4, HSP90B1, calnexin, phospho-VEGFR2, VEGFR2, VEGF); 1:2000 (for Ab to HSP70); 1:5000 (for Ab to actin). Thereafter, membranes were incubated with 1-IRP-conjugated secondary Ab (1:5000 dilution), washed and visualized with ECL detection reagent (Millipore). Immunoblot data was verified in 3 independent experiments.

Detection of Angiogenic Factors by Ab Array and ELISA.

Angiogenesis-related proteins were detected in sEVs by using the Human Angiogenesis Antibody Array (Abeam). sEVs were lysed in buffer provided by the manufacturer.

Membranes were incubated with sEV lysate (100 μg) at 4° C. for 16 h, and then incubated with Ab cocktail and visualized according to manufacturer's instructions. Levels of VEGF, GROα, IL-8, FGF-2, CD63 and TSG101 in sEVs were quantified by ELISA as follows. Purified sEVs were divided into identical aliquots. One set of aliquots was lysed in passive lysis buffer (Promega). Lysates of sEVs were assayed by ELISA to determine the total content of a given protein in sEVs, expressed relative to total protein content in sEVs. Other aliquots of sEVs were left intact and assayed by ELISA to determine the amount of a given protein on the surface of sEVs, ELISA data was measured by using an ELx800 microplate reader equipped with Gen 5 software (BioTek). Three independent experiments were performed for each assay.

Detection of sEV-Associated Proteins by Flow Cytometry.

To detect sEV-associated proteins by using Ab-coupled microbeads, acquisition and analysis of flow cytometry data were performed using a FACSCalibur™ cytometer equipped with CellQuest™ Pro software (BD Biosciences). Initially, Exo-Flow microbeads ($6.4 \times 10^5$ beads of 9.1 μm diameter) (System Biosciences) were coupled with the appropriate secondary Ab (1 mg) and then with the desired detection Ab (i.e. 1 μg for anti-VEGF, anti-CD63, anti-TSG101, bevacizumab, VEGFR1/R2-Fc) following manufacturer's instructions. Thereafter, microbeads were incubated with sEVs (100 μg, approximately $2 \times 10^8$ vesicles) at 4° C. for 16 h with rotation, washed with 1% BSA in PBS, stained with exo-FITC dye, and then acquired. Binding of Ab to protein on the surface of sEVs was evaluated by analyzing exo-FITC fluorescence in the gated population of singlet microbeads. A minimum of 10,000 gated events was analyzed for each sample. To confirm that bevacizumab was coupled to microbeads, microbeads were stained with Ab to bevacizumab (1:100 dilution) at 4° C. for 30 min, washed with 1% BSA in PBS, and then stained with PerCP-conjugated anti-mouse IgG (1:100 dilution) at 4° C. for 30 min. Following washing, microbeads were acquired and PerCP fluorescence analyzed in the gated population of singlet microbeads. Where indicated in the text, sEV-associated surface proteins were assayed following enzymatic treatment. PKH67-labeled sEVs (100 μg) were suspended in digestion buffer (DMEM supplemented with 0.5% BSA and 20 mM HEPES-HCl (pH 7.4)) and incubated with heparinase I and III blend (1 mU/mL) or with chondroitinase ABC (50 mU/mL) at 37° C. for 3 h. Fresh enzyme was then added and samples incubated for a further 16 h. sEVs were then extensively washed with PBS, concentrated by using Centricon® filter units, and then incubated with Ab-coupled microbeads. Binding was evaluated by analyzing PKH67 fluorescence in the gated population of singlet microbeads. Three independent experiments were performed for each assay. Contour plots were generated by using CellQuest™ Pro software. To detect sEV-associated proteins by direct staining of sEVs, acquisition and analysis of flow cytometry data were performed using a BD FACSCanto II cytometer equipped with FACS Diva software (BD Biosciences). Settings were optimized by using bead calibration kits (50 nm, 100 nm, 200 nm and 500 nm diameter beads) purchased from Bangs Laboratories. To optimize settings for detecting proteins on the surface of sEVs by flow cytometry, a 100 μL aliquot of sEV sample (100 μg, approximately $2 \times 10^8$ vesicles) was incubated at RT for 30 min in combination with PE/Cy7-conjugated isotype control (1:100 dilution) in combination with FITC-conjugated isotype control or CD63 Ab or CD81 Ab or CD9 Ab (1:100 dilution). To detect VEGF on the surface of sEVs, a 100 μL aliquot of sEV sample (100 μg, approximately $2 \times 10^8$ vesicles) was incubated at RT for 30 min with PE-conjugated VEGF Ab or isotype control (1:100 dilution) in combination with PE/Cy7-conjugated CD63 Ab or isotype control (1:100 dilution). Following incubation, samples were diluted to final volume of 500 μL in PBS and acquired. FITC, PE, and PE/Cy7 fluorescence was analyzed in the gated population of sEVs. A minimum of 10,000 gated events was analyzed for each sample. Contour plots were generated by using FlowJo v10.6.0 software (FlowJo LLC).

Detection of Cellular Proteins by Flow Cytometry.

For detecting intracellular VEGF, brefeldin A-treated cancer cells were fixed with 1% paraformaldehyde at 4° C. for 20 min and then permeabilized in 0.1% saponin at RT for 15 min. Following washing with 1% BSA in PBS, cells were incubated with bevacizumab or VEGFR1/R2-Fc (25 μg/mL) at 4° C. for 30 min and then washed. Cells were stained with PerCP-conjugated anti-human IgG (Fc specific) (1:100 dilution), then washed and fixed. Cells were acquired by a FACSCalibur™ flow cytometer and staining analyzed by CellQuest™ Pro software. A minimum of 10,000 gated events was analyzed for each sample.

Analysis of VEGF Stability.

Stability of VEGF protein was assayed in healthy adult donor plasma as follows. Recombinant VEGF (20 ng) or sEVs (2 mg) were added to 400 μL of 10% plasma and placed at 37° C. At 0, 0.5, 3, 6, 9, 12, 16 and 24 h thereafter, aliquots of 40 μL were removed and immediately frozen. Following collection of all samples, thawed samples were diluted and then assayed for VEGF content by ELISA.

Detection of Heparin-Hound VEGF.

Wells of 96-well High Bind microplates (Corning) were coated with fractionated heparan sulfate polymer (5 μg) or with VEGF capture Ab (100 ng) at RT for 16 h. Wells were then washed 3 times with wash buffer (R&D Systems), incubated with recombinant $VEGF_{189}$ (2 ng) for 2 h and washed again. Thereafter, bevacizumab or VEGFR1/R2-Fc (100 ng in a reaction volume of 100 μL) were added to wells that contained $VEGF_{189}$ bound to heparan sulfate polymer or to VEGF capture Ab, and incubated for 2. h at RT. Wells were then washed 3 times. Binding of bevacizumab and VEGFR1/R2-Fc was detected by incubation with HRP-conjugated goat anti-human IgG (Fc-specific) (1:5000 dilution) for 1 h at RT, followed by washing and addition of HRP substrate solution (R&D Systems). Absorbance was read at 450 nm. The reading of wells that contained heparin-bound VEGF 189 was normalized to the reading of wells that contained VEGF bound to VEGF capture Ab.

Quantification of Unbound Bevacizumab and VEGFR1/R2-Fc.

Bevacizumab (5 ng) or VEGFR1/R2-Fc (5 ng) were incubated at 4° C. for 16 h with a range of amounts of sEVs and recombinant VEGF proteins indicated in the legends in a reaction volume of 100 μL In other experiments, 100 μL of conditioned media was pre-cleared with 50 μL of Protein G Sepharose 4 Fast Flow at RT for 2 h to remove Ab, and then incubated with the addition of bevacizumab (2.5 ng) at 4° C. for 16 h. Following incubation, concentrations of NAJAF-unbound bevacizumab and VEGF-unbound VEGFR1/R2-Fc in reaction samples and conditioned media were assayed by ELISA as follows. Wells of 96-well High Bind microplates were coated with recombinant VEGF (100 ng) at RT for 16 h, After washing three times with wash buffer (R&D Systems), wells were blocked with 10% goat serum for 1 h and washed again. Thereafter, reaction samples, conditioned media, and bevacizumab or VEGFR1/R2-Fc controls (100 μL) were added to wells. Standard controls of bevacizumab and VEGFR1/R2-Fc were prepared at concentrations ranging from 0.78 ng/mL to 50 ng/mL. VEGF-unbound bevacizumab and VEGF-unbound VEGFR1/R2-Fc (i.e. captured by precoated recombinant VEGF) were detected by incubation with HRP-conjugated goat anti-human IgG (Fc specific) (1:5000 dilution) for 1 h at RT, followed by washing and addition of HRP substrate solution. Absorbance was read at 450 nm. The concentration of VEGF-unbound bevacizumab or VEGF-unbound VEGFR1/R2-Fc in each reaction was calculated from the relevant standard curve.

Statistics and Reproducibility.

Statistical analysis was performed by using STATIS-TICA13.1 (StatSoft Inc.) and Prism8 software (GraphPad Software, Inc.). For each type of in vitro assay, 2 to 6 independent experiments (i.e. using independent samples) were performed to confirm reproducibility. Based on the variance of i.p. xenograft growth that was observed in control mice in preliminary studies, power calculations indicated the use of n=6 mice per group to detect a difference of >39% in i.p. tumor burden, numbers of intratumoral endothelial cells and ascites volume between groups in a two-sided test at a significance of P<0.05 and with 80% probability. For studies of clinical specimens, sample size was limited by availability of archived specimens. Normal-ity of data distribution in groups was assessed by Shapiro-Wilk test. Significance of data in in vitro and in vivo assays was assessed by one-way or two-way ANOVA with Bon-ferroni's corrections for multiple comparisons, or by unpaired or paired two-tailed Student's t-test. Significance of data between patient groups was assessed by Mann-Whitney U-test as data in these groups was non-normally distributed. P values of <0.05 were considered significant.

Example 2—Uptake-Independent Effects of sEVs on Endothelial Cells

Figure 1A:
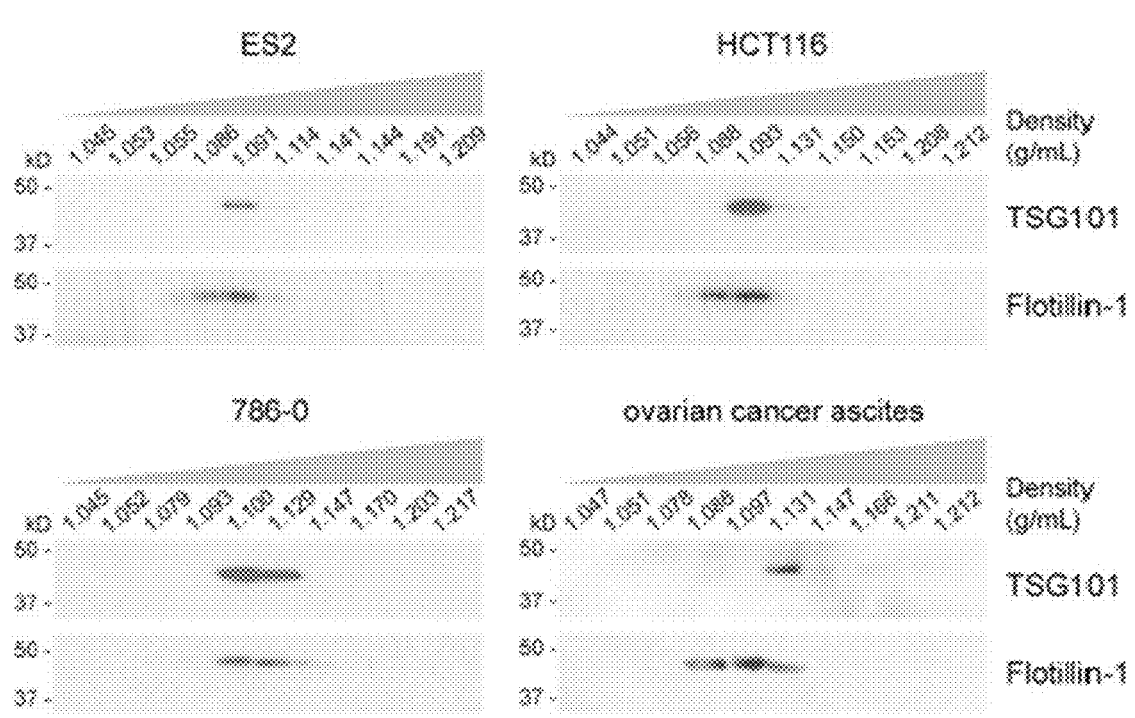
FIGS. 1A-1H. Cancer cell-derived small extracellular vesicles (sEVs) can stimulate endothelial cell migration and tube formation independently of uptake.
Figure 1B:
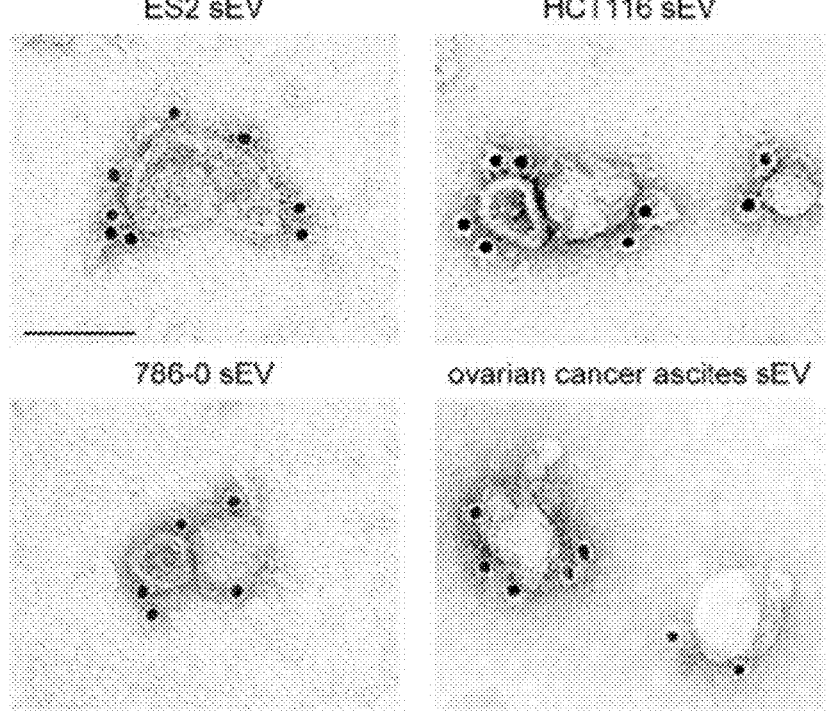
Figure 1C:
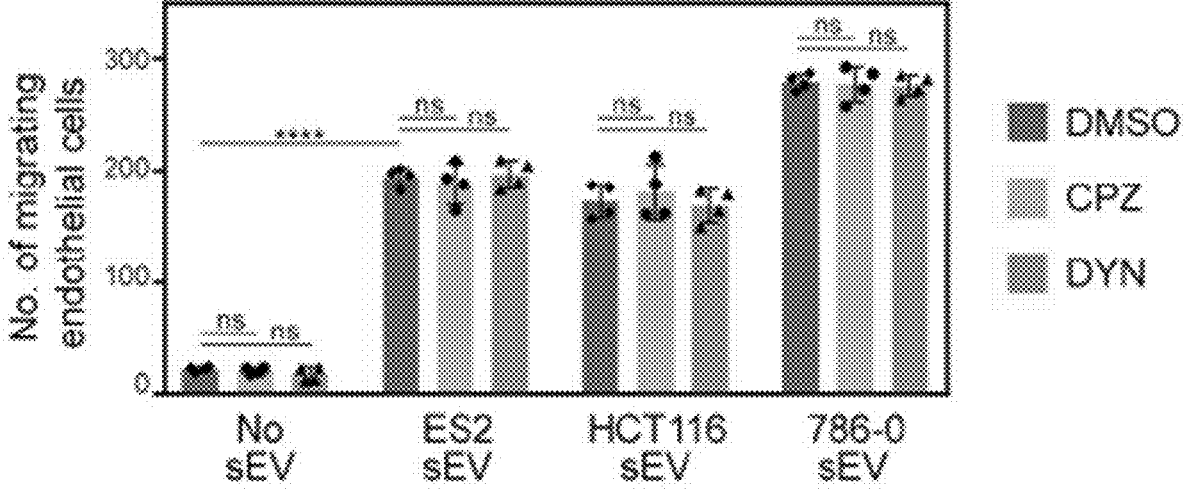
Figure 1D:
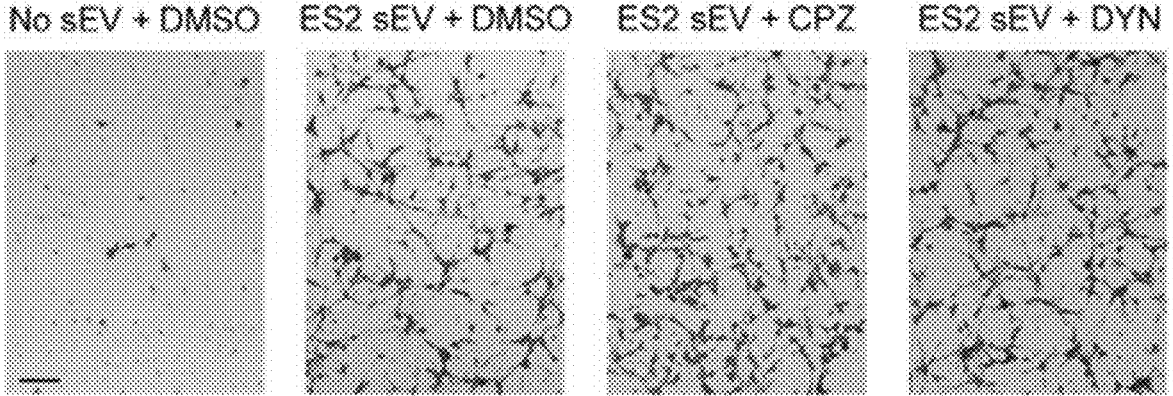
Figure 1E:
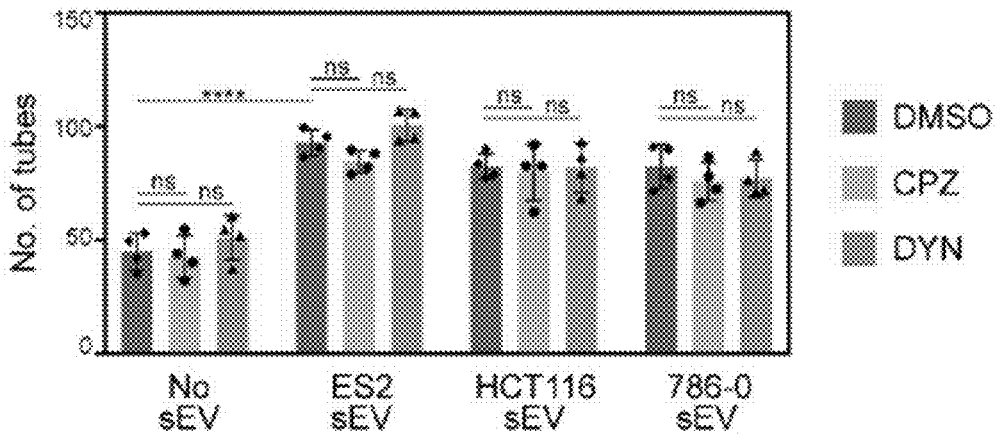
Figure 1F:
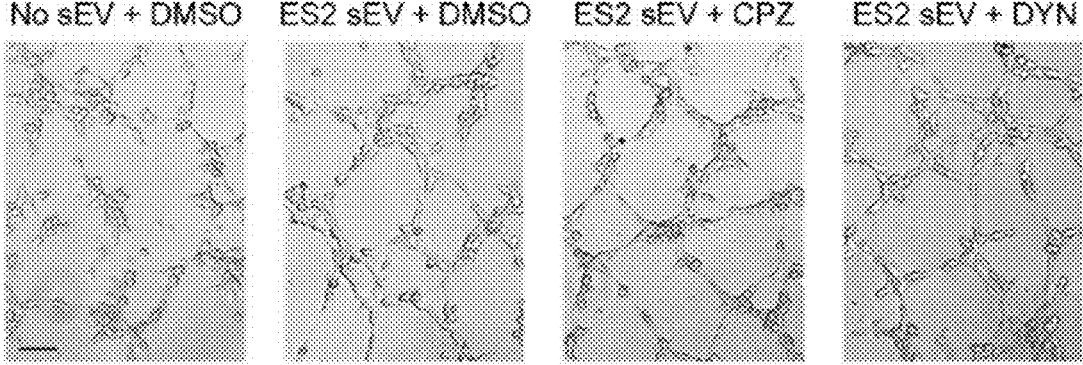
Figure 1G:
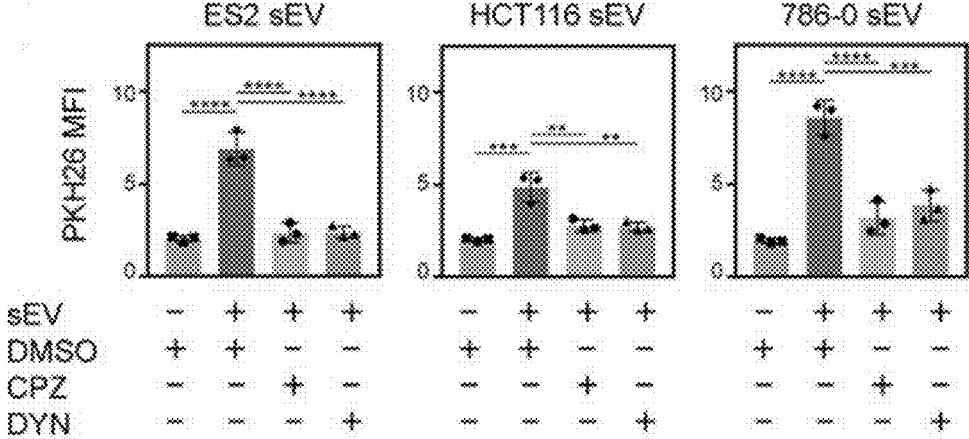
Figure 1H:
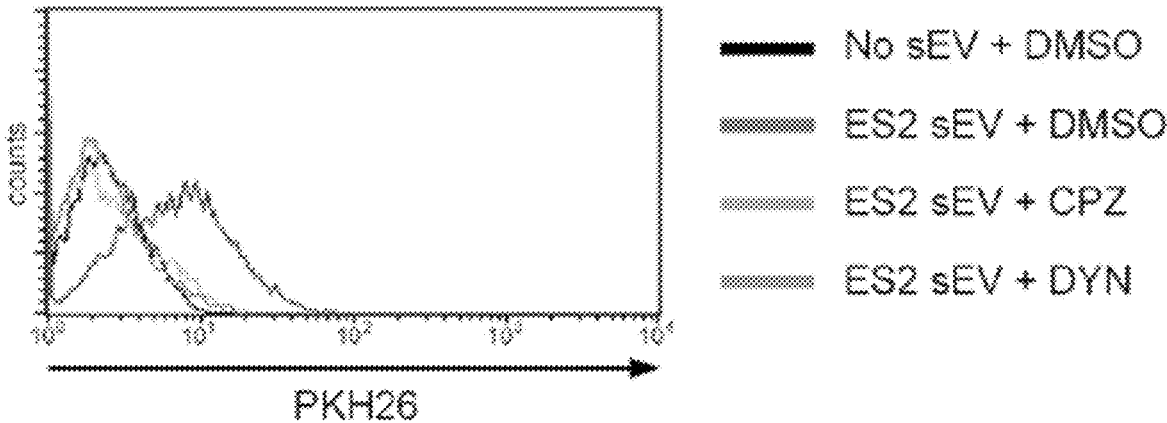
Figure 9A:
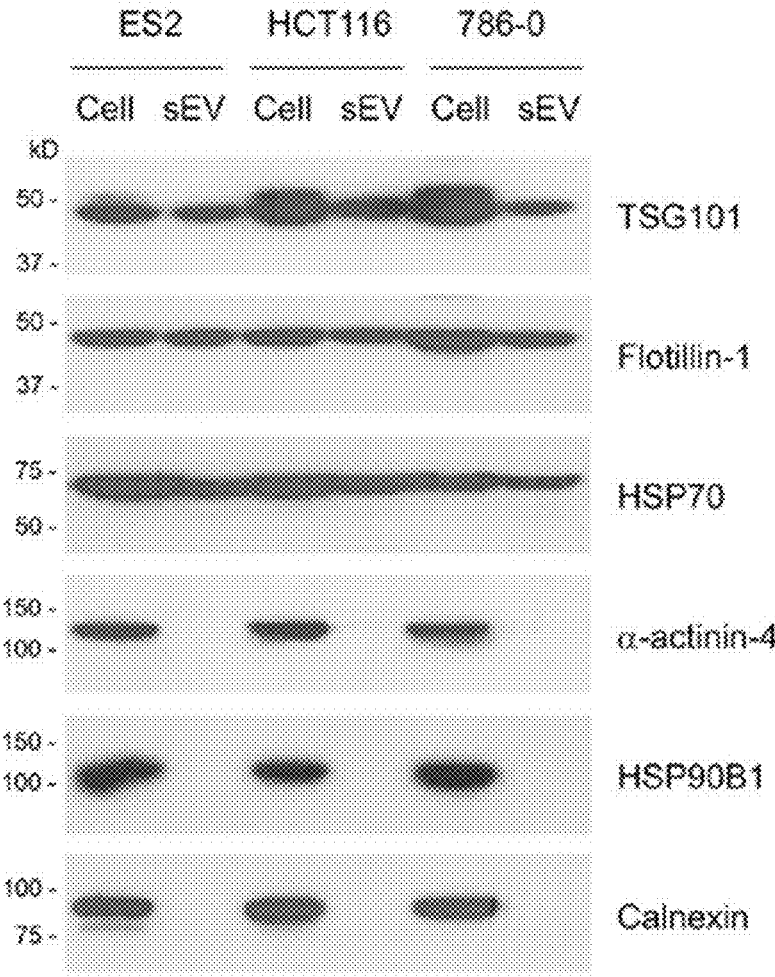
FIGS. 9A-9B. Analysis of markers and particle size distribution of sEVs secreted by cancer cells.
Figure 9B:
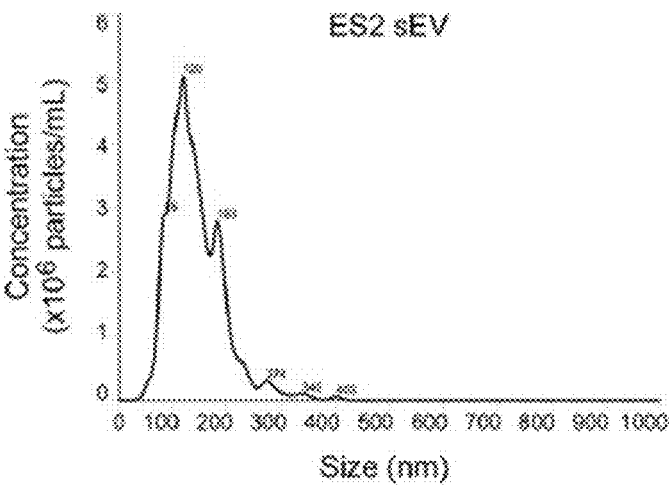
Figure 9B:
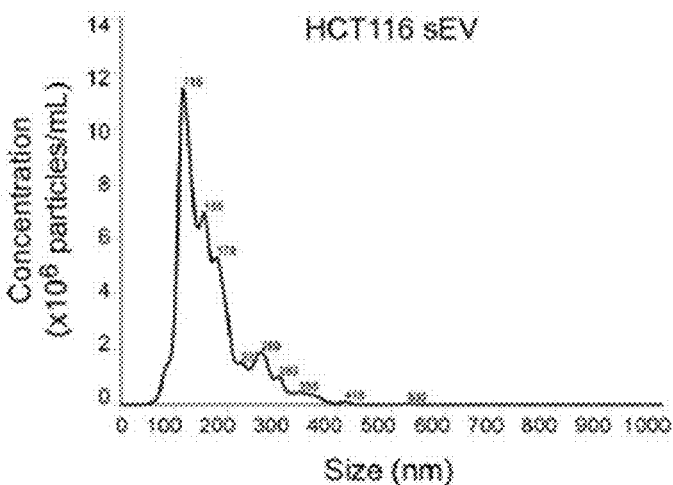
Figure 9B:
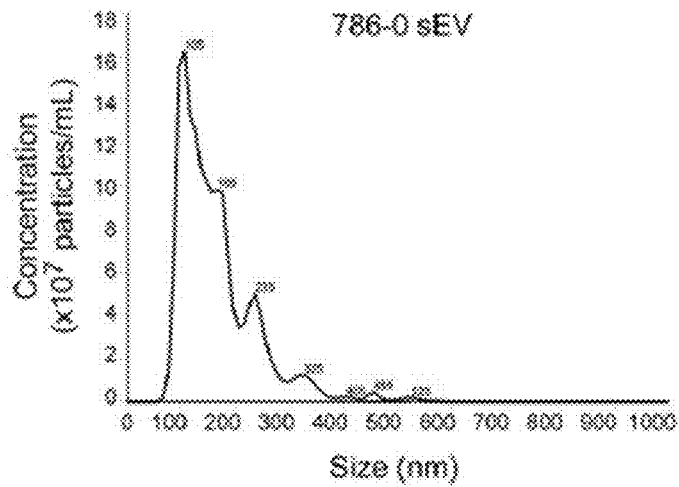
Figures 10A, 10B:
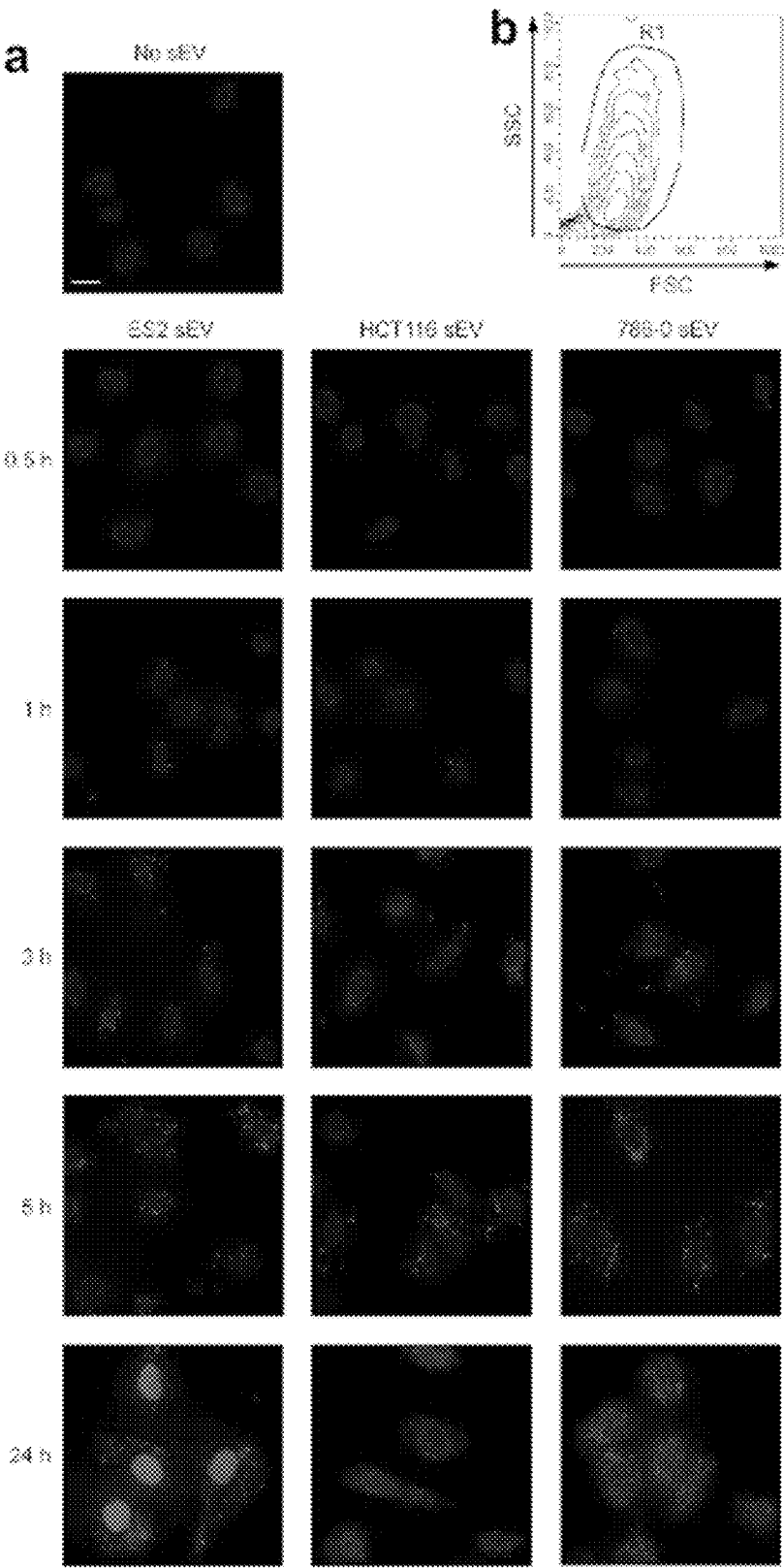
FIGS. 10A-10D. Kinetics of sEV uptake. HUVEC were evaluated for uptake of PKH26 dye-labeled sEVs of ES2, HCT116 and 786-0 cells at the indicated times.
Figure 10C:
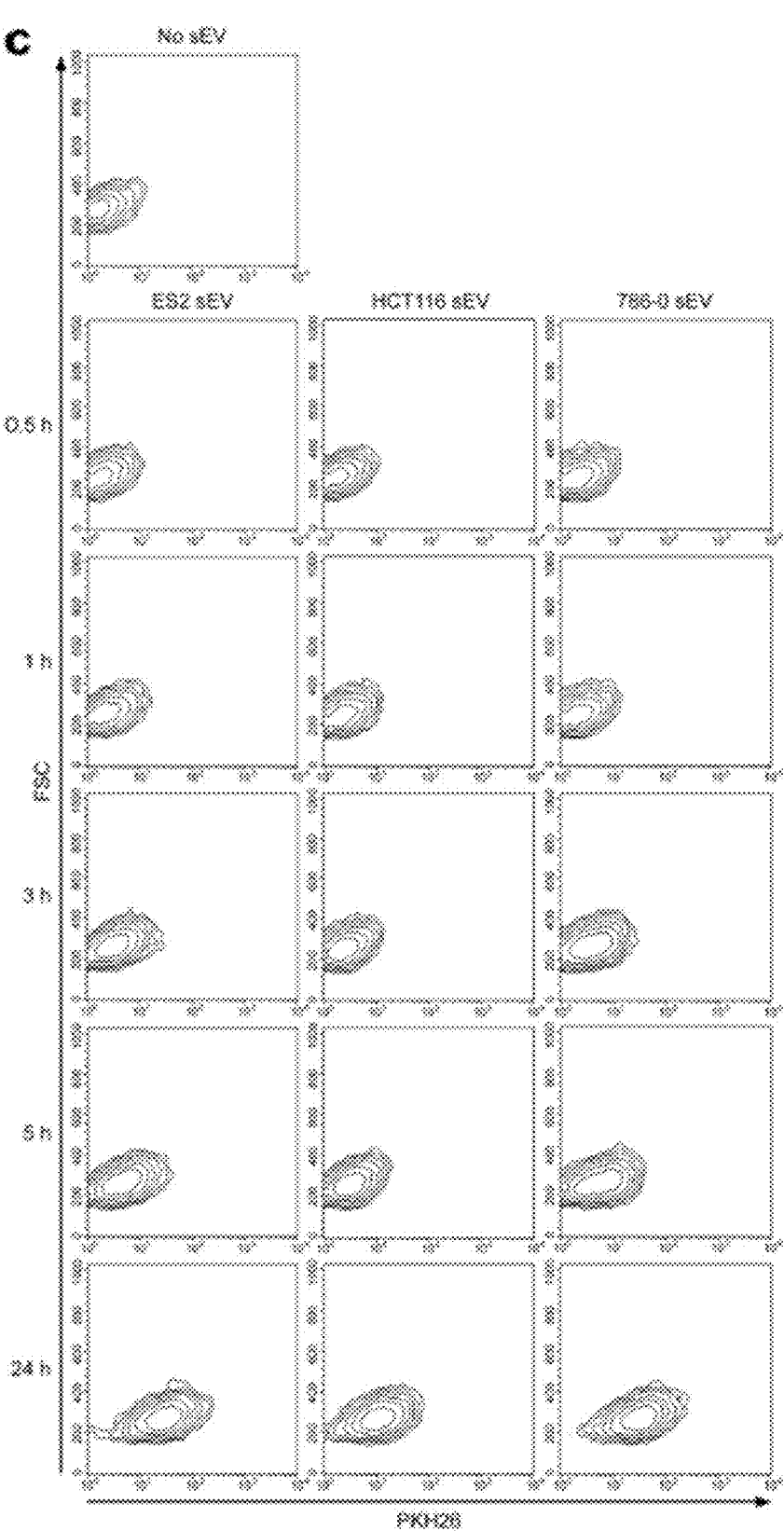
Figure 10D:
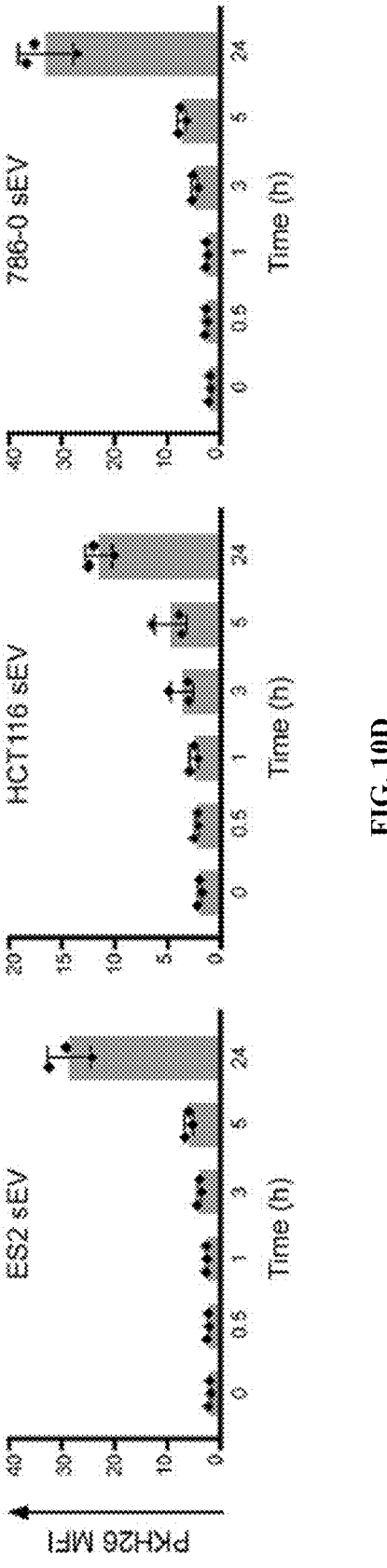
Figure 11A:
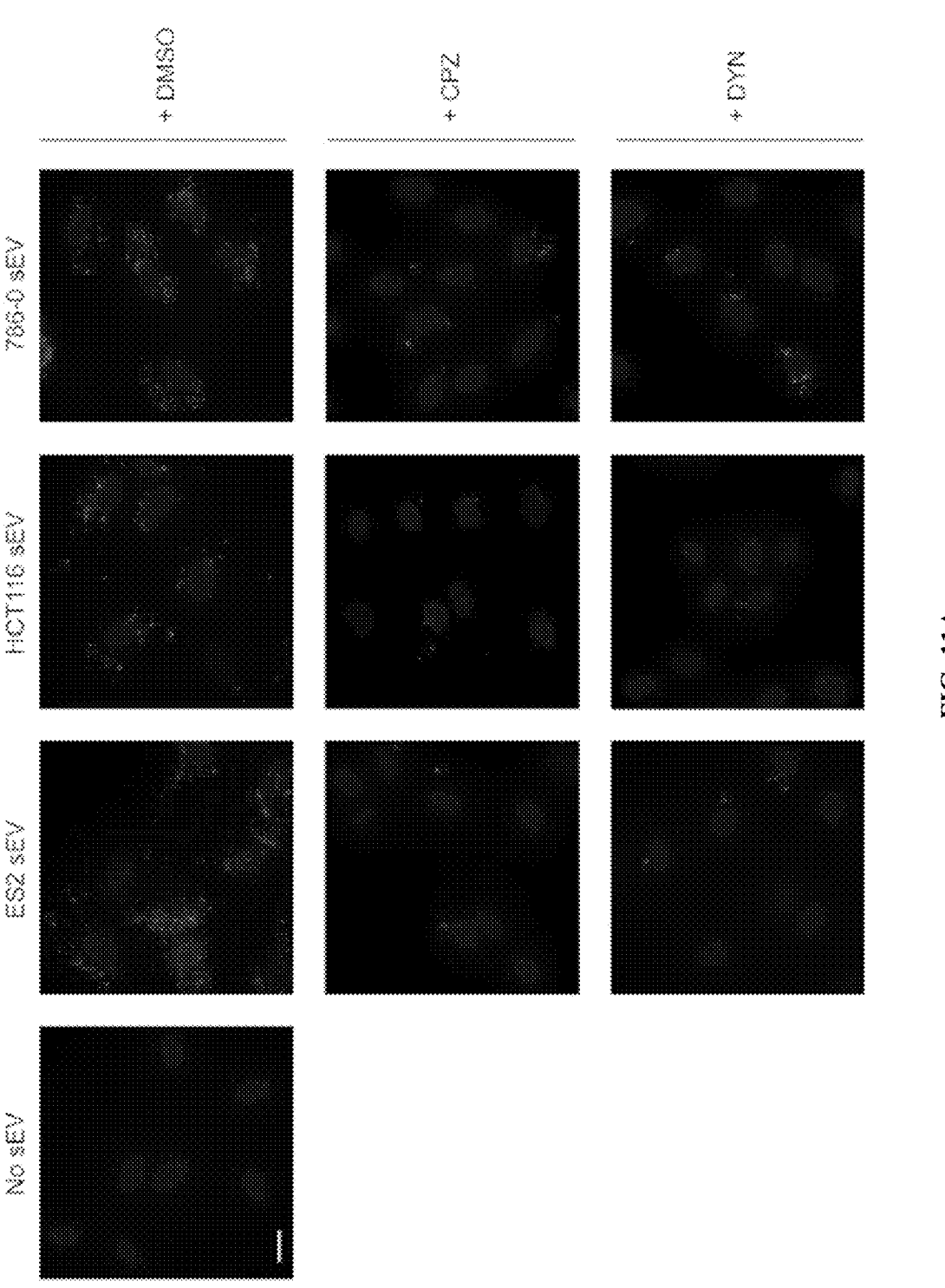
FIGS. 11A-11B. Blockade of sEV uptake. HUVEC were pretreated with endocytosis inhibitors (chlorpromazine, CPZ; dynasore, DIN or with dimethyl sulfoxide (DMSO) solvent, and then incubated with PKH26-labeled sEVs of ES2, HCT116 and 786-0 cells. Uptake of sEVs was evaluated at 5 h after addition of sEVs.
Figure 11B:
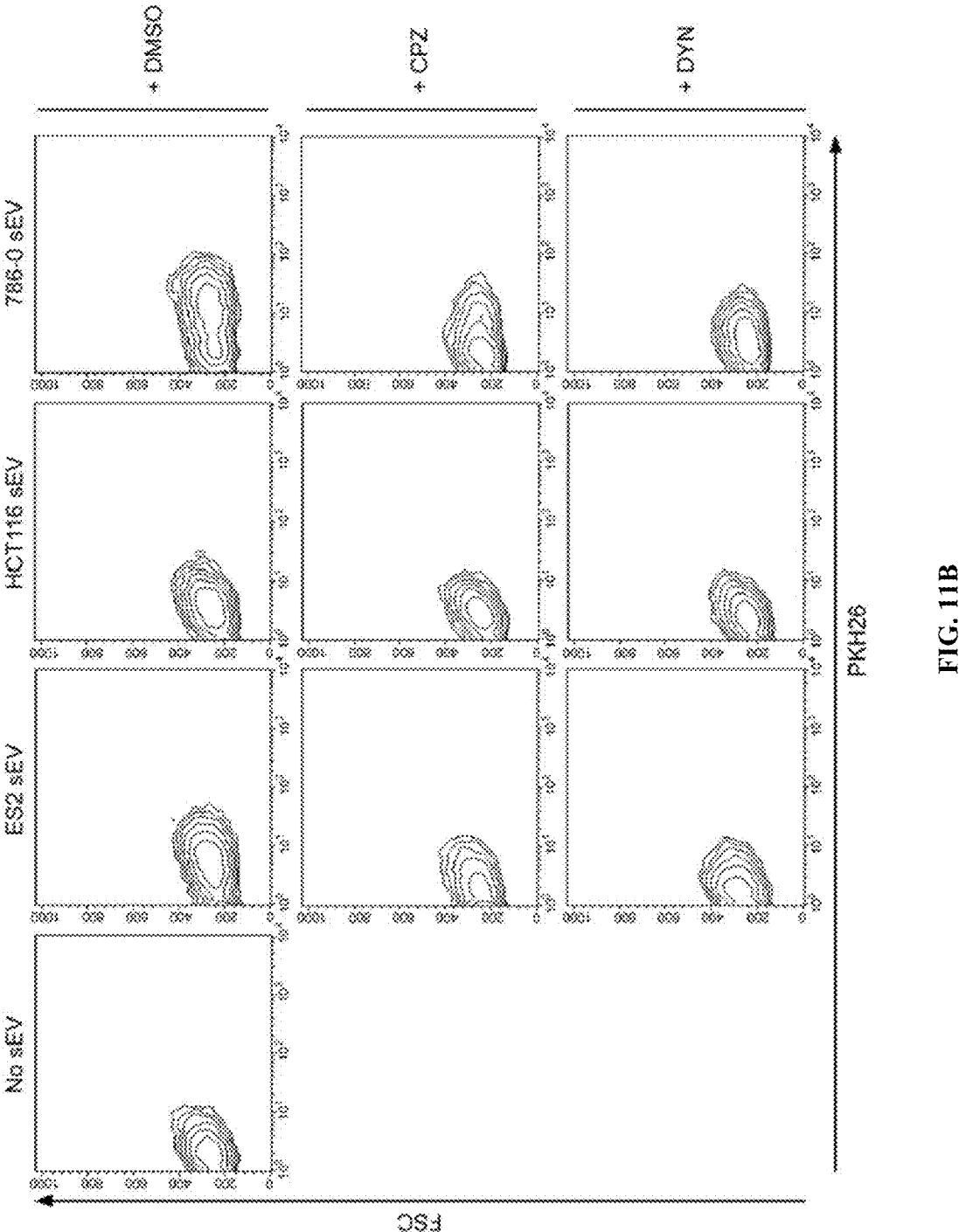

Unless noted otherwise, sEVs were isolated from culture media conditioned by ovarian, colorectal and renal cancer cell lines and from body fluids of tumor-bearing mice and cancer patients by sequential filtration to exclude particles of >200 nm in diameter and soluble proteins of <100 kD in size, followed by density gradient ultracentrifugation. Details of sEV isolation are described in Example 1. TSG101, a marker that is enriched in sEVs (Kowal et al., 2016), was exclusively detected in vesicles within the buoy-ant density range of sEVs (1.09 to 1.13 g/mL, termed 'sEV fractions') (FIG. 1A). Vesicles in sEV fractions also expressed flotillin-1, CD63 and HSP70 (FIGS. 1A,1B,9A) which are expressed in sEVs but not exclusively (Kowal et al., 2016). It was confirmed that vesicles in sEV fractions lacked α-actinin-4 and HSP90B1 (also known as GP96 or endoplasmin) which are mainly expressed in larger EVs (Kowal et al., 2016), and calnexin, a non-EV marker (Thery et al., 2018) (FIG. 9A). Vesicles in sEV fractions were also evaluated for purity, size and homogeneity by electron microscopy and nanoparticle tracking analysis and were within the size range of sEVs (FIGS. 1B,9B).

Following verification, sEVs were used to stimulate endothelial cells. sEVs induced cell migration and tube formation within 4 to 5 h (FIGS. 1C-1F). Uptake of sEVs was detected during this period but was modest (FIGS. 10A-10D), To test whether sEVs can induce endothelial cell migration and tube formation independently of uptake, endothelial cells were treated with endocytosis inhibitors to block sEV uptake. Because prolonged treatment with these inhibitors impairs cell motility, cells were treated for 4 to 5 h and migrating cells and tubes counted thereafter. Blockade of sEV uptake was confirmed by fluorescence microscopy and flow cytometry (FIGS. 1G,1H,11A,11B) and did not prevent sEVs from inducing endothelial cells to migrate and form tubes (FIGS. 1C-1F), These findings raise the possi-bility that cancer cell-derived sEVs can stimulate endothelial cell migration and tube formation via angiogenic proteins on the surface of sEVs rather than solely through transport of luminal cargo.

Example 3—VEGF is on the Surface of Cancer Cell-Derived sEVs

In an unbiased effort to identify angiogenic factors asso-ciated with sEVs, ovarian cancer cell-derived sEVs were screened using antibody (Ab) arrays. Several candidates including VEGF, growth-regulated oncogene-α (GROα), interleukin-8 (IL-8) and fibroblast growth factor-2 (FGF-2) were identified (FIG. 2A). Immunoassays were performed on lysates of sEVs secreted by ovarian (ES2), colorectal (HCT116) and renal (786-0) cancer cells to determine the total amount of each factor in sEVs. Equivalent amounts of intact sEVs were assayed to determine the amount of each factor on the surface of sEVs. In control assays, no or minimal TSG101 (a luminal constituent of sEVs) was detected on intact sEVs, whereas the amount of CD63 (a surface protein) detected on intact sEVs was equivalent to the total CD63 content in sEVs (FIG. 2B). VEGF was detected on intact sEVs of all 3 cancer cell lines and at amounts equivalent to the total VEGF content in these sEVs (FIG. 2B). These findings indicate that almost all of the sEV-VEGF is present on the surface.

Figure 2C:
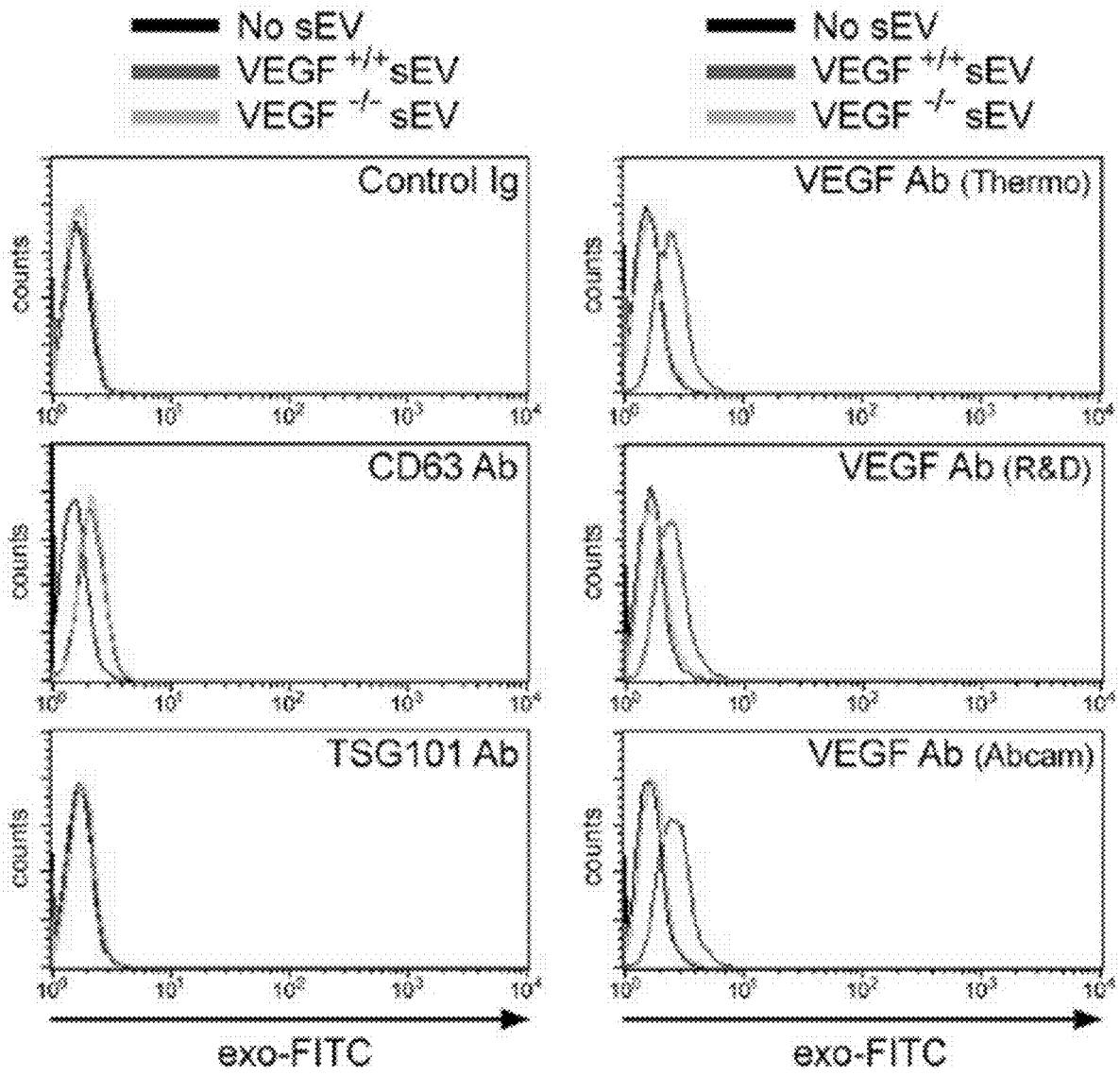
Figure 2D:
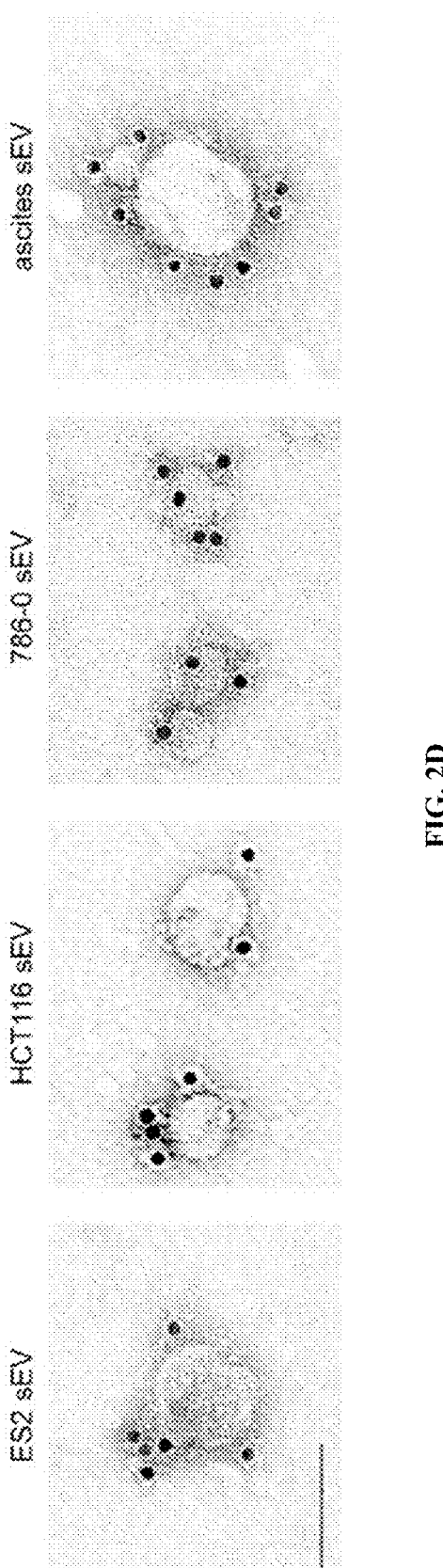
Figure 12A:
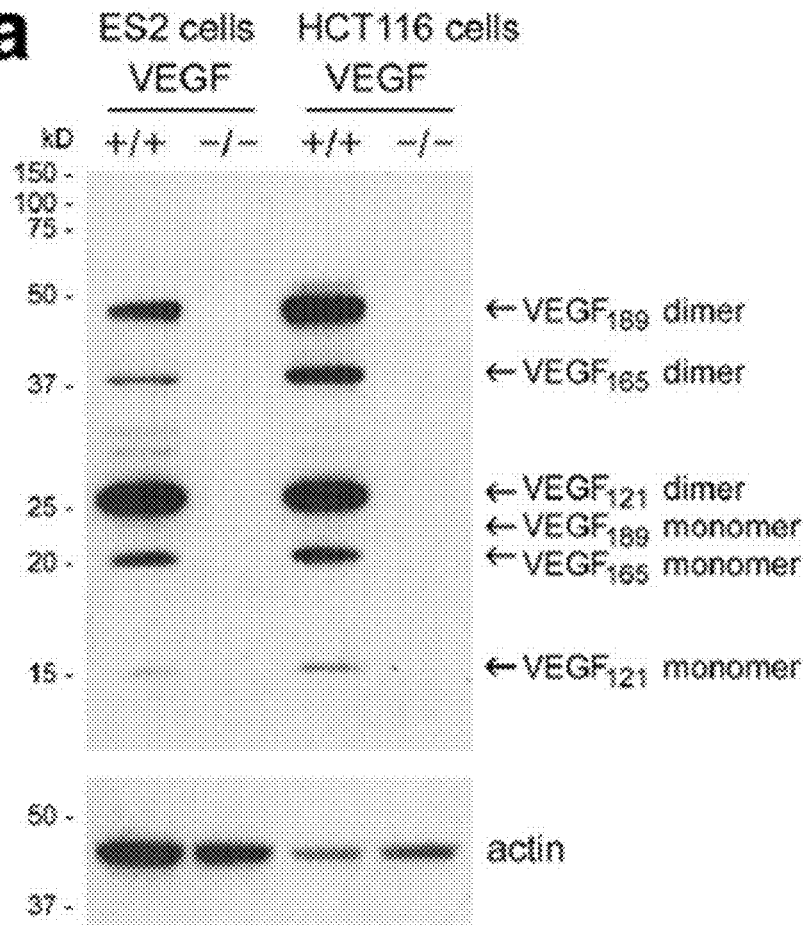
Figures 12B, 12C, 12D:
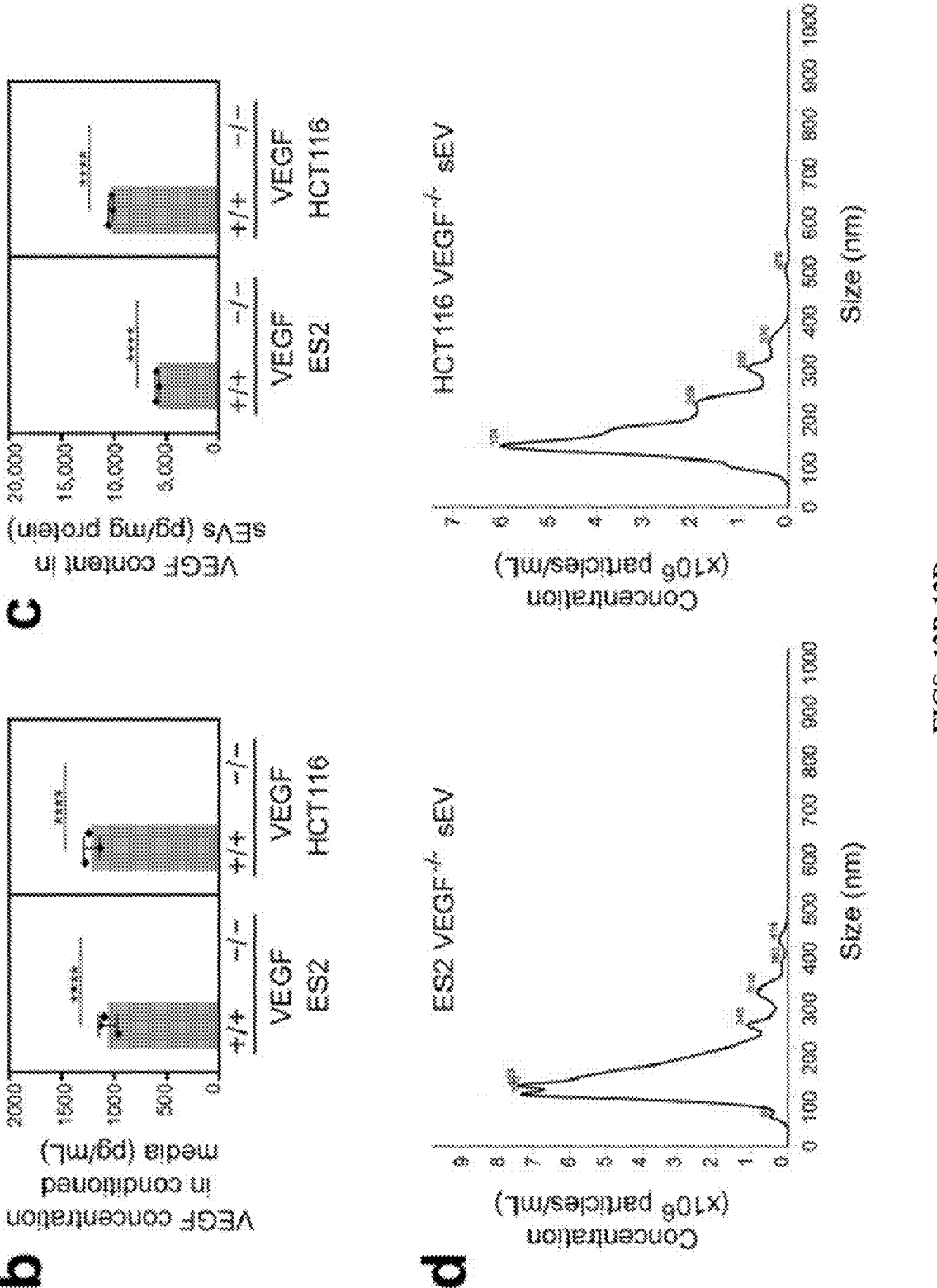
Figure 13A:
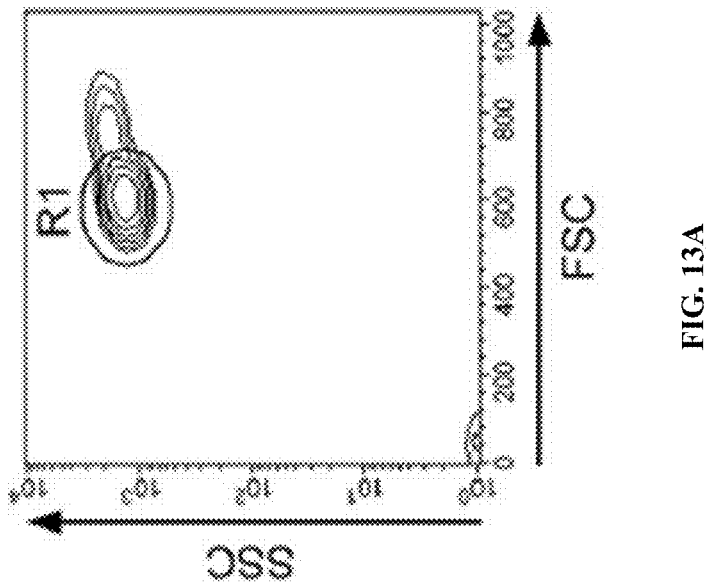
FIGS. 13A-13C, Detection of VEGF on the surface of cancer cell-derived sEVs by flow cytometric analysis of binding to Ab-coupled microbeads. Microbeads were coupled to the indicated Ab, incubated with no sEVs, sEVs of HCT116 VEGF$^{+/+}$ cells or sEVs of HCT116 VEGF$^{-/-}$ cells, and then stained with exo-FITC dye to label sEV membrane. Binding of Ab to protein on the surface of sEVs was detected by flow cytometric analysis of exo-FITC fluorescence in the gated population of Ab-coupled microbeads. Detection of VEGF was confirmed by using 3 different commercially available Ab to VEGF. CD63 and TSG101 were assayed as positive and negative controls for sEV surface protein, respectively.
Figure 13B:
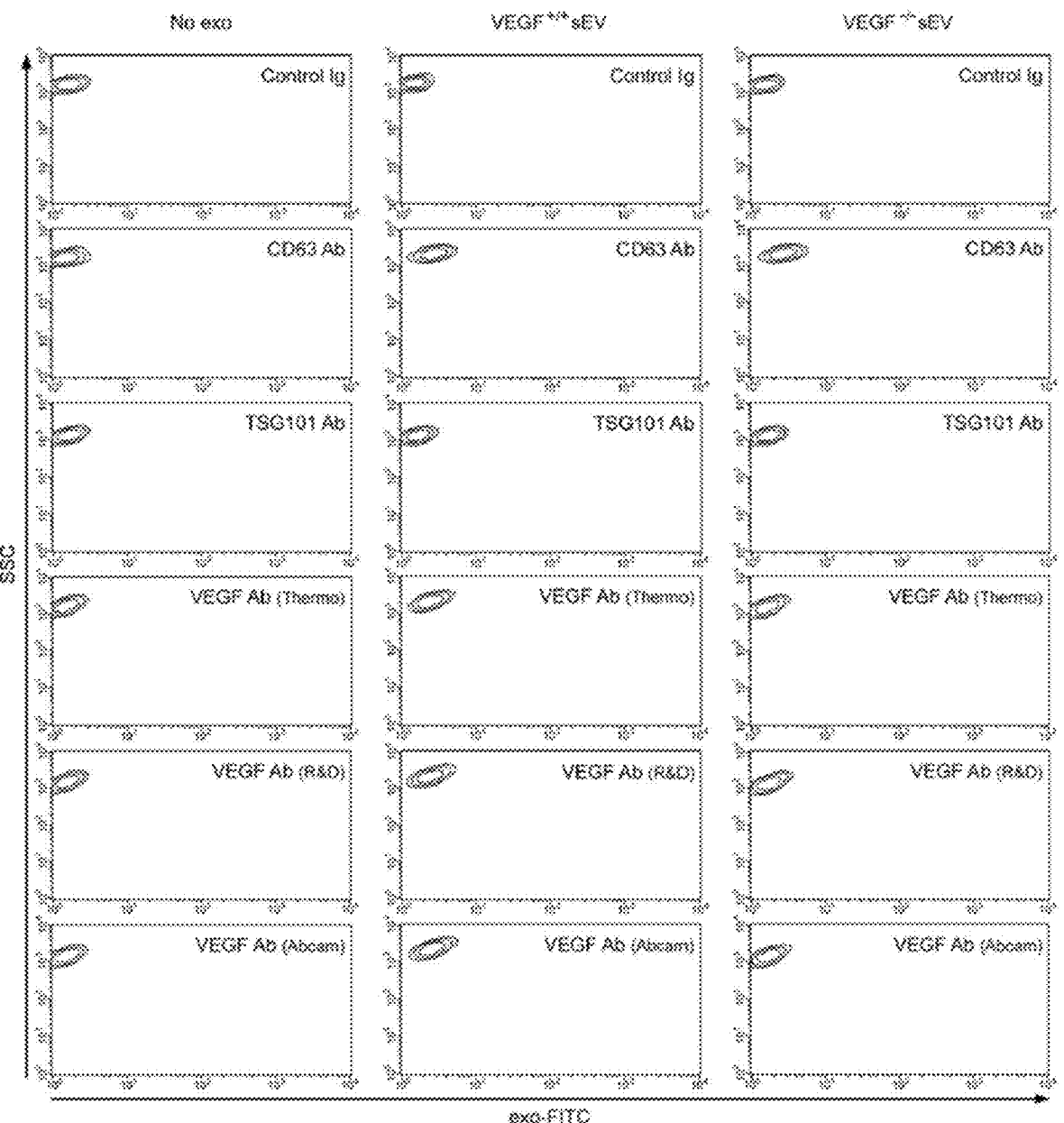
Figure 13C:
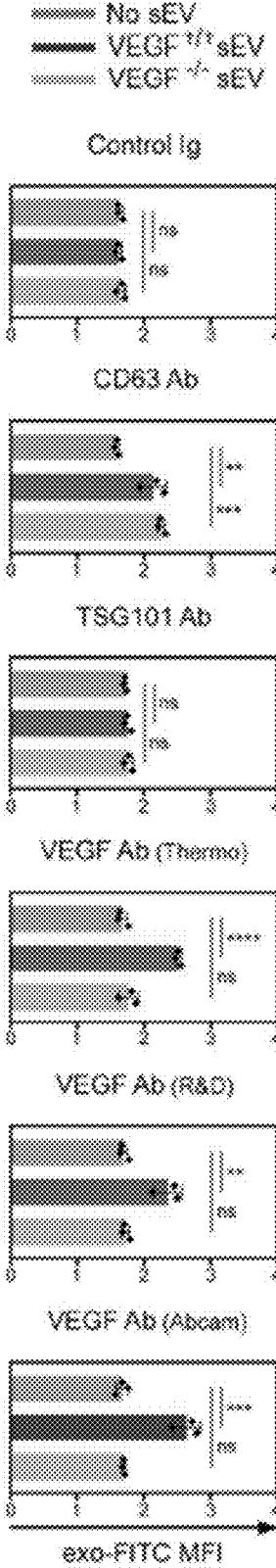
Figures 14A, 14B:
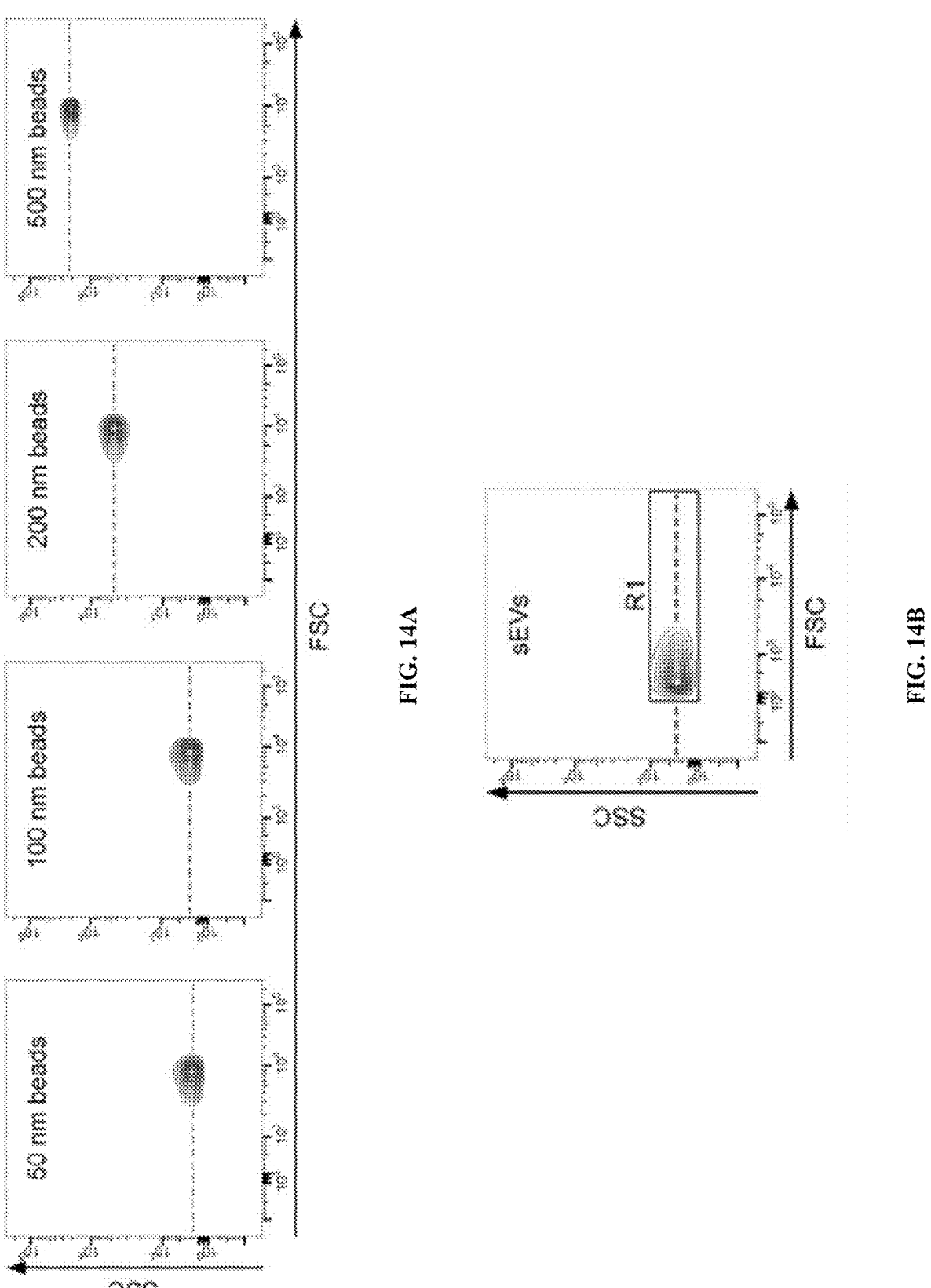
FIGS. 14A-14E. Detection of VEGF on the surface of cancer cell-derived sEVs by flow cytometric analysis of direct staining of sEVs.
Figure 14C:
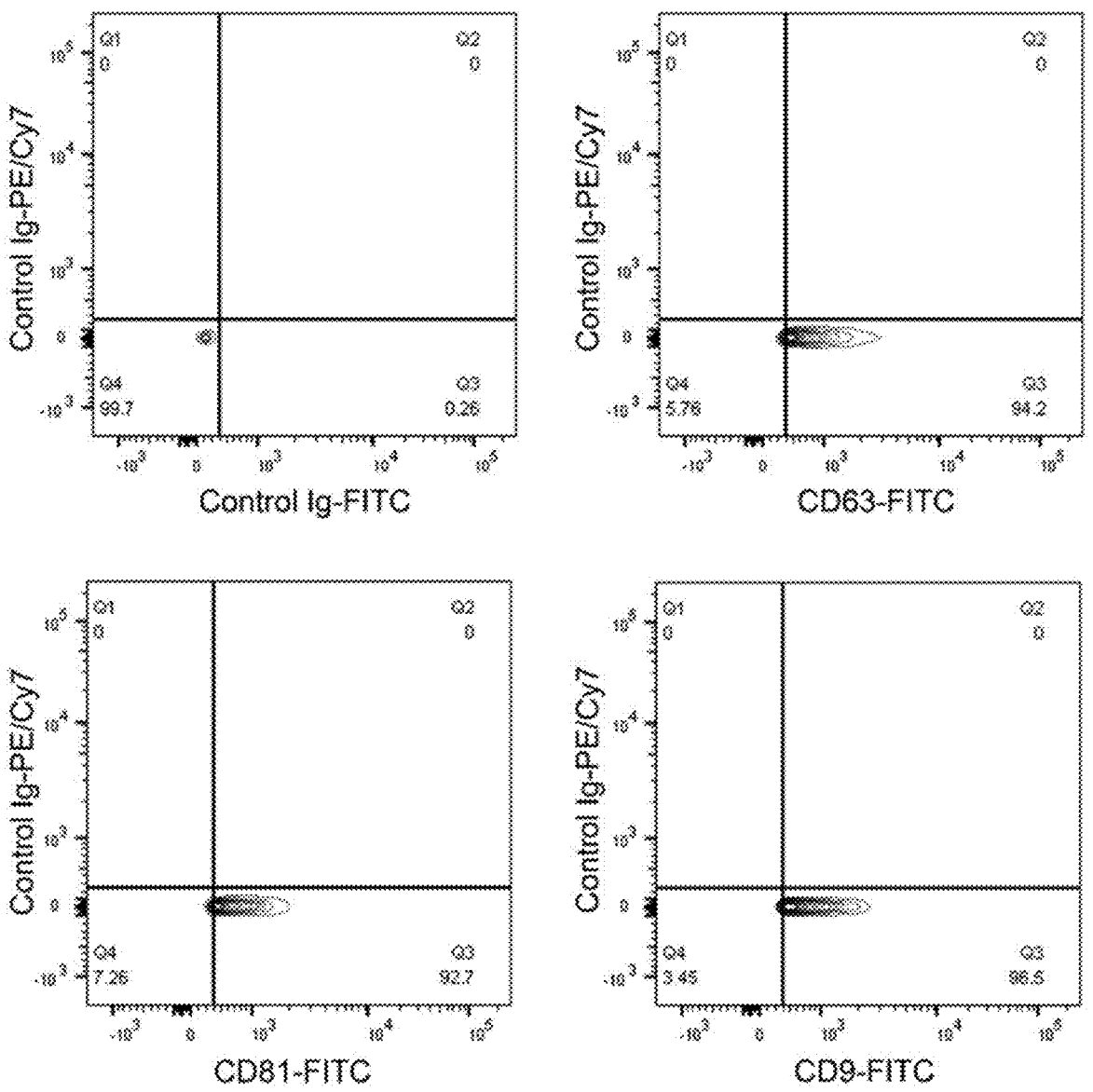
Figure 14D:
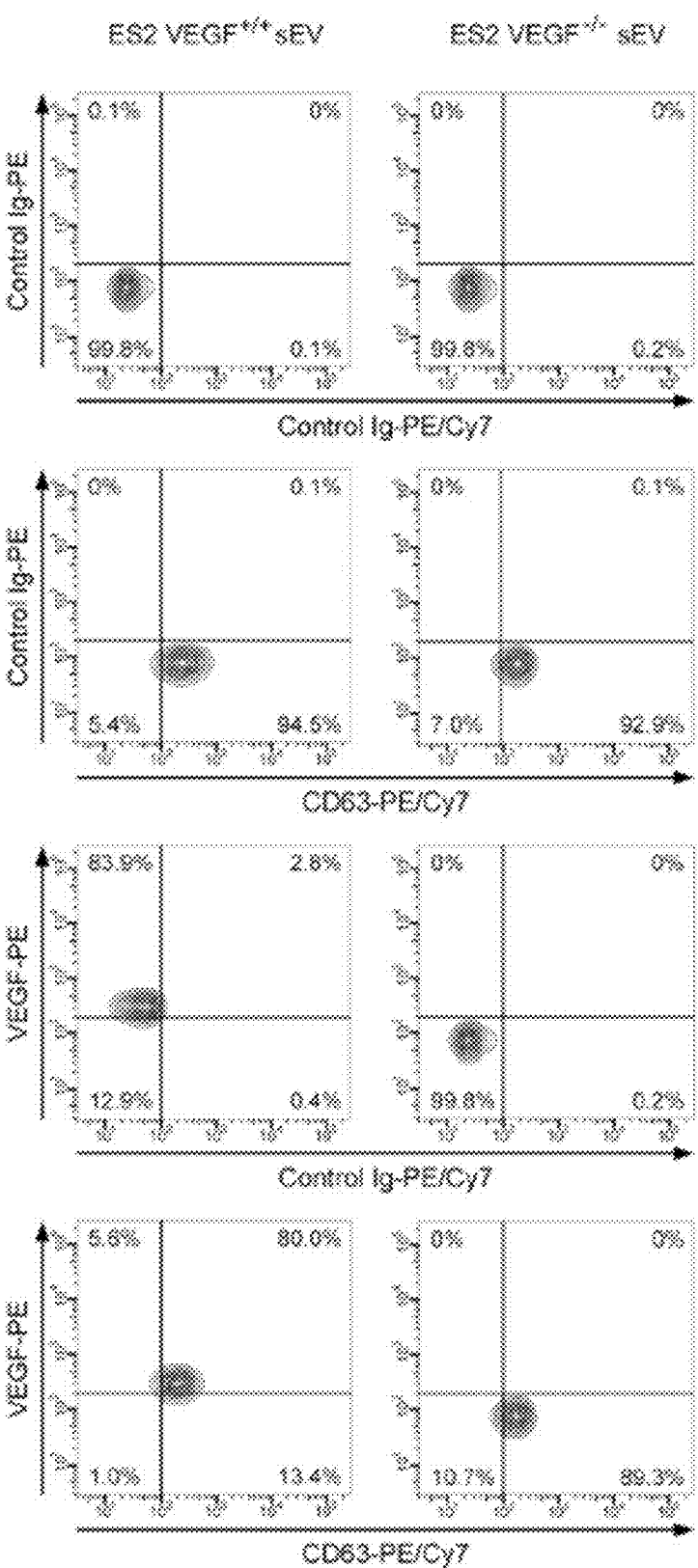
Figure 14E:
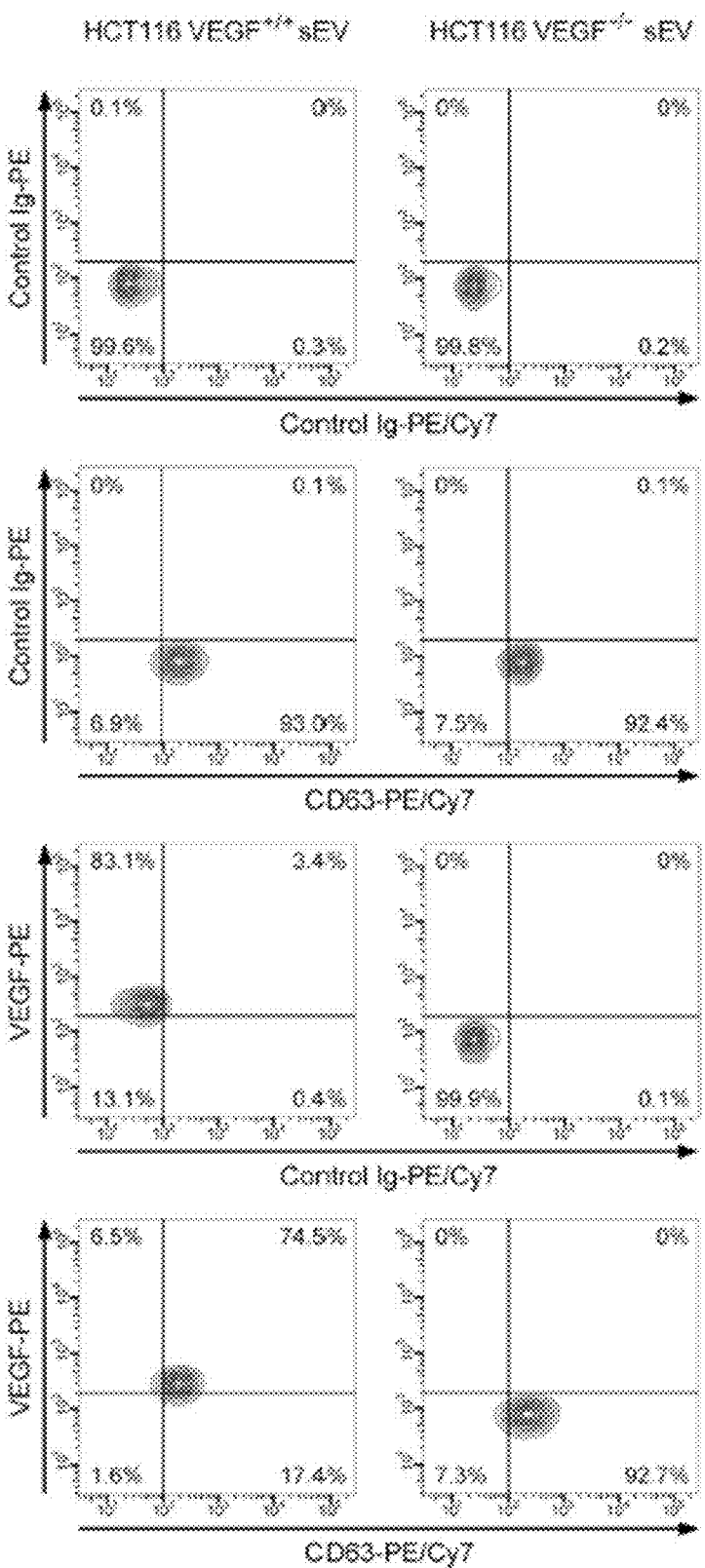

The presence of VEGF on the surface of sEVs was confirmed by two flow cytometric approaches. For negative controls, sEVs were isolated from a previously generated HCT116 VEGF$^{-/-}$ line (Dang et al., 2006) and from ES2 cells in which the VEGFA gene was deleted by CRISPR/Cas9 gene editing (FIGS. 12A-12C). sEVs of isogenic VEGF$^{+/+}$ and VEGF$^{-/-}$ lines were similar in size and homo-geneity (compare FIG. 9B and FIG. 12D). In the first approach, microbeads were coupled to VEGF Ab, incubated with sEVs and then stained with exo-FITC dye to label sEV membrane. Binding of Ab to VEGF on the surface of sEVs was evaluated by analyzing exo-FITC fluorescence in gated Ab-coupled microbeads. Gating strategy is shown in FIG. 13A. Using this approach, VEGF was detected on the surface of VEGF$^{+/+}$ sEVs but not on VEGF$^{-/-}$ sEVs. Results were reproduced using 3 different VEGF Ab (FIGS. 2C,13B, 13C). CD63 and TSG101 were assayed as positive and negative controls for sEV surface protein, respectively (FIGS. 2C,13B,13C). In the second approach, direct staining of sEVs with fluorochrome-conjugated Ab was evaluated in gated sEVs. Gating strategy is shown in FIGS. 14A,14B. To optimize settings for detecting proteins on the surface of sEVs by flow cytometry, sEVs were directly stained with fluorochrome-conjugated Ab to CD63, CD81 and CD9 which are proteins that are commonly present on the surface of sEVs (Koval et al, 2016) (FIG. 14C). By using this direct staining approach, CD63 was detected on approximately 90% of both VEGF$^{+/+}$ and VEGF$^{-/-}$ sEVs whereas VEGF was absent from VEGF$^{-/-}$ sEVs and detected on approxi-mately 80% of VEGF$^{+/+}$ sEVs (FIGS. 14D,14E). The pres-ence of VEGF on the sEV surface was confirmed by immunogold labeling (FIG. 2D).

Example 4—sEV-VEGF is Signaling-Competent

Figure 3A:
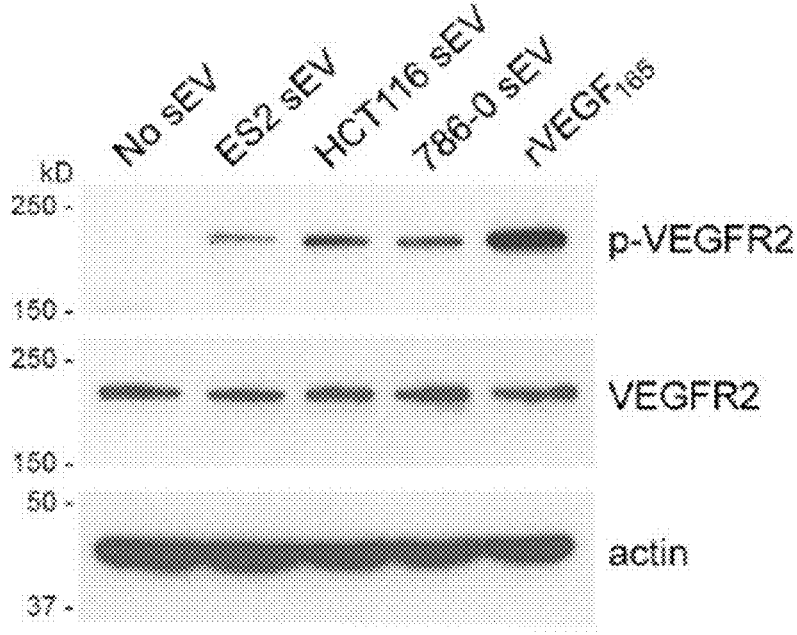
FIGS. 3A-3I. sEV-VEGF is signaling-competent.
Figure 3B:
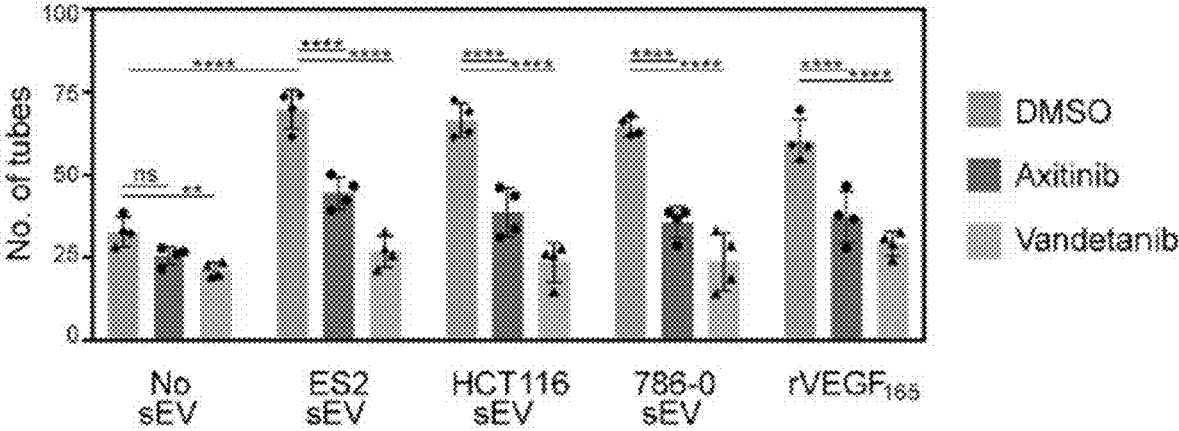
Figure 3C:
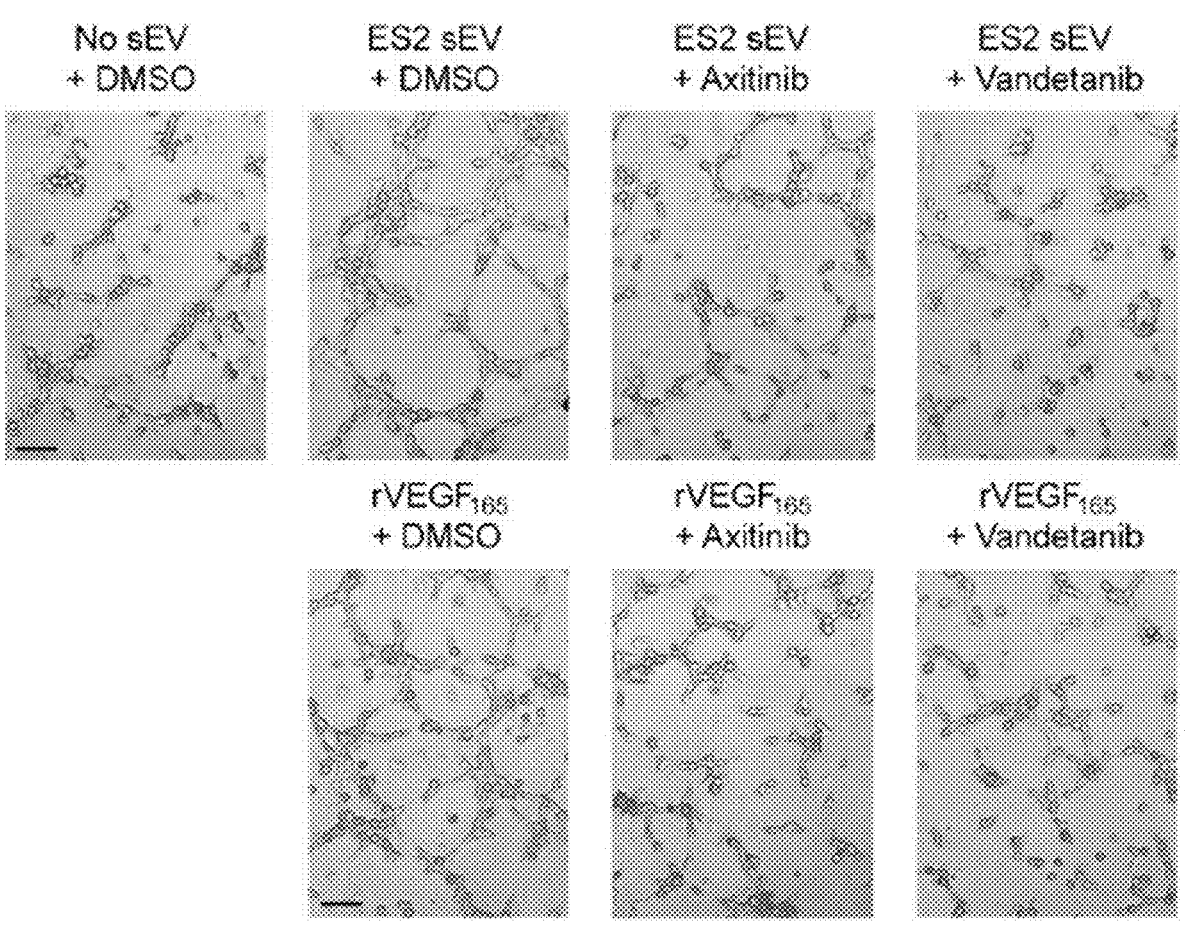
Figure 3D:
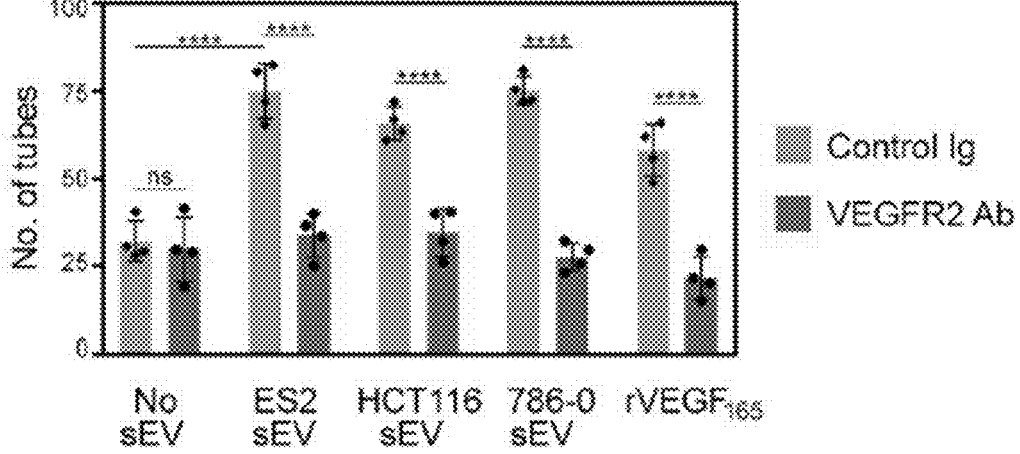
Figure 3E:
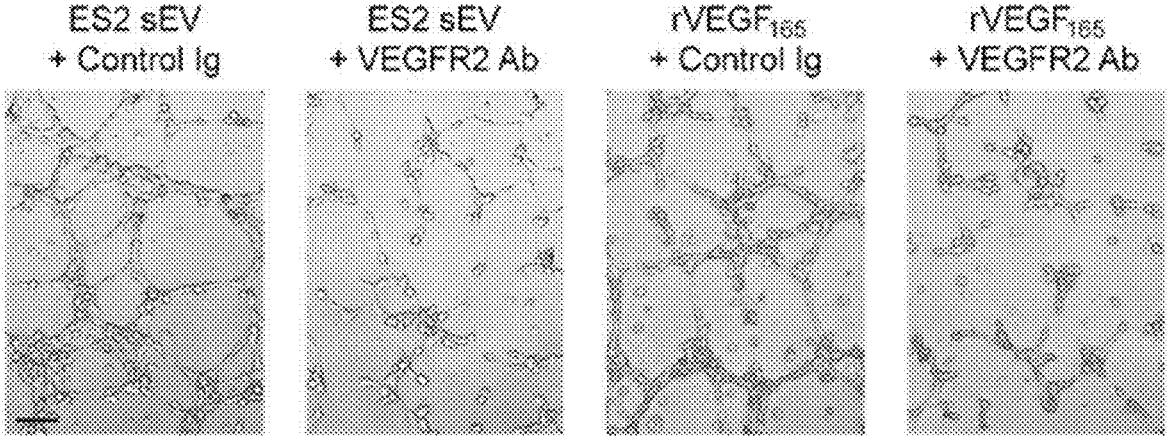

VEGF binds to and activates three related tyrosine kinase receptors (VEGFRs), of which VEGFR2 mediates the majority of the angiogenic effects of VEGF (Ferrara et al., 2003; Hicklin & Ellis, 2005). Phosphorylation of VEGFR2 was induced in endothelial cells following stimulation with cancer cell-derived sEVs (FIG. 3A). The sEV dose used (100 μg/mL) provided 500 to 2,000 μg/mL of sEV-VEGF (FIG. 2B). These concentrations of sEV-VEGF were within the range detected in body fluids of patients and mice with ovarian cancer (Table 1). Because VEGF$_{165}$ is the most commonly overexpressed VEGF isoform in tumors (Hicklin &. Ellis, 2005), recombinant VEGF$_{165}$ was used as a positive control and at a concentration within the physiological range (1,000 μg/mL). The ability of sEVs to stimulate tube formation was abrogated when endothelial cells were treated with agents that inhibit VEGFR tyrosine kinase activity (P<0.0001) (FIGS. 3B,3C) or with an Ab to VEGFR2 that blocks ligand binding (P<0.0001) (FIGS. 3D,3E). These findings indicate that signaling-competent VEGF is present on the surface of cancer cell-derived sEVs, and that sEV-VEGF interacts with the extracellular domain of VEGFR2 on target cells.

Figures 3F, 3G:
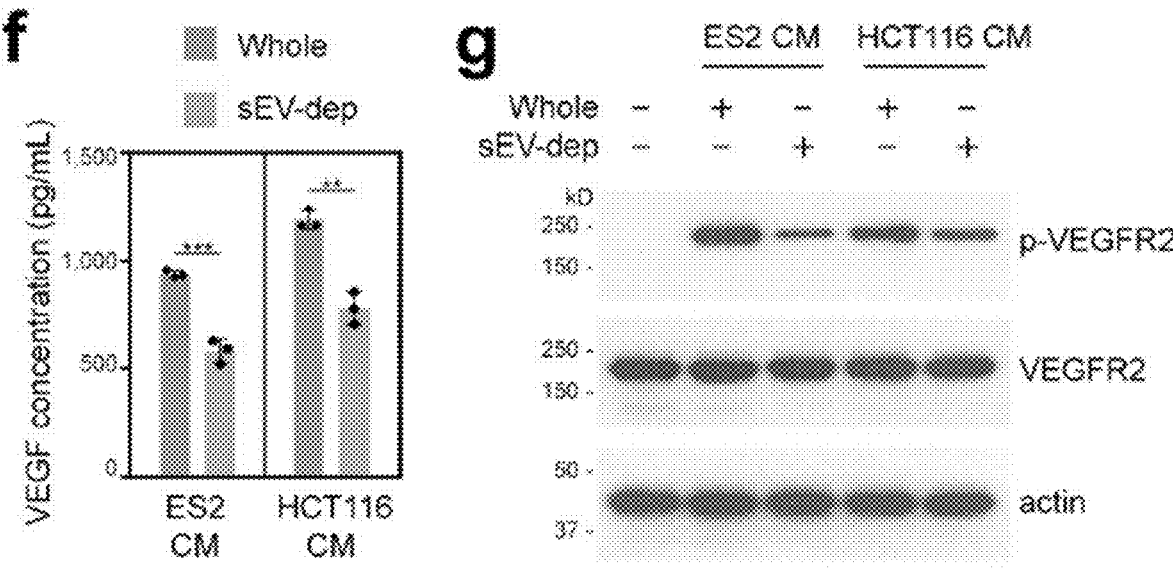
Figures 3H, 3I:
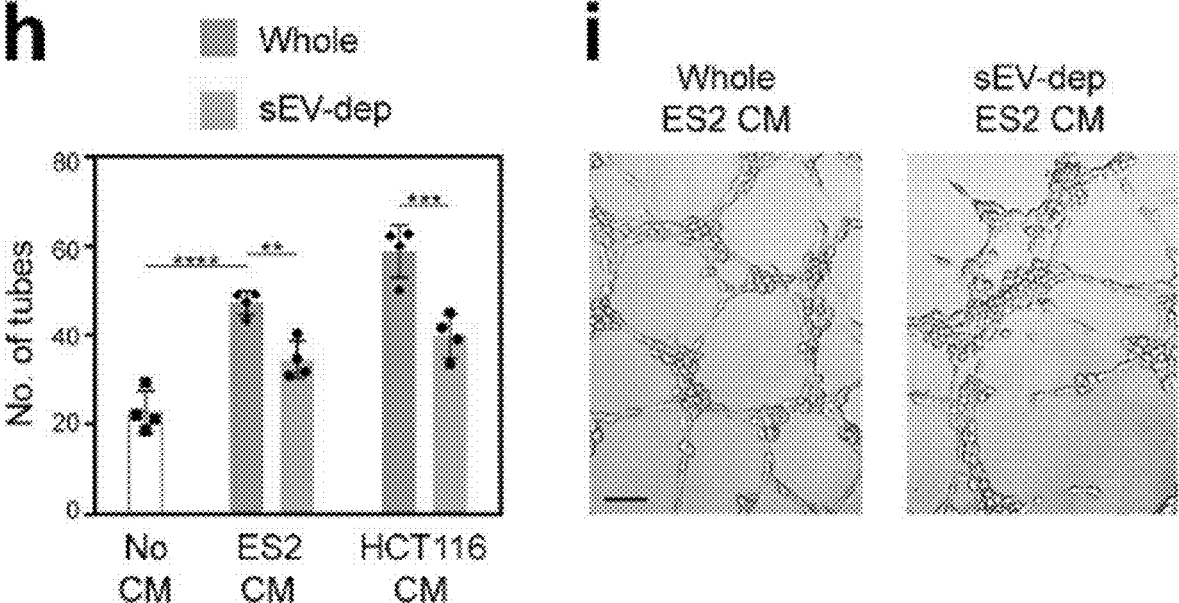

It was subsequently determined how much of the total VEGF in body fluids comprises of sEV-VEGF. Samples of ascites from patients with ovarian cancer were depleted of sEVs or left non-depleted, and then assayed for VEGF. The differences between VEGF levels in whole and sEV-depleted samples revealed that 24% to 38% of the total VEGF in patient ascites comprises of sEV-VEGF (Table 1). Also, ascites was collected from nude mice bearing human ovarian tumor xenografts (FIG. 15A), and whole and sEV-depleted samples were assayed for human (i.e. tumor-derived) VEGF. sEV-VEGF constituted 18% to 34% of tumor-derived VEGF in mouse ascites (Table 1). Analysis of purified sEVs by human- and mouse-specific VEGF immunoassays revealed that the vast majority of sEV-VEGF in mouse ascites derived from tumors and not the host (FIG. 15B). Furthermore, analysis of VEGF levels in whole and sEV-depleted cancer cell-conditioned media revealed that sEV-VEGF constitutes approximately 35% of the total VEGF secreted by cancer cells (FIG. 3F). By comparing the effects of stimulating endothelial cells with whole and sEV-depleted media, it was found that depletion of sEVs reduced VEGFR2 phosphorylation (FIG. 3G) and decreased tube formation by 30% (FIGS. 3H,3I).

TABLE 1

Abundance of sEV-VEGF in ascites of
women and mice with ovarian cancer

| | | VEGF in whole ascites (pg/mL)[‡] | VEGF in sEV-depleted ascites (pg/mL)[‡] | Estimated sEV-VEGF in ascites (pg/mL)[§] |
|---|---|---|---|---|
| Ovarian | P1 | 2,313 | 1,435 | 878 (38.0%) |
| cancer | P2 | 1,098 | 768 | 330 (30.1%) |
| patient | P3 | 4,056 | 3,098 | 958 (23.6%) |
| ascites* | P4 | 1,837 | 1,362 | 475 (25.9%) |
| | P5 | 1,930 | 1,379 | 551 (28.5%) |
| | P6 | 1,118 | 708 | 410 (36.7%) |
| Ascites | M1 | 12,909 | 10,532 | 2,377 (18.4%) |
| from | M2 | 12,302 | 9,230 | 3.072 (25.0%) |
| mouse | M3 | 13,807 | 11,025 | 2.782 (20.1%) |
| xenograft | M4 | 8,724 | 5,727 | 2,997 (34.3%) |
| models[†] | M5 | 13,187 | 9,925 | 3,262 (24.7%) |
| | M6 | 10,962 | 8,876 | 2,086 (19.0%) |

*Clinical specimens of ascites from 6 women with Stage III high-grade serous ovarian carcinoma
[†]Ascites from 6 female nude mice, collected at 3 weeks following i.p. injection of ES2 human ovarian cancer cells
[‡]Assayed by ELISA. Shown is the mean of 2 independent assays of each ascites sample.
[§]Estimated from differences between VEGF levels in whole and sEV-depleted ascites samples
Proportion shown as % of VEGF in whole ascites in parentheses

Example 5—Effects of sEVs on Endothelial Cells Depend on VEGF

Figures 4A, 4B, 4C:
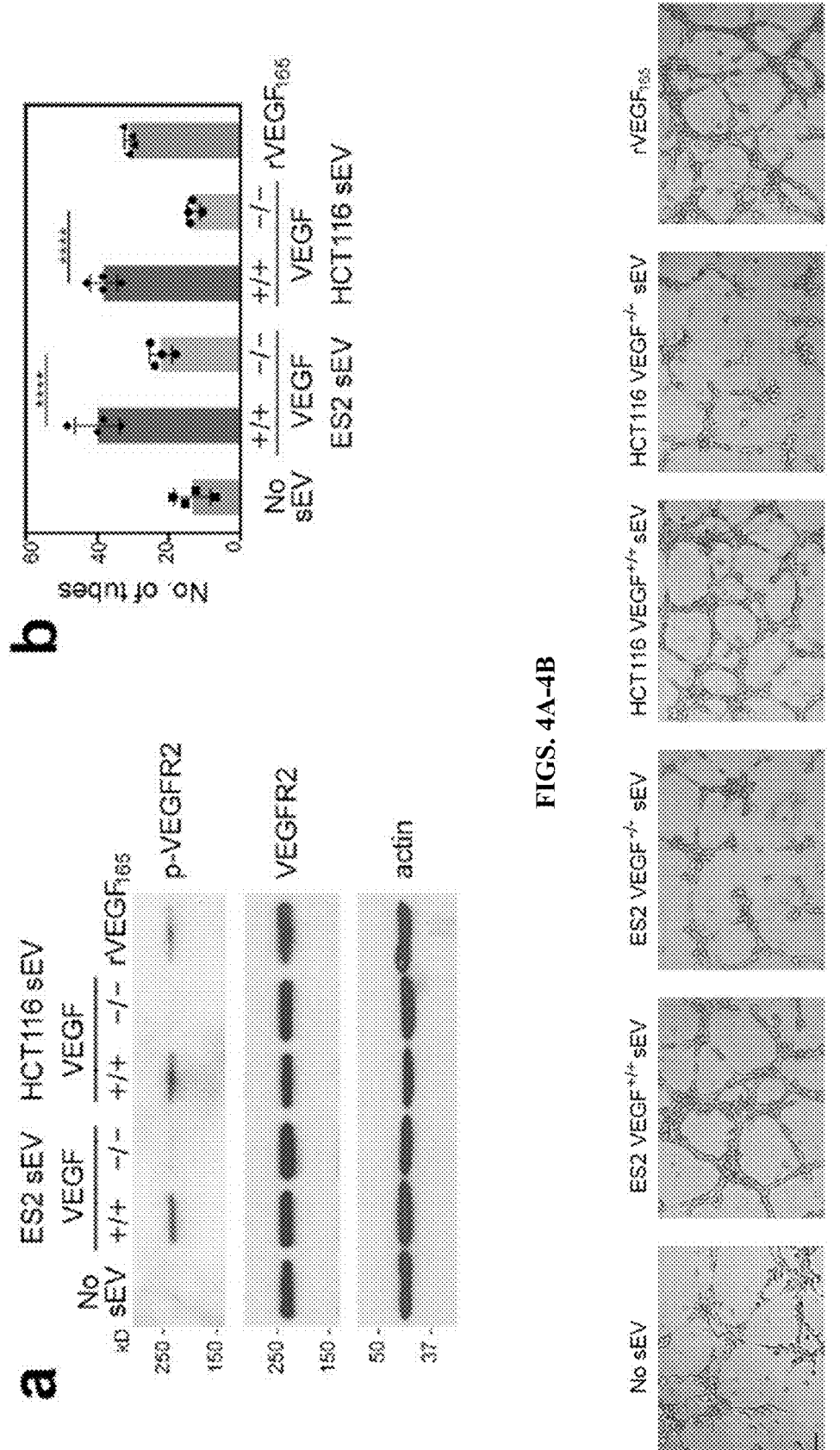
FIGS. 4A-4F. Stimulatory effects of cancer cell-derived sEVs on endothelial cells and tumor growth depend on VEGF.
Figures 4D, 4E:
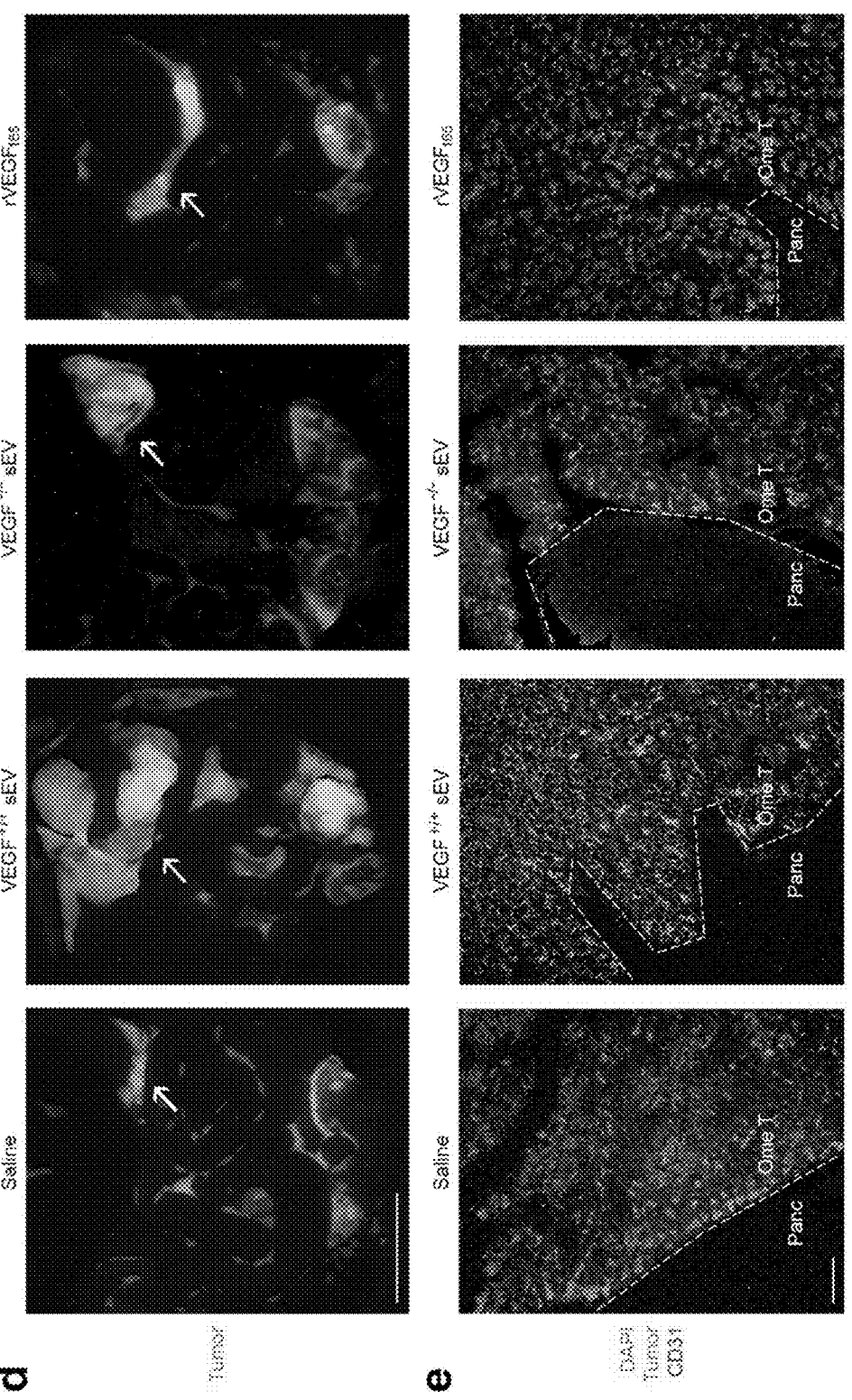
Figure 4F:
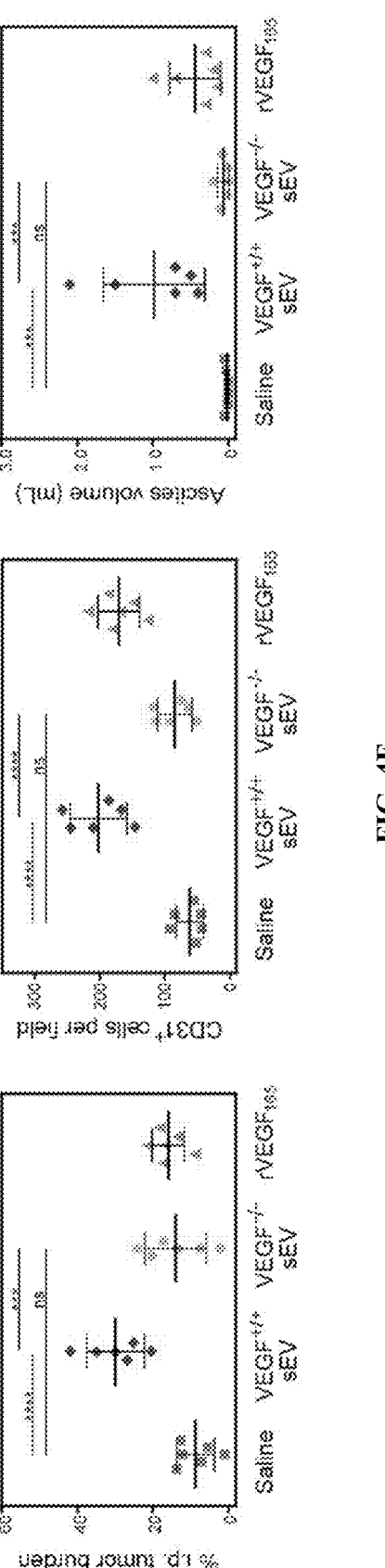

To determine whether the stimulatory effects of cancer cell-derived sEVs on endothelial cells are mediated by VEGF, responses to sEVs of isogenic VEGF$^{+/+}$ and VEGF$^{-/-}$ cancer cells were evaluated. In contrast to sEVs of VEGF$^{+/+}$ cells, sEVs of VEGF$^{-/-}$ cells neither induced VEGFR2 phosphorylation (FIG. 4A) nor significantly stimulated tube formation (FIGS. 4B,4C). To confirm these findings in vivo, nude mice were injected i.p. with ES2 VEGF$^{-/-}$ cells and, at one week thereafter when tumors were palpable, were randomized into groups. Groups were administered equivalent amounts of sEVs of ES2 VEGF$^{+/+}$ cells or sEVs of ES2 VEGF$^{-/-}$ cells over the following 2 weeks. The sEV dose was determined from the volume of ascites and amount of tumor-derived sEV-VEGF in ascites that forms in mice at 3 weeks following i.p. injection of ES2 VEGF$^{+/+}$ cells (FIGS. 15A,15B). When compared to saline-treated mice, tumor burden and numbers of intratumoral endothelial cells were increased in mice that had been administered VEGF$^{+/+}$ sEVs (P<0.0001) but not in mice that had been administered VEGF$^{-/-}$ sEVs (FIGS. 4D-4F). VEGF induces ascites by stimulating vascular permeability (Nagy et al., 1995). Notably, ascites was induced in mice by VEGF$^{+/+}$ sEVs (P<0.001) but not by VEGF$^{-/-}$ sEVs (FIG. 4F). These findings demonstrate that sEV-VEGF is biologically active in vivo and that the stimulatory effects of cancer cell-derived sEVs on endothelial cells and tumor growth depend on VEGF.

Example 6—sEV-VEGF Predominantly Comprises of Dimeric VEGF$_{189}$

VEGF has been detected in cancer cell-derived sEVs (Skog et al., 2008; Treps et al., 2017; Zhao et al., 2018), but the molecular characteristics of the sEV form of VEGF and the mechanism by which VEGF associates with sEVs have not been delineated. Alternative splicing of VEGFA mRNA yields several VEGF isoforms of which the 121, 165, 189 and 206 amino acid variants are the most common (Ferrara et al., 2003). VEGF$_{121}$ and the other common isoforms all contain exons 1 to 5 and exon 8; and the larger isoforms additionally contain exons 6 and/or 7 that encode heparin-binding domains (Ferrara et al., 2003). VEGF$_{121}$ is freely secreted, VEGF$_{189}$ and VEGF$_{206}$ are membrane-bound, and VEGF$_{165}$ exists in both soluble and membranous forms (Ferrara et al., 2003). All of the VEGF isoforms are biologically active as homodimers (Pötgens et al., 1994). Monomers of VEGF$_{121}$ and VEGF$_{165}$ and dimers of VEGF$_{121}$, VEGF$_{165}$ and VEGF$_{189}$ were detected at various ratios in cells of ovarian, colorectal and renal cancer lines (FIG. 5A). In contrast, sEVs secreted by these cells were enriched with VEGF$_{189}$ dimers (FIG. 5B). To eliminate the possibility that the presence of VEGF resulted from contamination during ultracentrifugation, all fractions were assayed for VEGF. VEGF was detected in the highest density fractions that largely consisted of unfractionated and/or soluble material, and this VEGF comprised of VEGF$_{121}$ and VEGF$_{165}$ but not VEGF 189 (FIGS. 16A, 16B). Of the other fractions; only the fractions of the density of sEVs showed prominent levels of VEGF and this VEGF comprised of dimeric VEGF$_{189}$ (FIGS. 16A,16B). To confirm that VEGF$_{189}$ is preferentially enriched in sEVs, clinical specimens were evaluated. Multiple isoforms of VEGF were detected at various ratios in ovarian tumor tissues, but dimeric VEGF$_{189}$ was the predominant species in sEVs isolated from body fluids of the same patients (FIG. 5C). $VEGF_{189}$ was also the most abundant isoform of VEGF in sEVs isolated from body fluids of patients with colorectal or renal cancers (FIG. 5D).

Example 7—sEV-VEGF is Heparin-Bound and Highly Stable

Figure 6A:
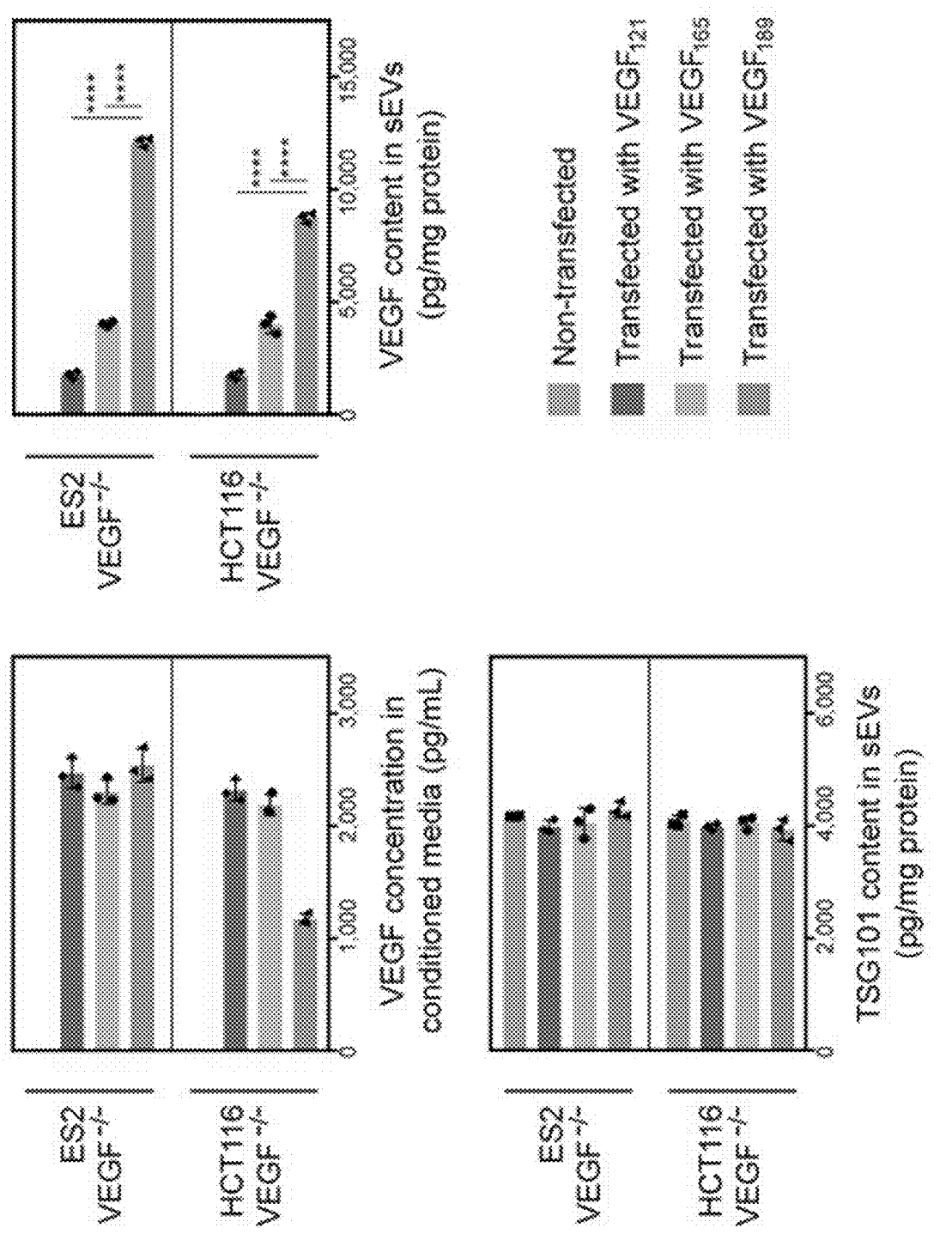
FIGS. 6A-6H. Selective localization of VEGF$_{189}$ in sEVs is mediated by heparin-binding and increases ligand stability.
Figures 6B, 6C:
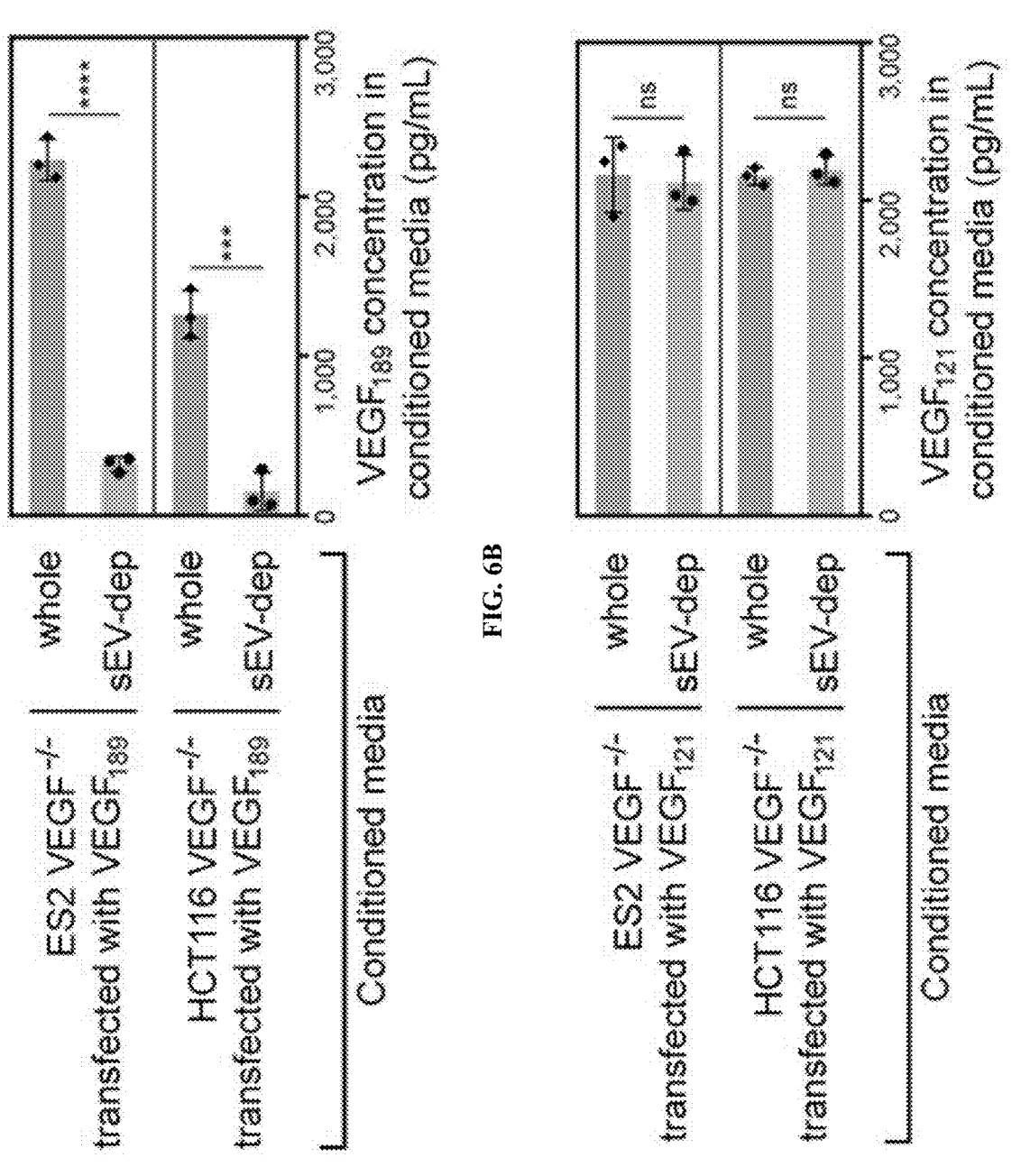
Figures 6D, 6E:
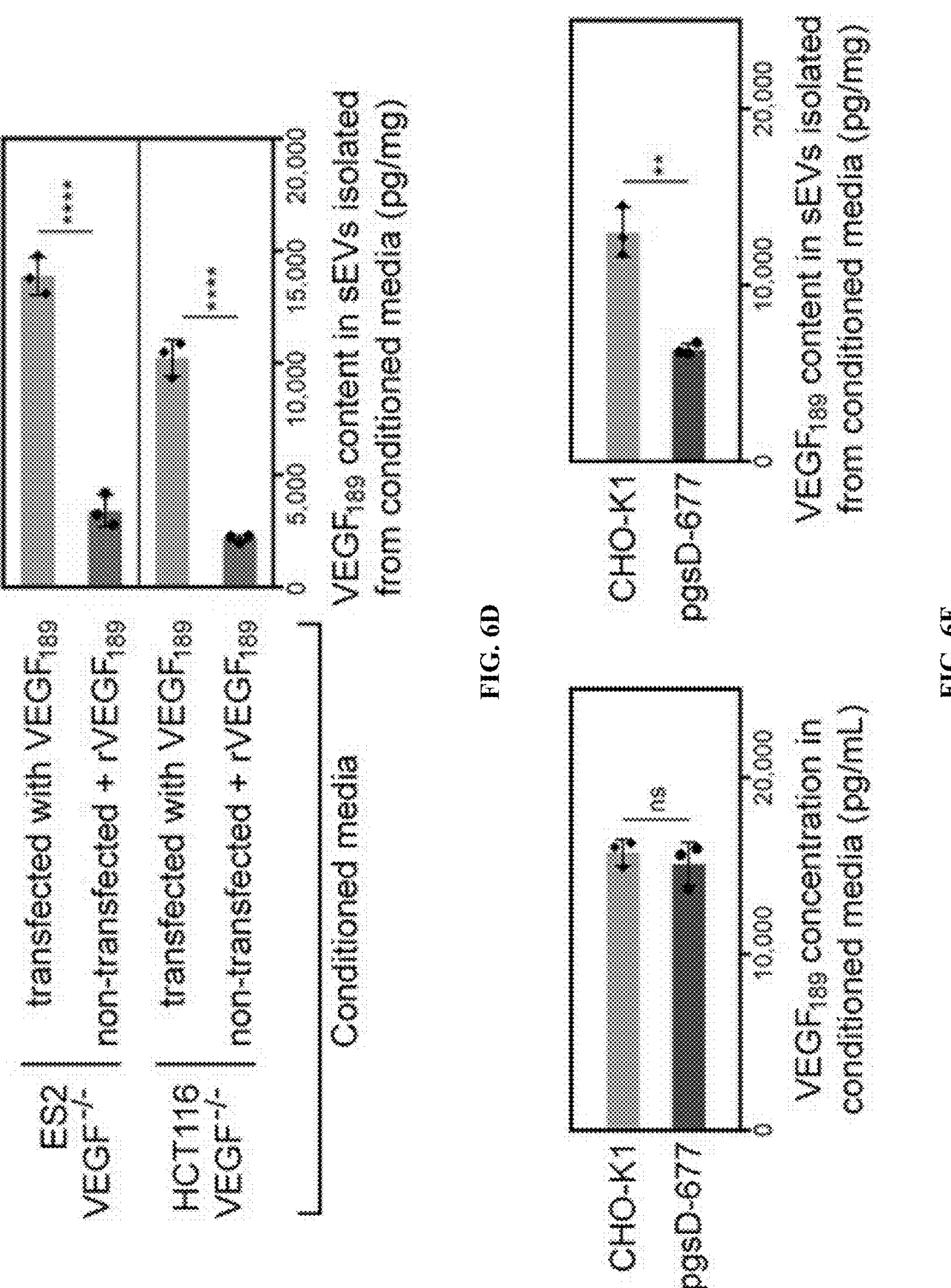
Figure 6F:
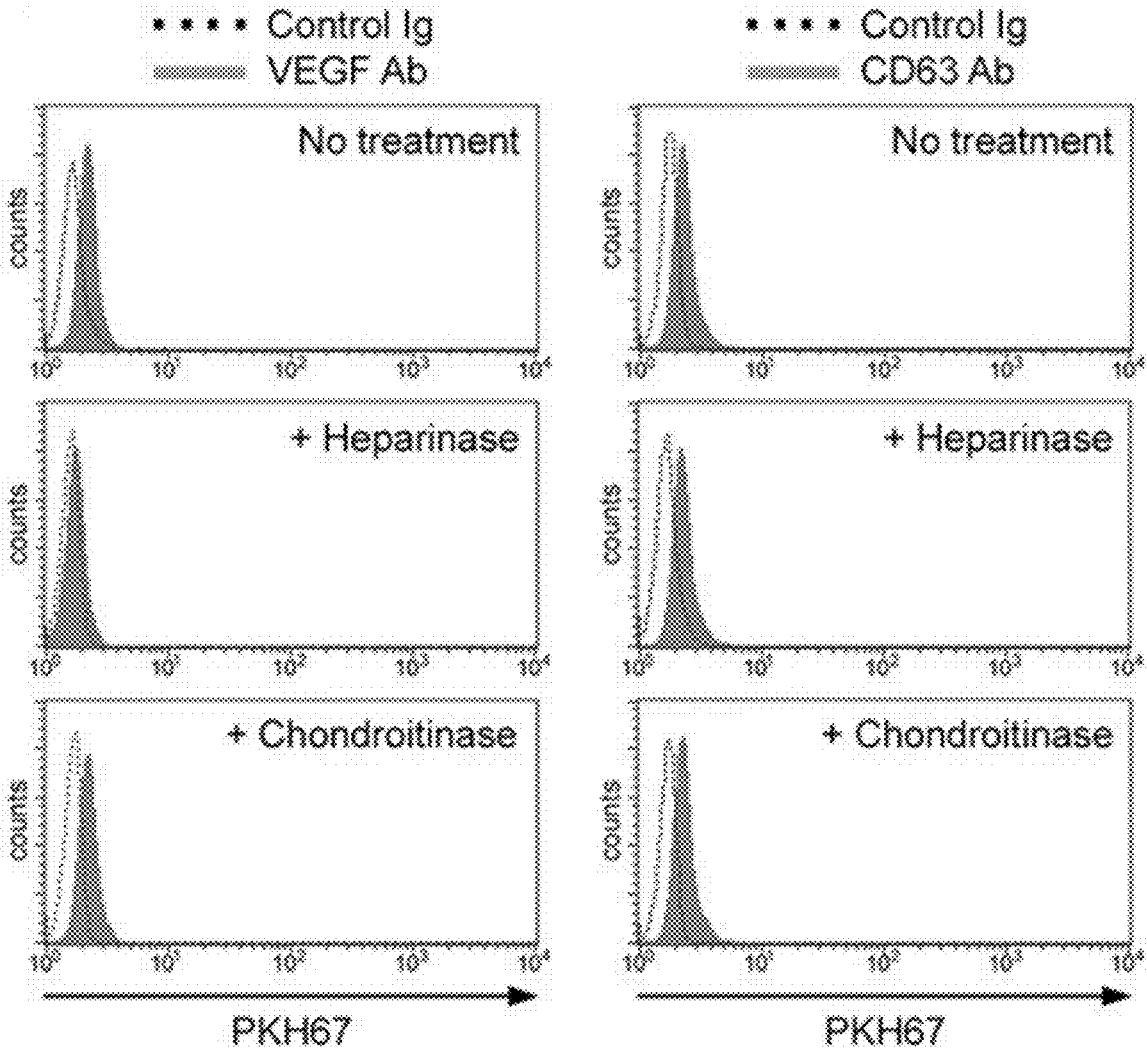
Figures 6G, 6H:
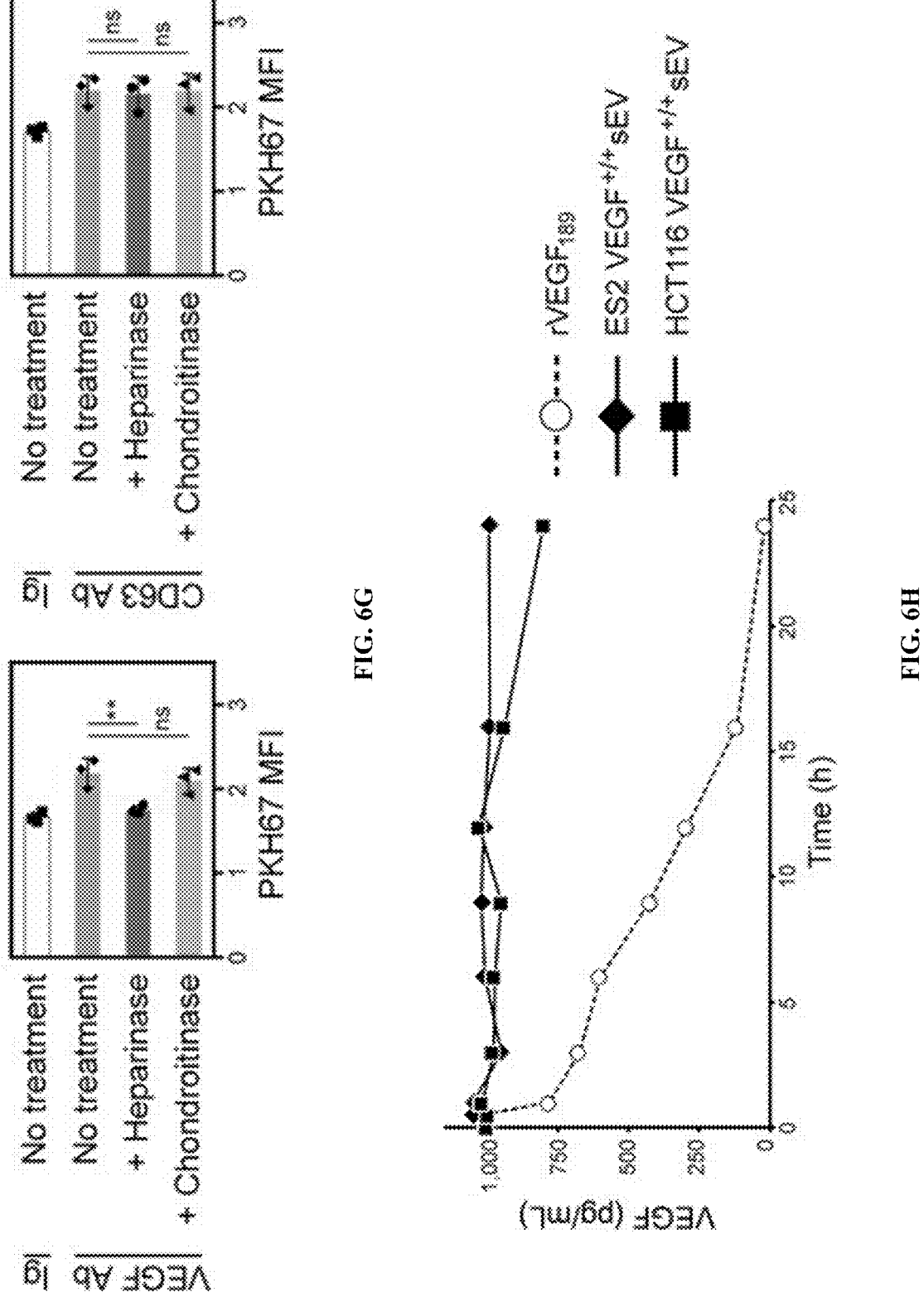

To confirm that $VEGF_{189}$ preferentially localizes to sEVs, $VEGF_{189}$ and two other major isoforms of VEGF ($VEGF_{121}$ and $VEGF_{165}$) were individually reconstituted into $VEGF^{-/-}$ cancer cells, and then the VEGF content in sEVs secreted by these cells assayed. sEVs of cells that expressed VEGF 189 had the highest VEGF content (FIG. 6A). Analysis of VEGF levels in whole and sEV-depleted conditioned media of $VEGF_{189}$-transfected $VEGF^{-/-}$ cells revealed that nearly 90% of the $VEGF_{189}$ was sEV-associated (FIG. 6B). By contrast; analysis of whole and sEV-depleted conditioned media of $VEGF_{121}$-transfected $VEGF^{-/-}$ cells indicated that almost all of the $VEGF_{121}$ was not SEV-associated (FIG. 6C). To test whether $VEGF_{189}$ binds to SEVs following secretion as opposed to being sorted into sEVs, conditioned media of non-transfected $VEGF^{-/-}$ cells (that contains secreted EVs but no VEGF) was incubated with recombinant $VEGF_{189}$ (i.e. 'free $VEGF_{189}$') that was added at an amount equivalent to the total amount of VEGF secreted by $VEGF_{189}$-transfected $VEGF^{-/-}$ cells. Thereafter, sEVs were isolated from the media. The amount of VEGF 189 detected in these sEVs was approximately 25% of the amount of $VEGF_{189}$ in sEVs secreted by $VEGF_{189}$-transfected $VEGF^{-/-}$ cells (FIG. 6D). These findings suggest that; while $VEGF_{189}$ can bind to sEVs post-secretion, the presence of this ligand in sEVs predominantly occurs through selective sorting into sEVs.

Figure 17:
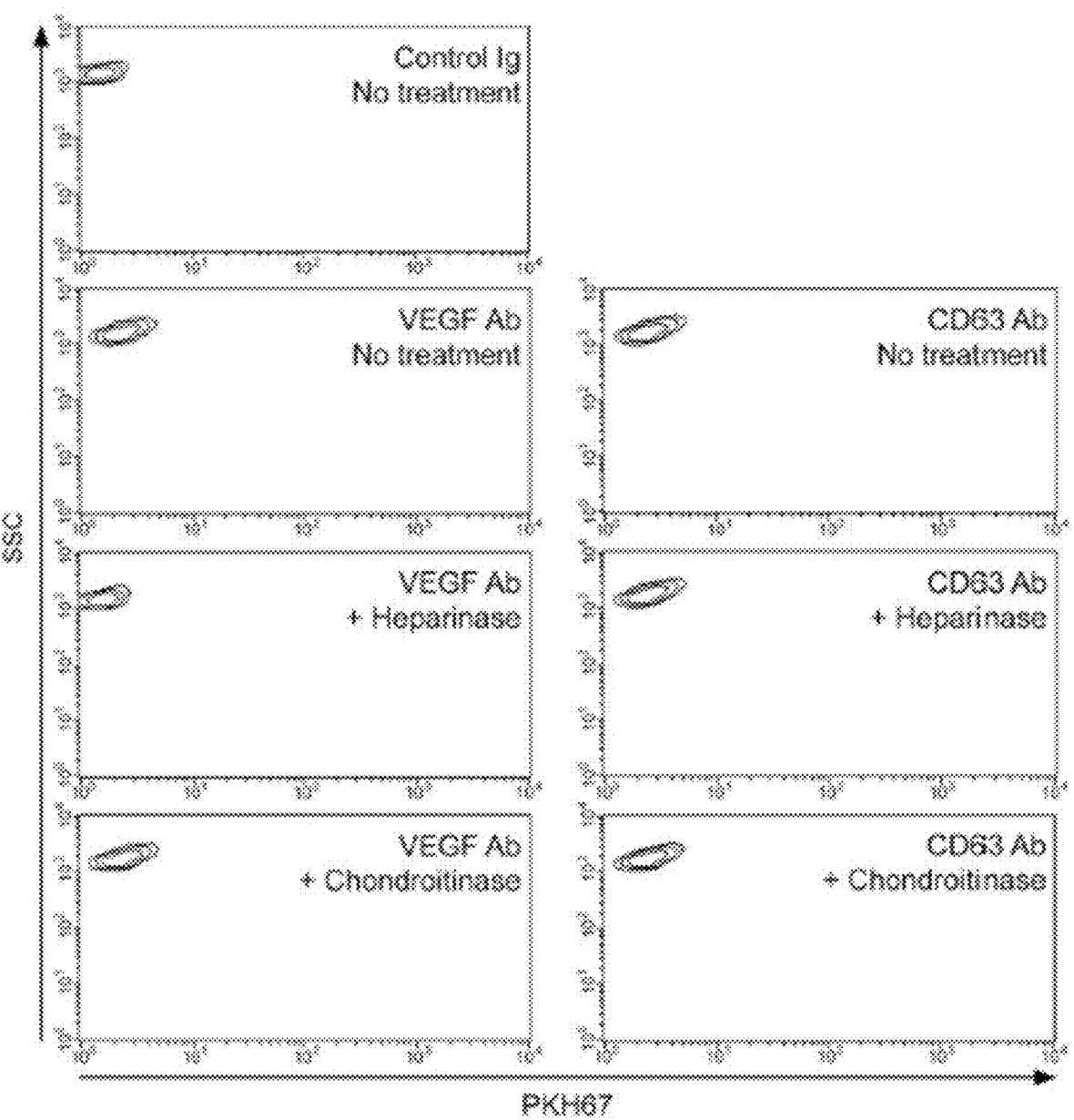
FIG. 17. Effect of enzymatic digestion on association of VEGF with the surface of sEVs. PKH67-labeled sEVs of parental ES2 cells were pretreated with heparinase, chondroitinase or no enzyme, and then incubated with VEGF Ab coupled to microbeads. VEGF on the surface of sEVs was detected by flow cytometric analysis of PKH67 fluorescence in the gated population of Ab-coupled microbeads. Gating strategy is shown in FIG. 13A. As a negative control for enzymatic digestion, the same approach was used to detect the transmembrane protein CD63. Shown are representative contour plots of PKH67 fluorescence.
Figure 18A:
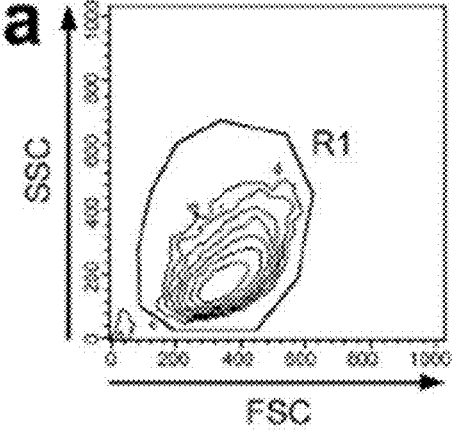
FIGS. 18A-18D. Control assays to detect bevacizumab binding.
Figure 18B:
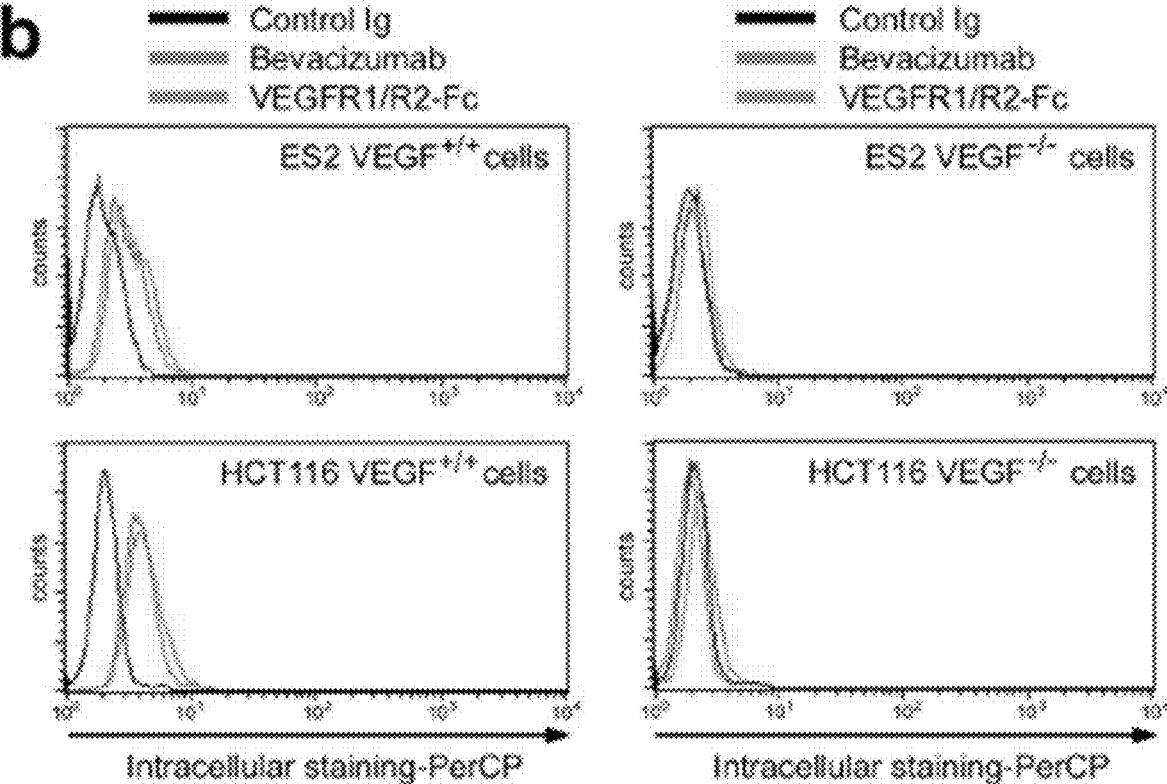
Figures 18C, 18D:
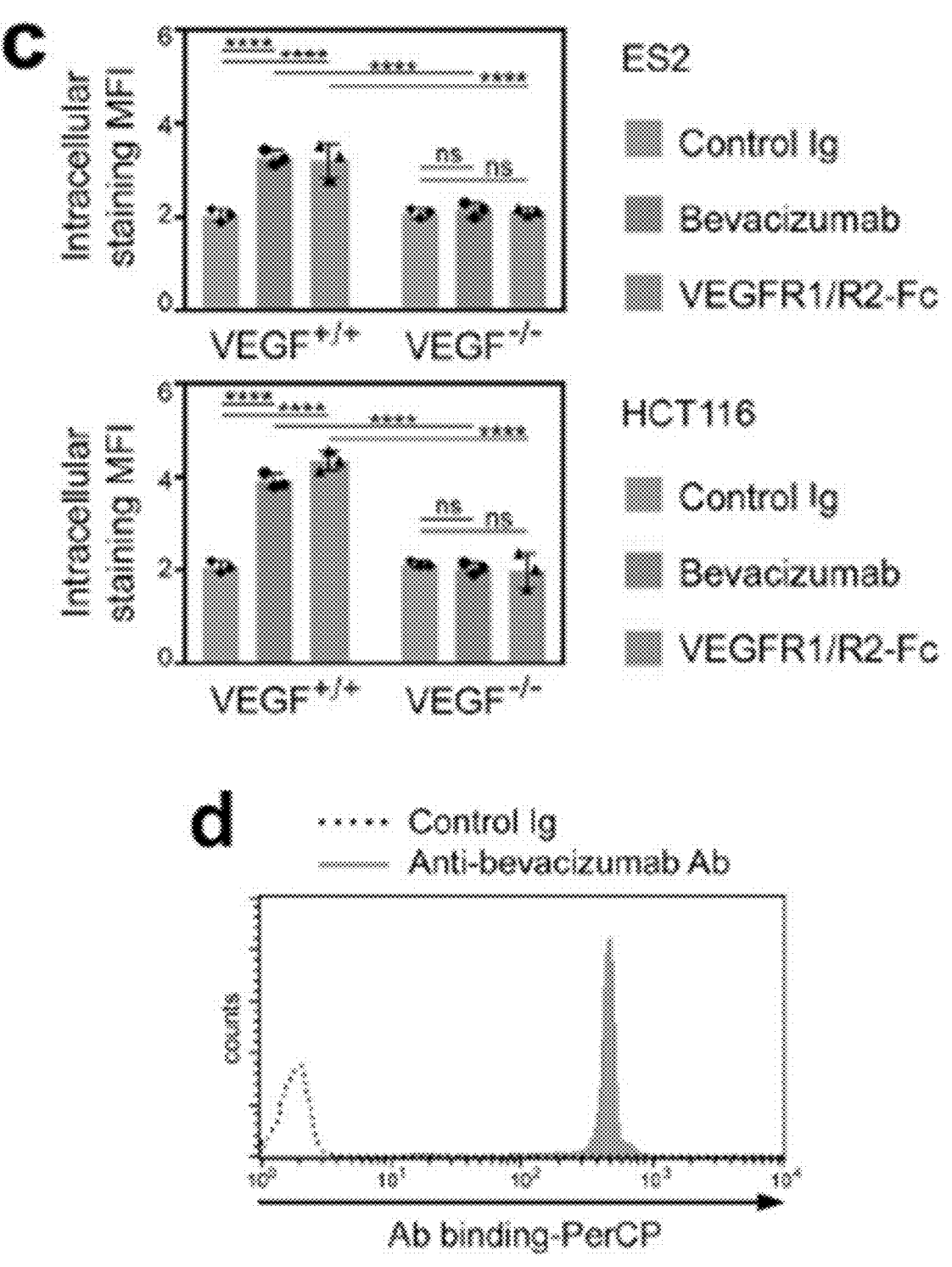

$VEGF_{121}$ lacks a heparin-binding domain whereas $VEGF_{189}$ has substantially higher affinity for heparin than $VEGF_{165}$ (Ferrara et al., 2003). Because sEVs contain membrane-associated heparan sulfate proteoglycans (Christianson et al., 2013), the possibility that heparan sulfate mediates localization of $VEGF_{189}$ in sEVs was investigated. Human $VEGF_{189}$ was overexpressed in CHO-K1 cells and in pgsD-677 cells, a CHO cell mutant that is deficient in heparan sulfate biosynthesis (Lidholt et al., 1992), and then sEVs secreted by these cells were evaluated. Whereas total levels of exogenous $VEGF_{189}$ did not differ between CHO-K1 and pgsD-677 cells, sEVs of pgsD-677 cells contained substantially less $VEGF_{189}$ than sEVs of CHO-K1 cells (P<0.01) (FIG. 6E). To test whether heparan sulfate facilitates the interaction of VEGF 189 with the surface of sEVs, the presence of VEGF following incubation of cancer cell-derived sEVs with heparinase, an enzyme that cleaves heparan sulfate chains, was evaluated. VEGF was removed from sEVs by treatment with heparinase but not with chondroitinase that degrades chondroitin sulfate chains (FIGS. 6F,6G,17). These findings indicate that $VEGF_{189}$ interacts with the surface of sEVs, at least in part, via heparin-binding. Although VEGF has been detected in sEVs (Skog et al., 2008; Treps et al., 2017; Zhao et al., 2018), the possibility that association with sEVs changes properties of the ligand has not been investigated. Following incubation in human plasma at 37° C., levels of recombinant $VEGF_{189}$ rapidly declined and were undetectable at 24 h (FIG. 6H). By contrast, sEV-VEGF was substantially more stable and its levels remained almost unchanged at 24 h following incubation in plasma (FIG. 6H). These findings indicate that association of VEGF 189 with the surface of sEVs profoundly increases the half-life of the ligand.

Example 8—sEV-EGF is not Neutralized by Bevaeizumab In Vitro

Figure 7C:
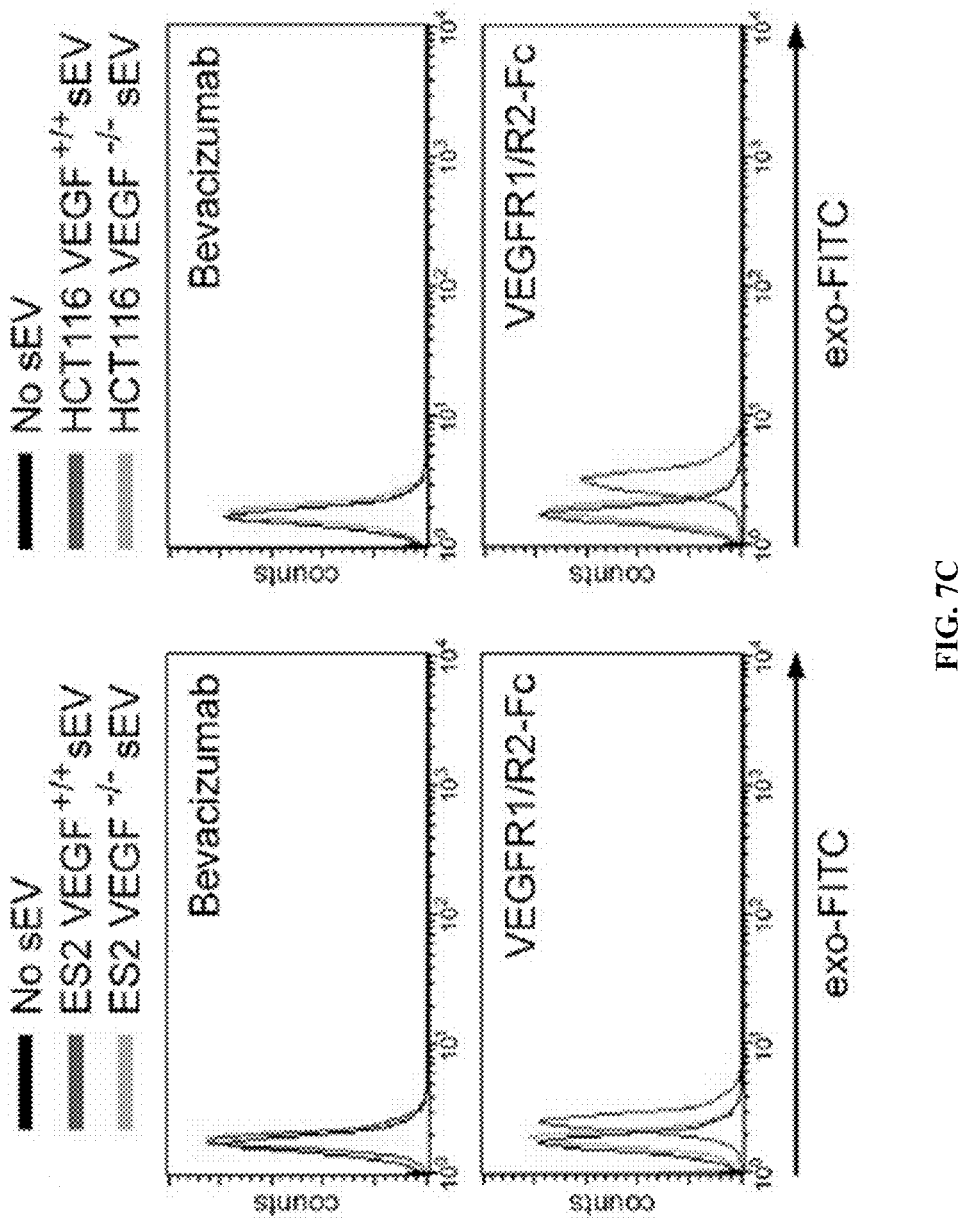
Figure 7D:
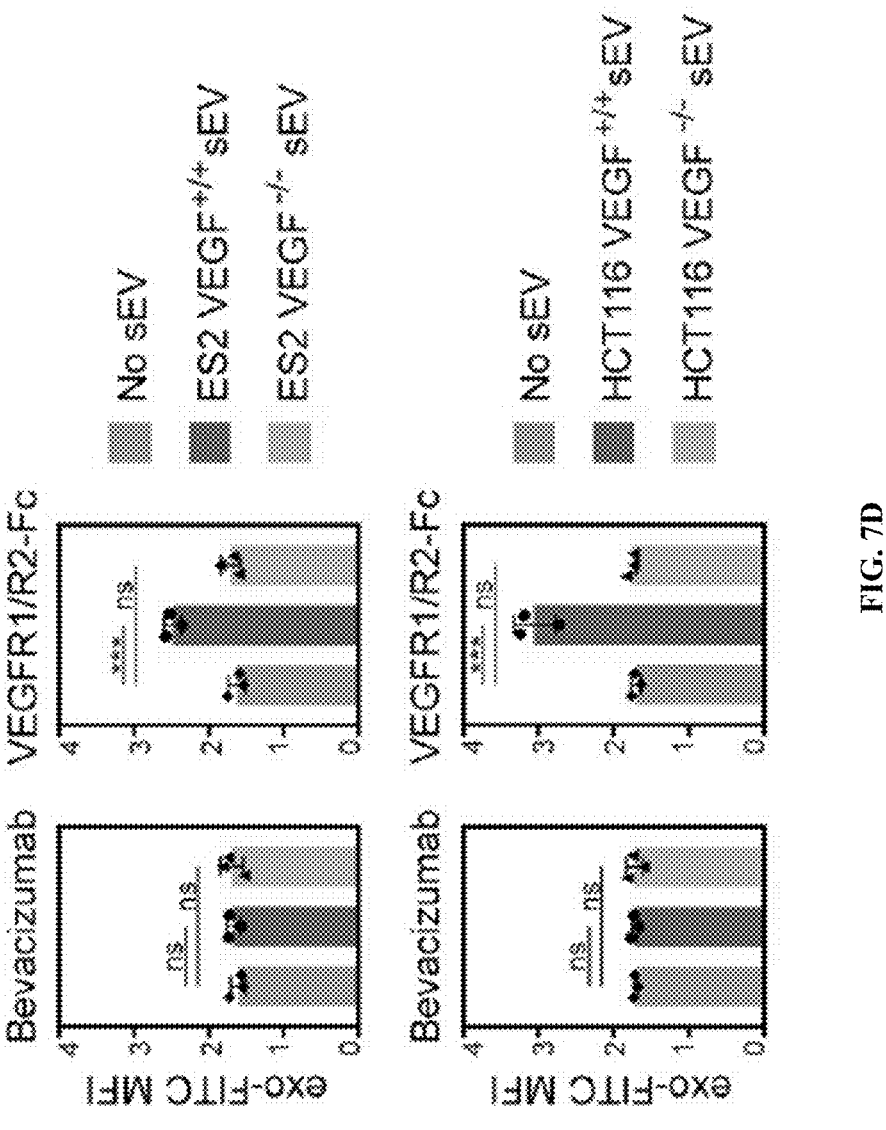
Figure 19A:
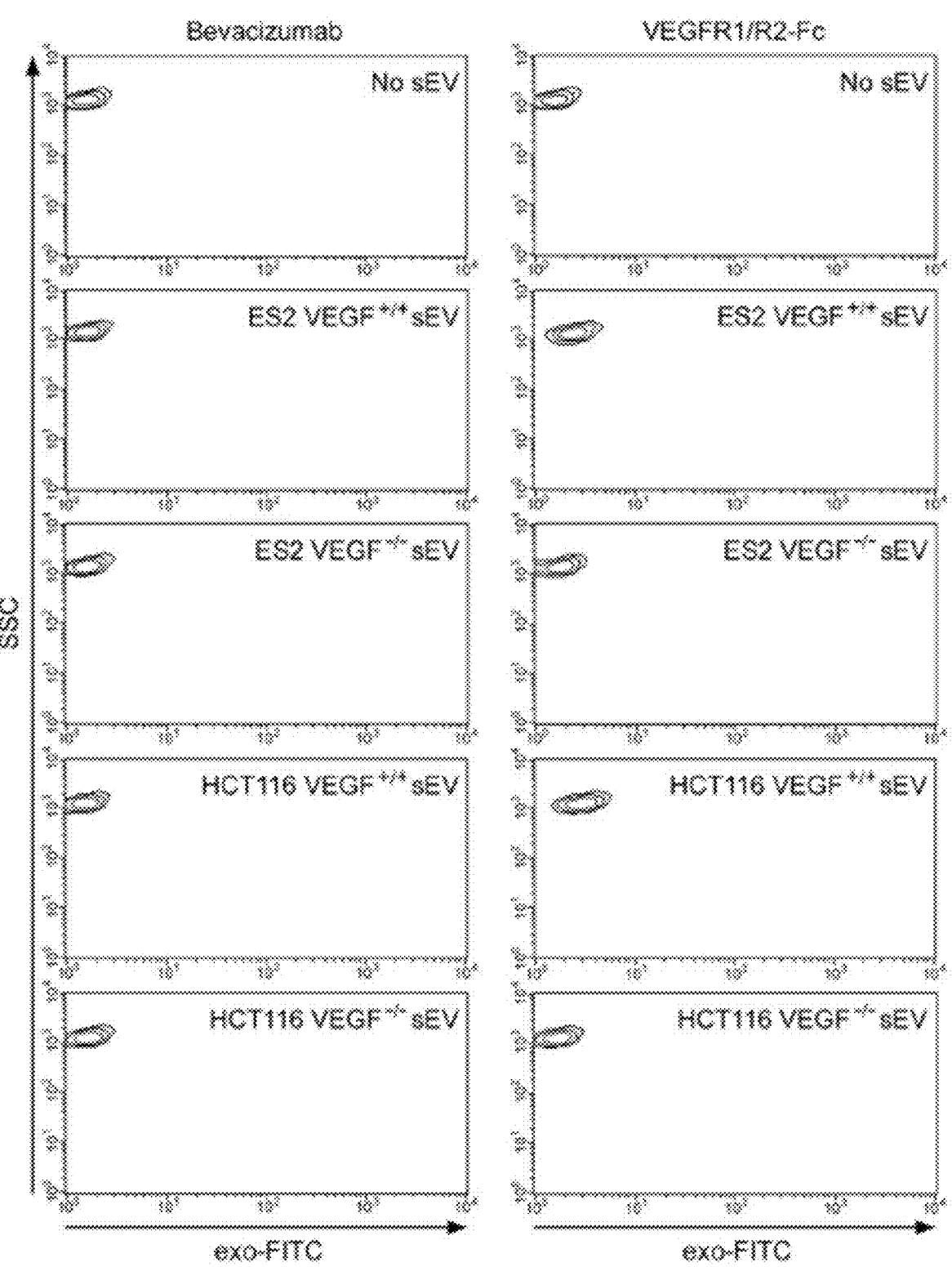
FIGS. 19A-19C. Analysis of ability of bevacizumab to neutralize sEV-VEGF in vitro.
Figure 19B:
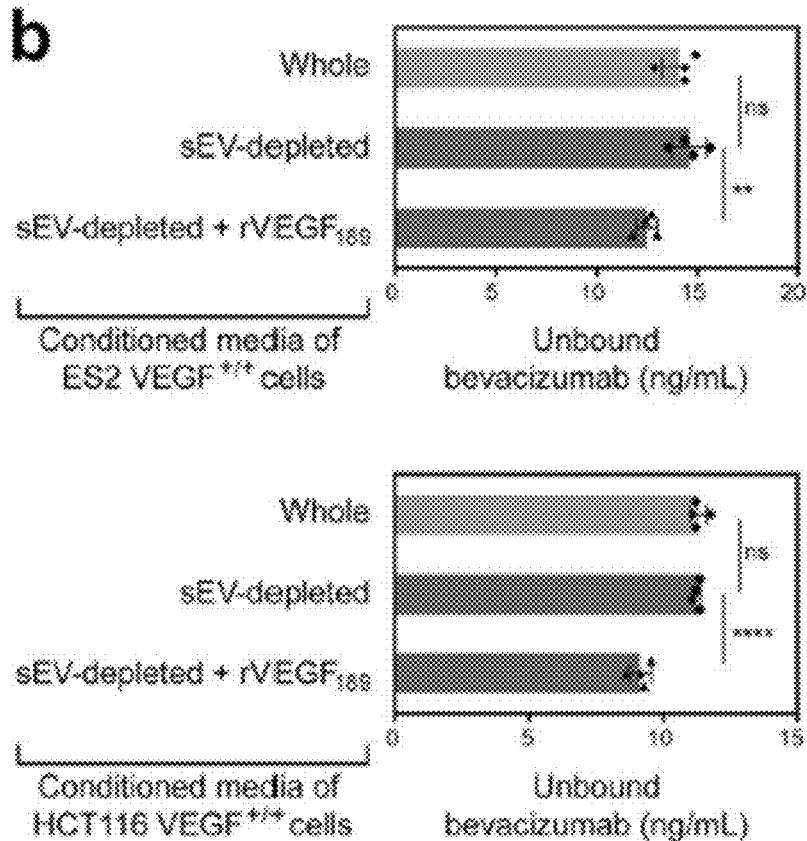

Bevacizumab is a humanized monoclonal Ab that recognizes all isoforms of human VEGF, and is the most studied anti-angiogenic agent (Ferrara et al., 2004). Whereas binding of bevacizutnab to soluble isoforms of VEGF has been characterized (Muller et al., 1998), the ability of bevacizumab to neutralize VEGF when associated with other proteins is poorly understood. Binding of bevacizumab to $VEGF_{189}$ was significantly reduced when VEGF 189 was pre-bound to high molecular weight (RMW) heparin (P<0.0001) (FIGS. 7A,7B). Because $VEGF_{189}$ associates with sEVs via heparin-binding (FIGS. 6F,6G), it was tested whether bevacizumab binds sEV-VEGF It was initially confirmed that recognition of VEGF by bevacizumab can be detected by flow cytometry and that bevacizumab can be coupled to microbeads (FIGS. 18A-18D). Bevacizumab-coupled microbeads were then incubated with sEVs, followed by labeling of sEV membrane with exo-FITC dye. Binding of bevacizumab to sEV-VEGF was evaluated by analyzing exo-FITC fluorescence on coupled microbeads. In control assays, sEVs were incubated with microbeads coupled to VEGFRUR2-Fc, a chimera that consists of the ligand-binding domains of VEGFR1 and VEGFR2 fused to the Fc portion of human $IgG_1$. VEGFR1/R2-Fc bound to $VEGF^{+/+}$ sEVs but not $VEGF^{-/-}$ sEVs (FIGS. 7C,7D,19A). This finding was consistent with the activation of VEGFR2 by $VEGF^{+/+}$ sEVs and not VEGF sEVs (FIG. 4A). In contrast, bevacizumab did not bind to $VEGF^{+/+}$ sEVs (FIGS. 7C,7D,19A).

Figures 7E, 7F, 7G:
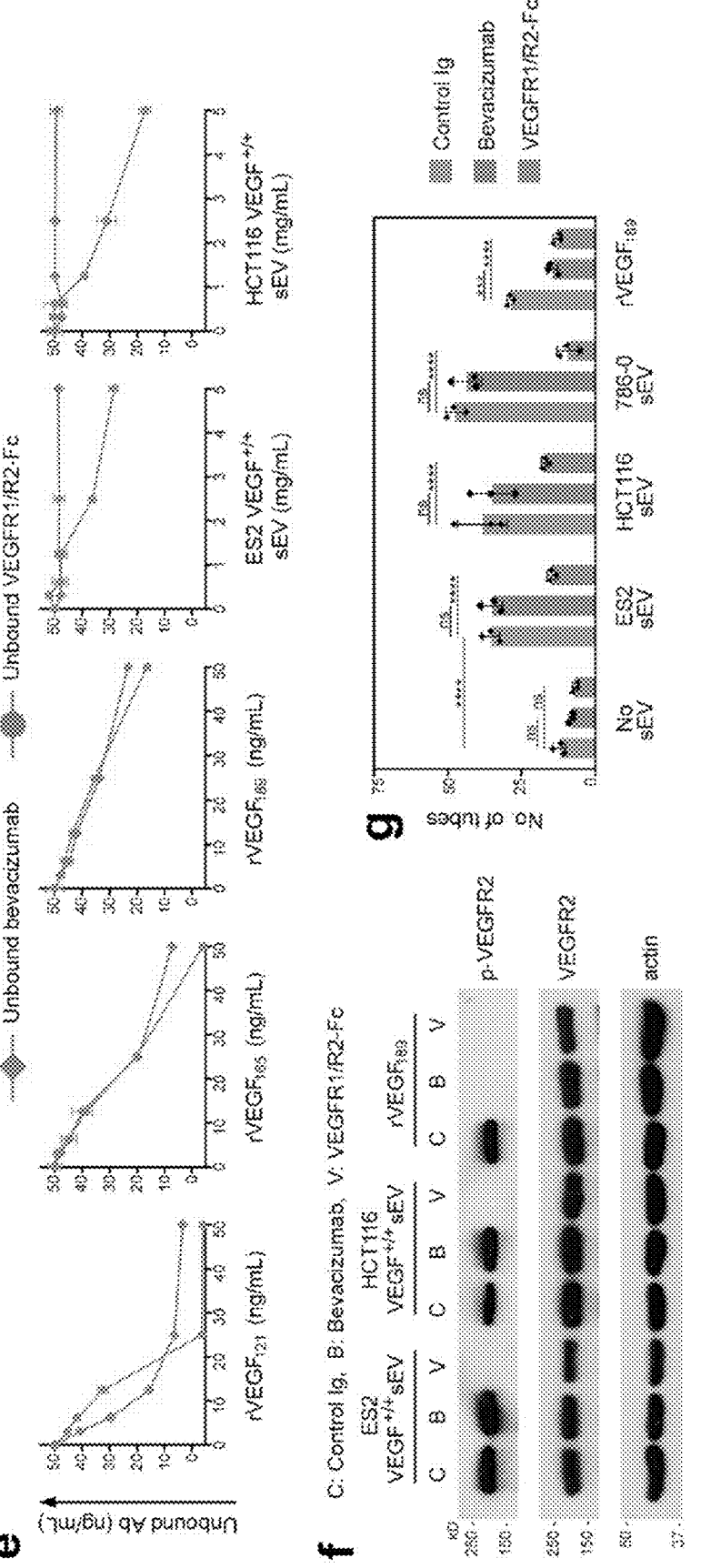
Figure 7H:
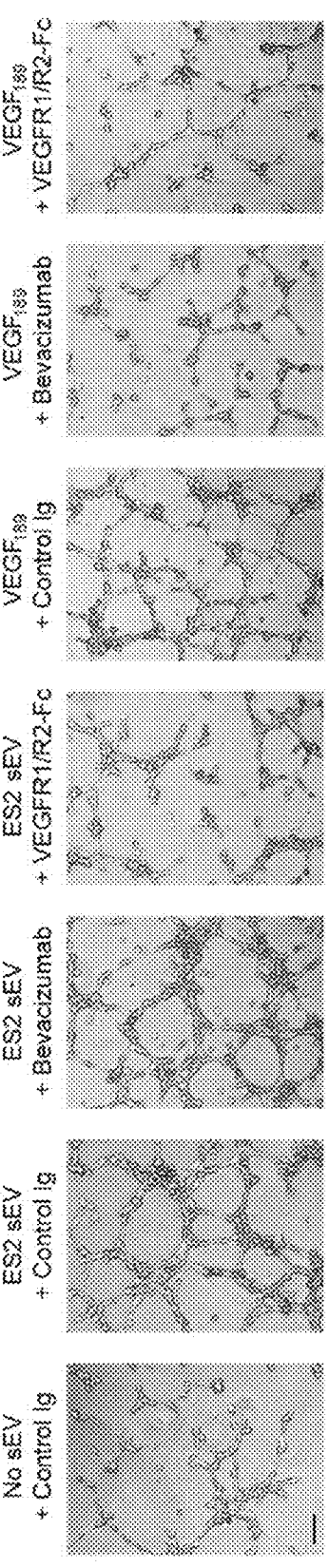
Figure 19C:
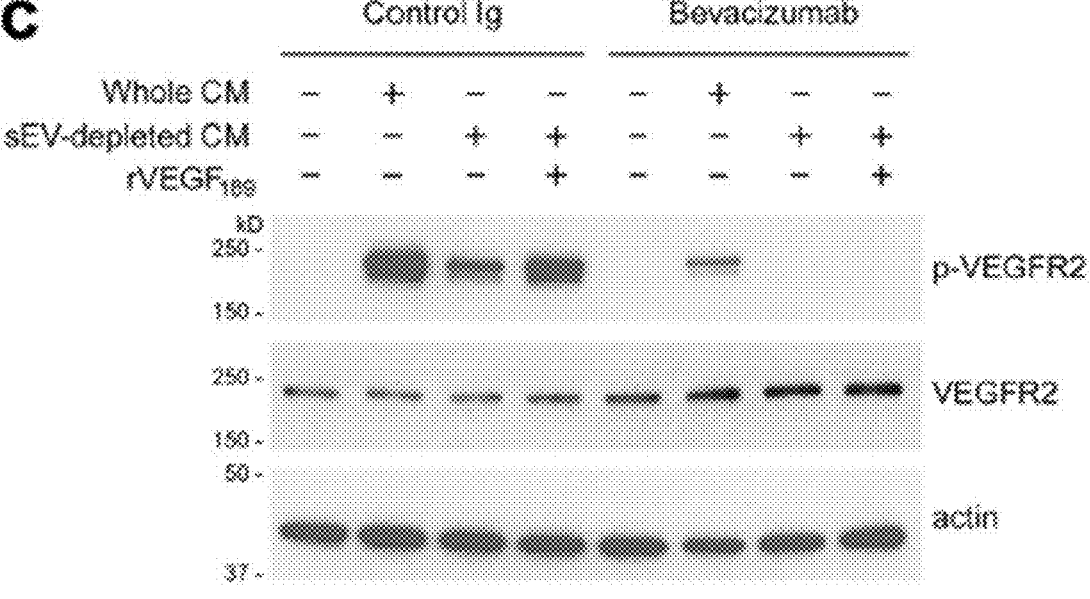

To confirm these findings, bevacizumab was incubated with either recombinant VEGF or $VEGF^{+/+}$ sEVs and thereafter levels of unbound bevacizumab were assayed. Levels of unbound bevacizumab decreased following incubation with increasing amounts of recombinant VEGF but did not decrease following incubation with $VEGF^{+/+}$ sEVs containing equivalent amounts of VEGF (FIG. 7E). Consistent with these findings, bevacizutnab blocked VEGFR2 phosphorylation and tube formation in endothelial cells that were stimulated with recombinant VEGF but not in cells stimulated with $VEGF^{+/+}$ sEVs (FIGS. 7F-7H). To test the neutralizing ability of bevacizumab under conditions where soluble VEGF and sEVs carrying VEGF are co-secreted, cancer cell-conditioned media was depleted of sEVs or left whole, and then incubated with bevacizumab. Following incubation, levels of unbound bevacizumab in whole media were almost identical to those in sEV-depleted media (FIG. 1913), indicating that bevacizumab only neutralized non-sEV-VEGF. This was confirmed by the decrease in unbound bevacizumab levels following incubation in sEV-depleted media to which recombinant $VEGF_{189}$ had been added (FIG. 1911). Consistent with the ability of bevacizumab d non-sEV-VEGF and not sEV-VEGF, bevacizumab completely blocked VEGFR2 phosphorylation in endothelial cells that were stimulated with sEV-depleted media but only partially inhibited VEGFR2 phosphorylation in endothelial cells stimulated with whole media (FIG. 19C).

Example 9—sEV-VEGF is not Neutralized by Bevacizumab In Vivo

Figures 20A, 20B:
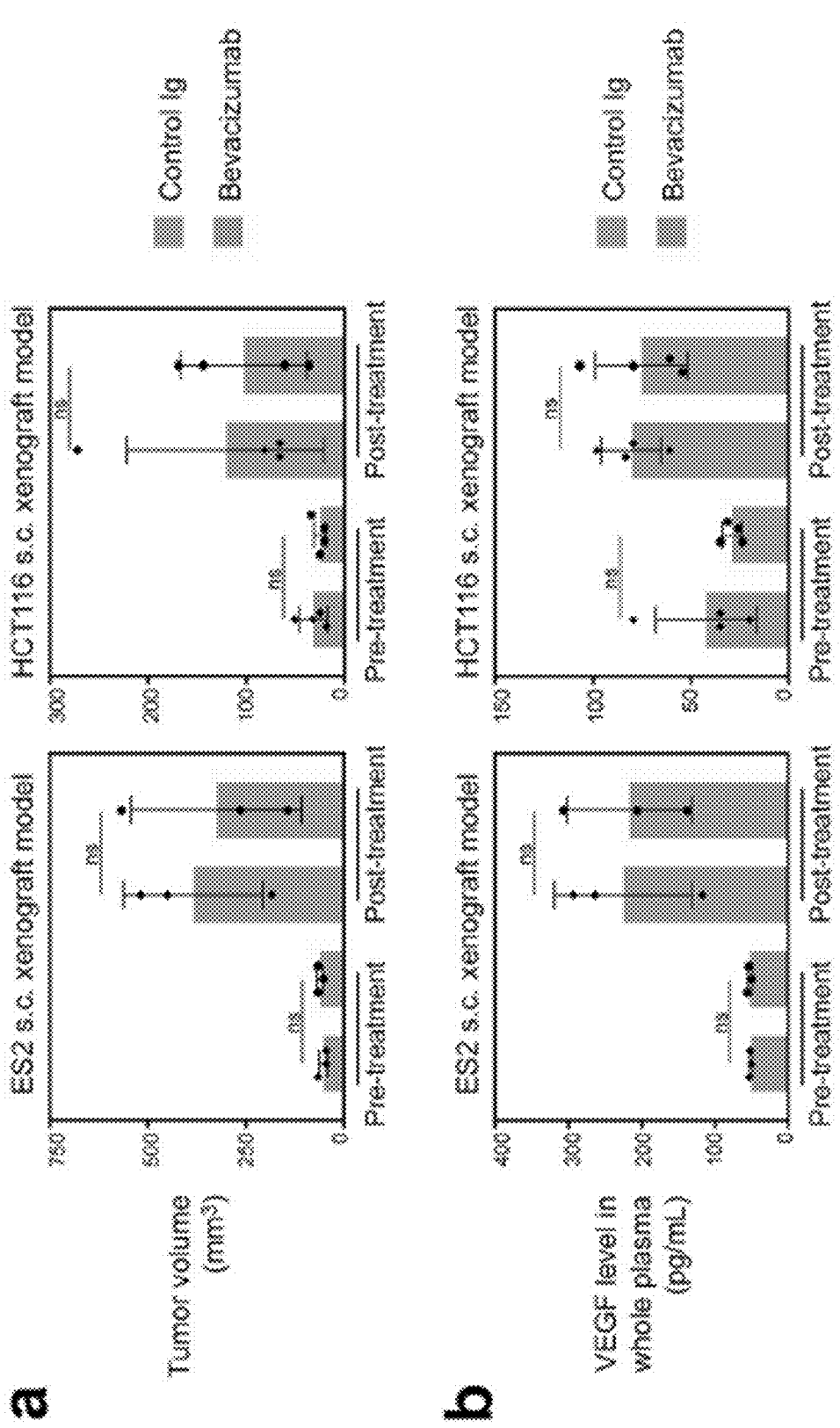
FIGS. 20A-20D. Analysis of ability of bevacizumab to neutralize naturally secreted sEV-VEGF in vivo. Nude mice were inoculated subcutaneously (s.c.) with parental ES2 or HCT116 cells. At 7 days thereafter when tumors were palpable, peripheral blood samples were collected (i.e. pre-treatment). Mice were then randomized into groups (n=3 per group for ES2; n=4 per group for HCT116) and administered either normal human IgG (control) or bevacizumab i.p. 3 times for one week. Thereafter, peripheral blood samples were again collected (i.e. post-treatment). Pre- and post-treatment plasma samples were depleted of sEVs or left non-depleted (i.e. whole) and assayed for human VEGF by ELISA.
Figures 20C, 20D:
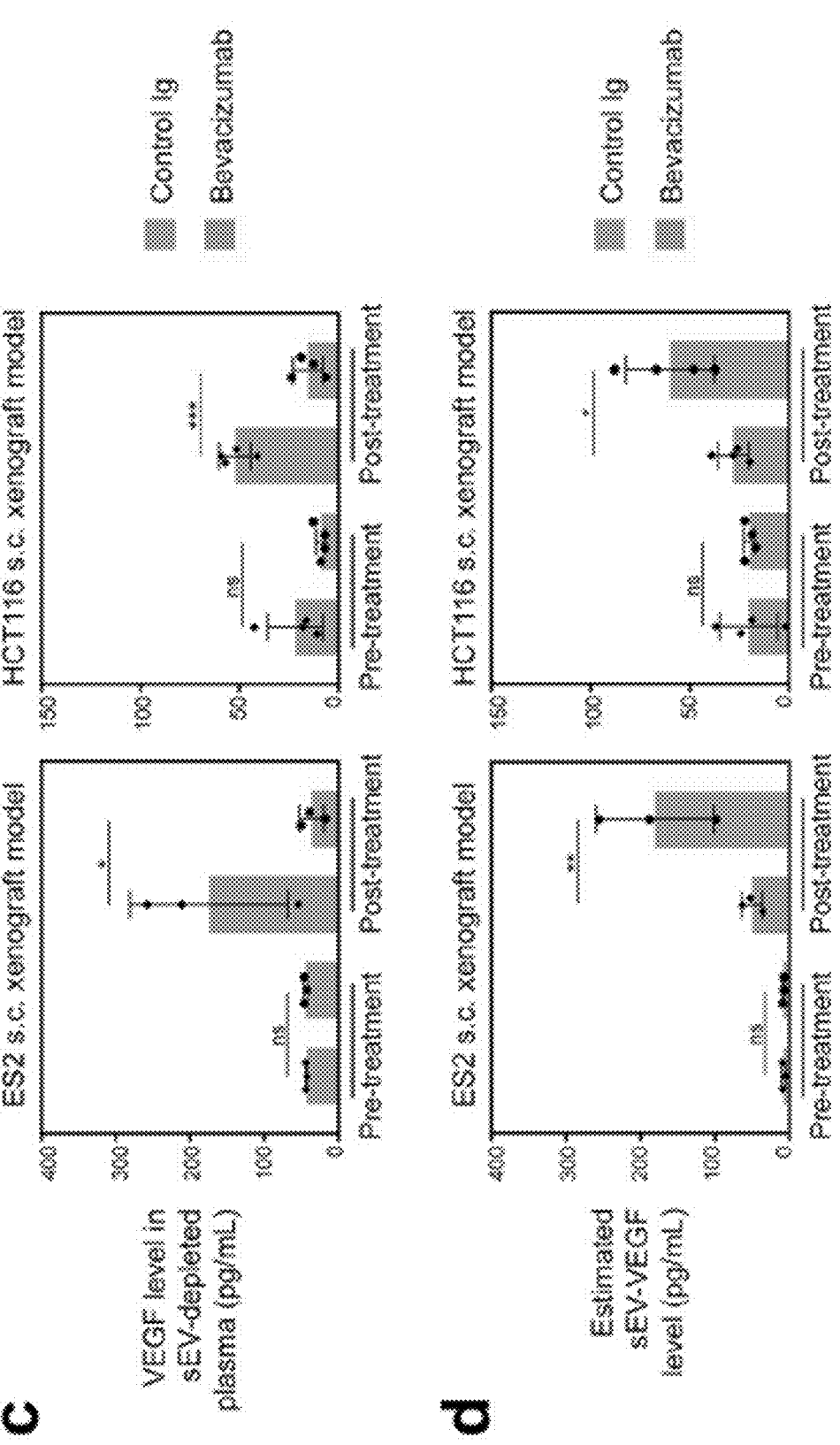

To confirm these findings in vivo, nude mice were injected i.p. with ES2 $VEGF^{-/-}$ cells and thereafter randomized mice into groups that were then administered sEVs of ES2 VEGF$^{+/+}$ cells with bevacizumab or control Ig, or administered recombinant VEGF$_{189}$ with bevacizumab or control Ig. As compared to treatment with control Ig, bevacizumab inhibited tumor growth (P<0.001), angiogenesis (P<0.0001) and ascites (P<0.001) in mice that had been administered recombinant VEGF$_{189}$, but not in mice that had been administered VEGF$^{+/+}$ sEVs (FIGS. 8A-8E). Next, the effect of bevacizumab on endogenous levels of tumor-derived sEV-VEGF and non-sEV-VEGF was evaluated by treating mice bearing s.c. tumors derived from parental ES2 and HCT116 cells with bevacizumab for one week. Bevacizumab did not inhibit tumor growth during this period (FIG. 20A), as observed in other studies that used the same models (Tsujioka et al., 2011; Iwai et al., 2016). Plasma samples collected from mice pre- and post-treatment were depleted of sEVs or left non-depleted and then assayed for human VEGF. sEV-VEGF levels were estimated from differences between VEGF levels in whole and sEV-depleted plasma (FIGS. 20B-20D). Following bevacizumab treatment, non-sEV-VEGF levels decreased (ES2, P<0.05; HCT116, P<0.001), whereas sEV-VEGF levels increased (E52, P<0,01; HCT116, P<0.05) (FIGS. 20C,20D).

Example 10—Clinical Significance of High Baseline Levels of sEV-VEGF

Figure 21A:
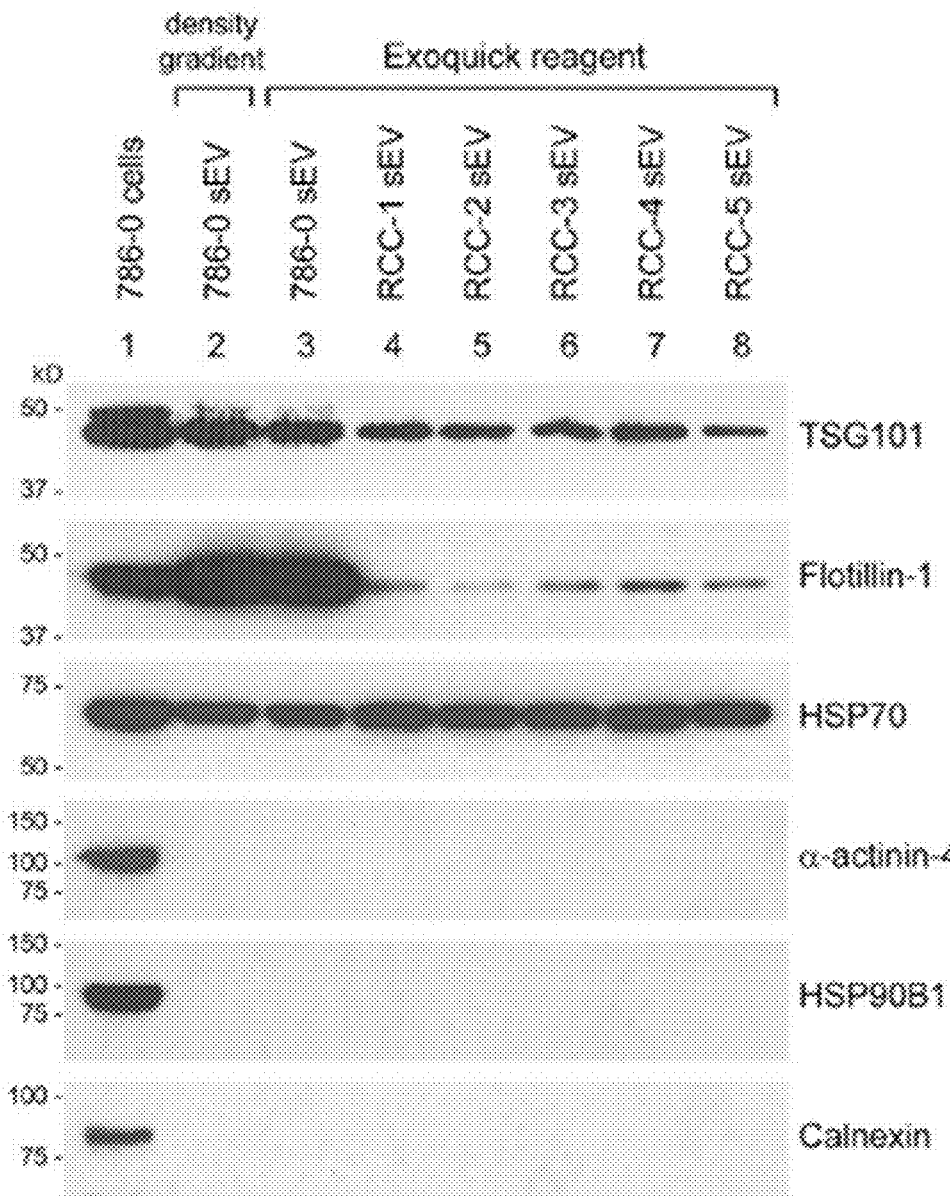
FIGS. 21A-21B. Analysis of markers and particle size distribution of plasma sEVs of bevacizumab-treated patients. sEVs were isolated from plasma samples from a Phase II trial of patients with newly diagnosed metastatic renal cell carcinoma who had been treated presurgically with bevacizumab (study NCT00113217) (Jonasch et al., 2009). Because volumes of these plasma samples were too small for sEVs to be isolated by density gradient ultra-centrifugation, sEVs were isolated from these samples by using ExoQuick reagent.
Figure 21B:
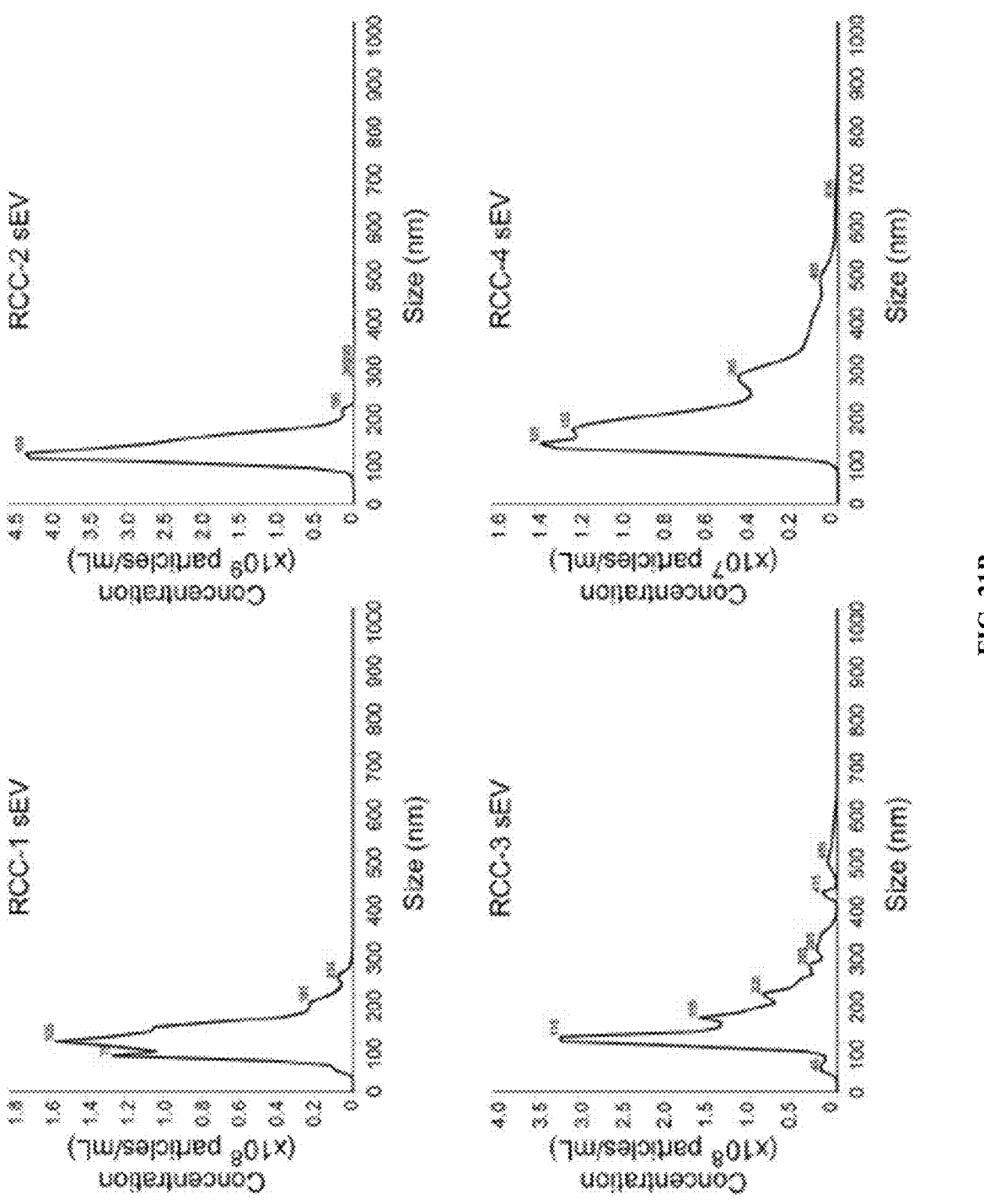

The findings that bevacizumab does not neutralize sEV-VEGF raise the possibility that cancer patients who have elevated levels of sEV-VEGF might not benefit from bevacizumab. Bevacizumab has been approved for a variety of solid tumors in combination with chemotherapy and/or in a recurrent setting (Cao et al., 2011). Because combination therapy and prior treatment can complicate interpretations, the relationship between baseline levels of sEV-VEGF and outcomes were investigated in a cohort of newly diagnosed cancer patients who received bevacizumab monotherapy. Specifically, plasma samples were analyzed from a Phase II trial of patients with newly diagnosed Stage IV metastatic renal cell carcinoma who were treated presurgically with single-agent bevacizumab and thereafter restaged (study NCT00113217) (Jonasch et al., 2009). Because volumes of these plasma samples were too small for sEVs to be isolated by density gradient ultracentrifugation, sEVs were isolated by using ExoQuick reagent. It was confirmed that these sEVs expressed sEV markers, lacked markers of larger EVs and non-EV components, and had a size distribution similar to that of sEVs isolated by density gradient ultracentrifugation (FIGS. 21A,21B).

Baseline (i.e. pre-treatment) levels of total VEGF and sEV-VEGF were assayed in plasma samples blinded to clinical data and thereafter evaluated for relationships with outcomes. No significant difference in baseline total VEGF levels was found between patients who showed disease progression following bevacizumab treatment and patients who had stable or regressing disease (FIG. 8F). In contrast, baseline sEV-VEGF levels were approximately 5-fold higher in patients with progressing disease than in patients with stable or regressing disease (P=0.010) (FIG. 8G). These findings suggest that baseline levels of sEV-VEGF are more informative for bevacizumab treatment benefit than levels of total VEGF.

Example 11—Assay System for Measuring Levels of Bevacizumab-Insensitive VEGF in Biological Fluids The use of sEV-associated molecules as cancer biomarkers has been hampered by the need to isolate sEVs at high purity, which requires large volumes of biological fluids (i.e. more than 1 mL, which is not feasible for plasma), is very labor-intensive and time-consuming (approximately 2 days to process a given sample), is very low-throughput (can only process less than 6 samples at one time), requires many expensive reagents, and requires specialized equipment that cannot be used in a clinical setting. As such, provided herein an assay system that extrapolates levels of bevacizumab-insensitive sEV-VEGF in small volumes of clinical samples, is high-throughput, and can be readily translated into the clinic. This assay system requires only 0.2 mL of biological fluid, takes less than 5 hours to complete, can readily assay 96 samples on one plate, can be adapted for automation, requires only a small number of reagents, and requires only a microplate reader, which is standard clinical laboratory equipment.

Figure 22:
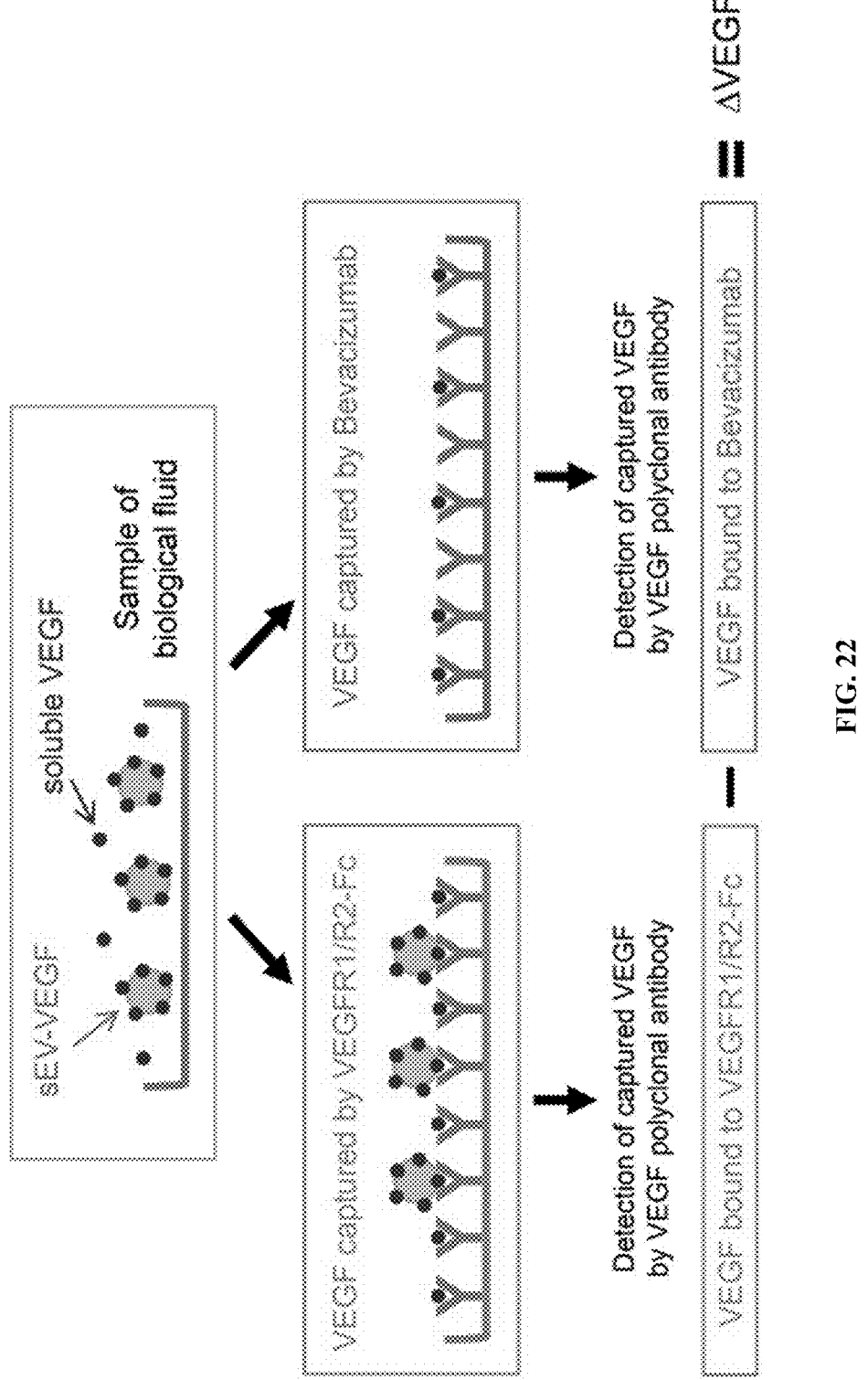
FIG. 22. Assay for determining the amount of VEGF that cannot be neutralized by bevacizumab.

This assay system extrapolates the amount of bevacizumab-insensitive sEV-VEGF in biological fluids from two parallel immunoassays (FIG. 22). In one immunoassay, the total amount of biologically active VEGF, i.e., VEGF that is capable of binding to its receptors (VEGFR1 and VEGFR2), is measured. In the other immunoassay, the amount of VEGF that can be bound by bevacizumab is measured. Then the amount of bevacizumab-bound VEGF is subtracted from the amount of biologically active VEGF to determine an amount of VEGF that cannot be neutralized by bevacizumab and that includes sEV-VEGF, i.e., the amount of ΔVEGF.

In particular, one 96-well High Bind microplate (Corning) was coated with VEGFR1/R2-Fc µg/well) (i.e. chimera that consists of ligand-binding domains of VEGFR1 and VEGFR2 fused to Fc portion of human IgG$_1$) (Aflibercept, Regeneron Pharmaceuticals). A second microplate was coated with bevacizumab (1 µg/well) (Genentech). Following incubation at room temperature for 16 h, both microplates were washed, incubated with 10% goat serum for 1 h and washed again. Thereafter, biological fluids (ascites, serum, plasma) and VEGF controls (100 µL) were added to wells. Standard controls of recombinant VEGF$_{165}$ (BioLegend) were prepared at concentrations ranging from 15.6 µg/mL to 1000 µg/mL. VEGF that was captured by VEGFR1/R2-Fc or by bevacizumab was detected by incubation with HRP-conjugated polyclonal VEGF antibody (R&D Systems) for 2 h at room temperature, followed by washing and addition of HRP substrate solution. Absorbance was read at 450 nm on a microplate reader. Amounts of VEGFR1/R2-Fc-bound VEGF and bevacizumab-bound VEGF were calculated from the standard curve of respective plates. The AVEC& value was calculated by subtracting the amount of bevacizumab-bound VEGF from the amount of VEGFR1/R2-Fc-bound VEGF.

Figures 23A, 23B:
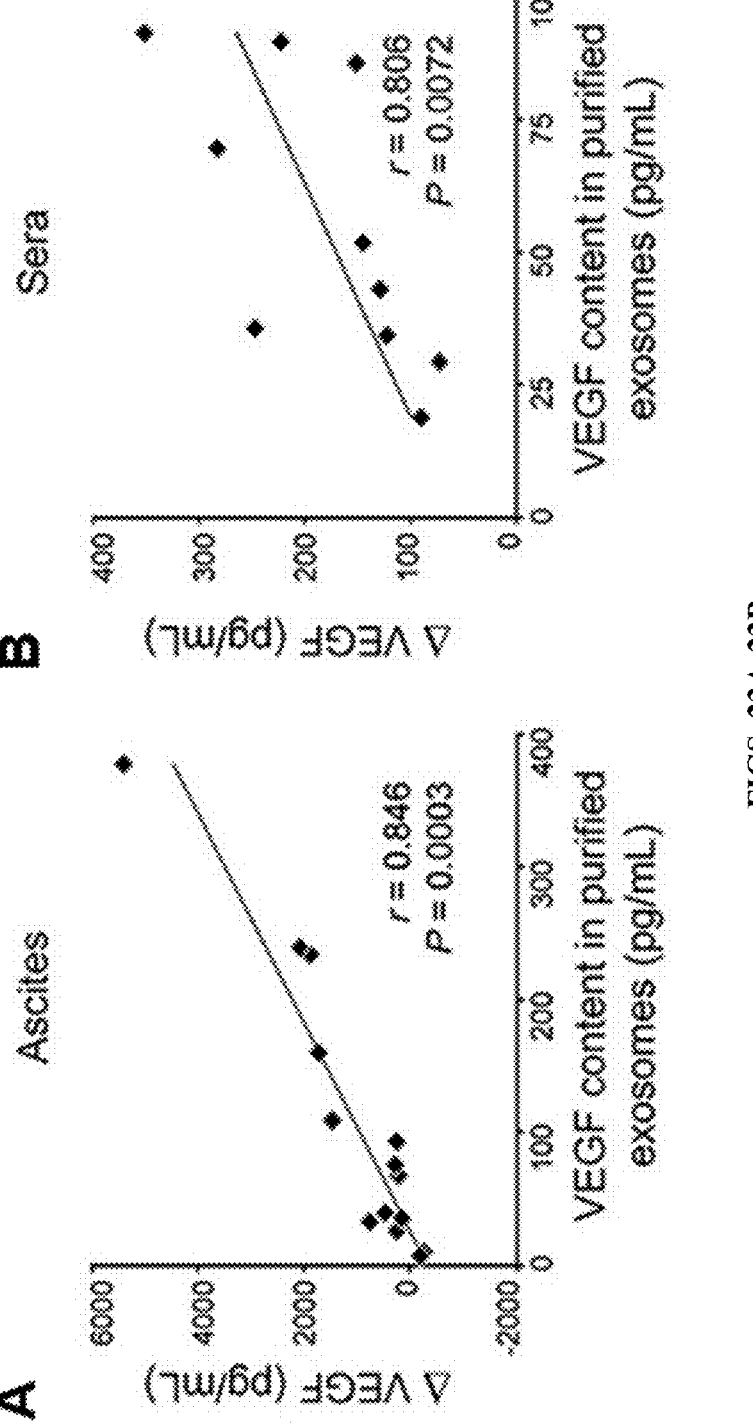
FIGS. 23A-23B. Correlation between ΔVEGF values in samples of biological fluids and the VEGF content in sEVs purified from the same samples. ΔVEGF values were determined in samples of ascites (n=14 cases) (FIG. 23A) and serum (n=10 cases) (FIG. 23B) of ovarian cancer patients by using the immunoassays shown in FIG. 22. Thereafter, ΔVEGF values were evaluated for correlations with the VEGF content in sEVs that were purified from the same samples. Correlation coefficients were determined by Spearman test.

To determine whether ΔVEGF can serve as a reliable index of the amount of sEV-VEGF, the following studies were performed. Using the dual-immunoassays, ΔVEGF values in ascites samples of 14 ovarian cancer patients were obtained, and then the ΔVEGF values were evaluated for correlations with the VEGF content in sEVs that were purified from the same ascites samples (FIG. 23A). Similarly, the dual-immunoassays were used to obtain ΔVEGF values in serum samples of 10 ovarian cancer patients, and the ΔVEGF values evaluated for correlations with the VEGF content in sEVs that were purified from the same serum samples (FIG. 23B). It should be noted that ΔVEGF values could not be directly compared with the VEGF content in purified sEVs because sEV loss during purification is not inconsiderable. However, the strong correlations between the ΔVEGF values and VEGF content in purified sEVs indicated that ΔVEGF can serve as an index of sEV-VEGF.

In addition, the relationship between baseline ΔVEGF values in biological fluids and clinical outcomes was evaluated in two small independent cohorts of cancer patients who received bevacizumab treatment. All VEGF assays were performed blinded to clinical data. Thereafter, VEGF levels were evaluated for relationships with outcomes.

Figures 24, 25A, 25B, 25C:
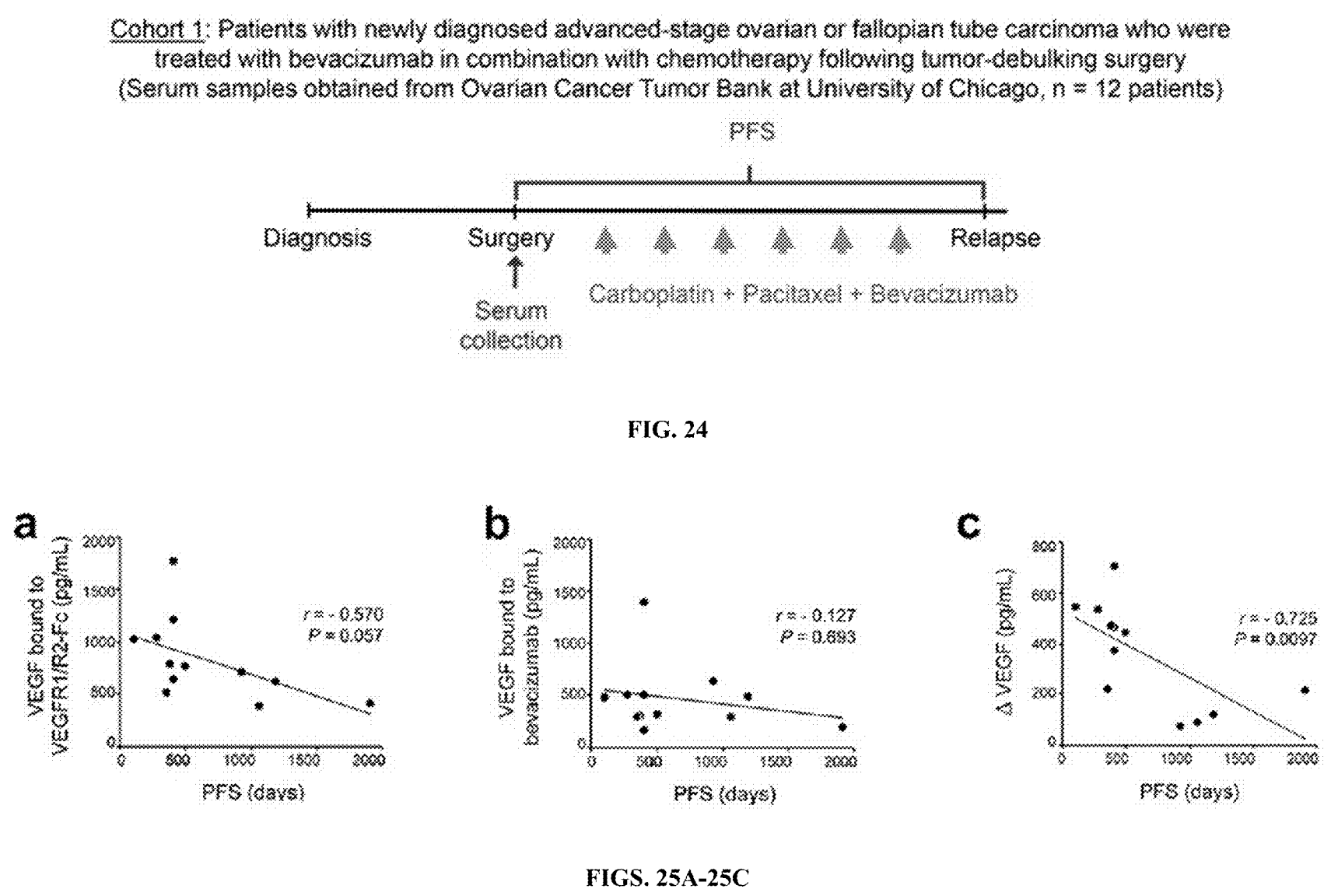

Cohort 1 comprised of patients with newly diagnosed advanced-stage ovarian or fallopian tube carcinoma who were treated with bevacizumab in combination with chemotherapy following tumor-debulking surgery (see FIG. 24; Table 2). In Cohort 1, no significant correlation was found between the baseline serum level of biologically active VEGF and PFS (FIG. 25A), or between the baseline serum level of bevacizumab-sensitive VEGF and ITS (FIG. 25B). In contrast, baseline serum ΔVEGF values showed a significant inverse correlation with PFS (FIG. 25C).

Figure 26:
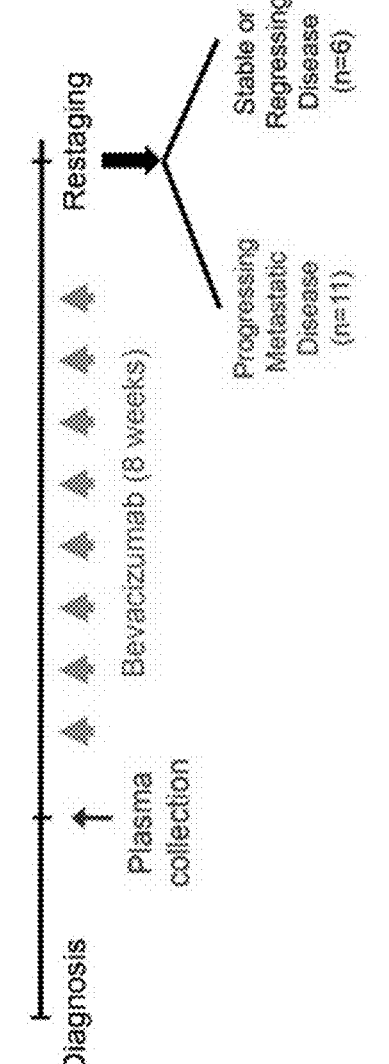
FIG. 26. Cohort 2. Patients newly diagnosed with metastatic renal cell carcinoma who were treated pre-surgically with single-agent bevacizumab and were thereafter restaged.
Figure 27A:
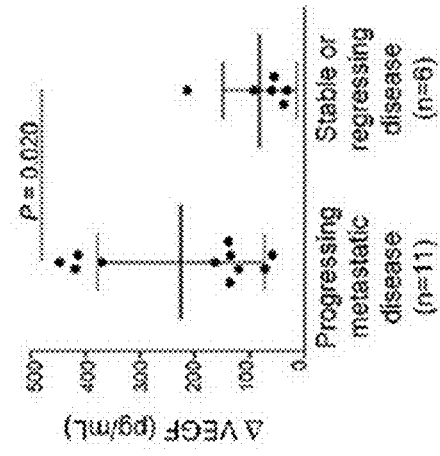
FIG. 27A-27C. Comparison of VEGF levels in patients with progressing disease and in patients with stable or regressing disease in Cohort 2. Levels of VEGF capable of binding to VEGFR1/R2-Fc (FIG. 27A), levels of VEGF capable of binding to bevacizumab (FIG. 27B), and ΔVEGF values (FIG. 27C) were determined in baseline plasma samples of patients in Cohort 2 by using the immunoassays shown in FIG. 22. P values were determined by Mann-Whitney U-test.
Figure 27B:
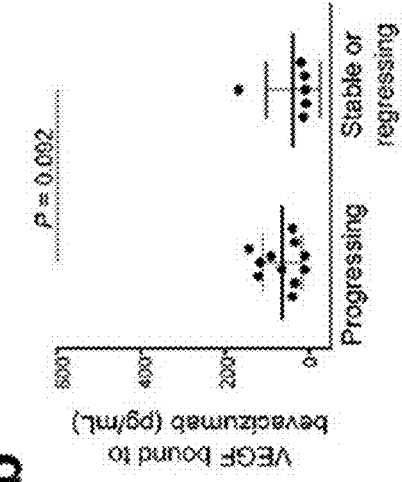
Figure 27C:
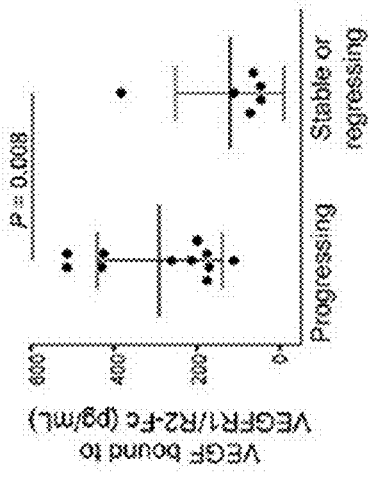

Cohort 2 comprised of patients with newly diagnosed metastatic renal cell carcinoma who were treated pre-surgically with single-agent bevacizumab and were thereafter restaged (study NCT0011321729) (FIG. 26). In Cohort 2, levels of biologically active VEGF were higher in patients with progressing disease than in those with stable or regressing disease (FIG. 27A), but there was no significant difference in levels of bevacizumab-sensitive VEGF between the two patient groups (FIG. 2713), On the other hand, baseline ΔVEGF values were significantly higher in patients with progressing disease than in those with stable or regressing disease (FIG. 27C). Collectively, these findings indicate that the baseline ΔVEGF value can be consistently more informative for assessing bevacizumab treatment benefit than the total level of biologically active VEGF, and that the baseline ΔVEGF value can act as a surrogate for the level of sEV-VEGF.

TABLE 2

Clinicopathologic characteristics and treatment
regimen of patients in Cohort 1

| Pa-tient | Age at diagnosis | Primary site | Disease stage | Pathology | Treatment regimen [†] |
|---|---|---|---|---|---|
| 1 | 80 | Ovary | IIIC | serous, moderately diff.* | Carboplatin + Paclitaxel + Bevacizumab |
| 2 | 74 | Ovary | IIIB | serous, poorly diff. | Carboplatin + Paclitaxel + Bevacizumab |
| 3 | 48 | Ovary | IIC | serous, poorly diff. | Carboplatin + Paclitaxel + Bevacizumab |
| 4 | 34 | Ovary | IV | serous/ endometrioid/ mucinous, poorly diff. | Carboplatin + Paclitaxel + Bevacizumab |
| 5 | 75 | Ovary | IIIC | serous, poorly diff. | Cisplatin + Paclitaxel + Bevacizumab |
| 6 | 59 | Ovary | IIIC | serous, poorly diff. | Carboplatin + Paclitaxel + Bevacizumab |
| 7 | 59 | Ovary | IIIC | serous, poorly diff. | Cisplatin + Paclitaxel + Bevacizumab |
| 8 | 60 | Ovary | IIIC | serous, poorly diff. | Carboplatin + Paclitaxel + Bevacizumab |
| 9 | 33 | Ovary | IV | serous, well-diff. | Carboplatin + Paclitaxel + Bevacizumab |

TABLE 2-continued

Clinicopathologic characteristics and treatment
regimen of patients in Cohort 1

| Pa-tient | Age at diagnosis | Primary site | Disease stage | Pathology | Treatment regimen [†] |
|---|---|---|---|---|---|
| 10 | 49 | Fallopian tube | IIIC | endometrioid/ clear cell, moderately diff. | Cisplatin + Paclitaxel + inhibitor + Bevacizumab |
| 11 | 58 | Ovary | IIIC | clear cell, poorly diff. | Carboplatin + Paclitaxel + PARP inhibitor + Bevacizumab |
| 12 | 49 | Ovary | IIIC | serous, poorly diff. | Carboplatin + Paclitaxel + PARP inhibitor + Bevacizumab |

*diff. (differentiated)
[†] All patients underwent debulking surgery, and then received bevacizumab intravenously (i.v.) (15 mg/kg) in combination with chemotherapy either from cycles 2 to 6 (Patients 1, 2, 4, 5, 6, 7, 10, 11), cycles 2 to 5 (Patients 3, 12) or cycles 3 to 6 (Patients 8, 9). For Patients 10, 11 and 12, the regimen also included the oral PARP inhibitor ABT-888. Following cycle 6, all patients with the exception of Patients 1, 9 and 12 continued to receive bevacizumab as maintenance treatment. Pre-treatment serum was collected at the time of debulking surgery. The interval between debulking surgery and cycle 1 ranged from 20 to 56 days, where the median was 32 days.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Anderson et al., VEGF internalization is not required for VEGFR-2 phosphorylation in bioengineered surfaces with covalently linked VEGF. Integr. Biol. (Camb) 3, 887-896 (2011).

Cao et al., Forty-year journey of angiogenesis translational research. Sci. Transl. Med. 3, 114rv3 (2011).

Cao, VEGF-targeted cancer therapeutics-paradoxical effects in endocrine organs. Nat. Rev. Endocrinol. 10, 530-539 (2014).

Chen et al., Exosomal PD-L1 contributes to immunosuppression and is associated with anti-PD-1 response. Nature 560, 382-386 (2018).

Chevillet et al., Quantitative and stoichiometric analysis of the microRNA content of exosomes. Proc. Natl. Acad. Sci. USA 111, 14888-14893 (2014).

Christianson et al., Cancer cell exosomes depend on cell-surface heparan sulfate proteoglycans for their internalization and functional activity. Proc. Natl. Acad. Sci. USA 110, 17380-17385 (2013).

Dang et al, Hypoxia-inducible factor-1 alpha promotes non-hypoxia-mediated proliferation in colon cancer cells and xenografts. Cancer Res. 66, 1684-1693 (2006).

Eppler et al., A target-mediated model to describe the pharmacokinetics and hemodynamic effects of recombinant human vascular endothelial growth factor in humans. Clin. Pharmacol. Ther. 72, 20-32 (2002).

Fang et al., Tumor-derived exosomal milk-1247-3p induces cancer-associated fibroblast activation to foster lung metastasis of liver cancer. Nat. Commun, 9, 191 (2018).

Feng et al., A class of extracellular vesicles from breast cancer cells activates VEGF receptors and tumour angiogenesis. Nat. Commun. 8, 14450 (2017).

Ferrara et al., The biology of VEGF and its receptors. Nat. Med. 9, 669-676 (2003).

Ferrara et al., Discovery and development of bevacizumab, an anti-VEGF antibody for treating cancer. Nat. Rev. Drug Discov. 3, 391-400 (2004).

Ferrara, Binding to the extracellular matrix and proteolytic processing: two key mechanisms regulating vascular endothelial growth factor action. Mol. Biol. Cell. 21, 687-690 (2010).

Frentzas et al., Vessel co-option mediates resistance to anti-angiogenic therapy in liver metastases. Nat. Med, 22, 1294-1302 (2016).

Manahan & Weinberg, Hallmarks of cancer: the next generation. Cell 144, 646-674 (2011).

Hegde et al., Predictive impact of circulating vascular endothelial growth factor in four phase III trials evaluating bevacizumab. Clin. Cancer Res. 19, 929-937 (2013).

Hicklin & Ellis, Role of the vascular endothelial growth factor pathway in tumor growth and angiogenesis. J. Clin. Oncol. 23, 1011-1027 (2005).

Hsu et al., Hypoxic lung cancer-secreted exosomal miR-23a increased angiogenesis and vascular permeability by targeting prolyl hydroxylase and tight junction protein ZO-1. Oncogene 36, 4929-4942 (2017).

Incio et al., Obesity promotes resistance to anti-VEGF therapy in breast cancer by up-regulating IL-6 and potentially FGF-2. Sci. Transl. Med. 10, eaag0945 (2018).

Iwai et al., Continuous administration of bevacizumab plus capecitabine, even after acquired resistance to bevacizumab, restored anti-angiogenic and antitumor effect in a human colorectal cancer xenograft model. Oncol. Rep. 36, 626-632 (2016).

Iwamoto et al., Cancer lipid metabolism confers antiangiogenic drug resistance. Cell Metab. 28, 104-117 (2018).

Jonasch et al., Phase II presurgical feasibility study of bevacizumab in untreated patients with metastatic renal cell carcinoma. J. Clin. Oncol. 27, 4076-4081 (2009).

Kanada et al., Differential fates of biomolecules delivered to target cells via extracellular vesicles. Proc. Natl. Acad. Sci. USA 112, E1433-1442 (2015).

Ko et al., Inhibition of ovarian cancer growth by a tumor-targeting peptide that binds eukaryotic translation initiation factor 4E. Clin. Cancer Res. 15, 4336-4347 (2009).

Kowal et al., Proteomic comparison defines novel markers to characterize heterogeneous populations of extracellular vesicle subtypes. Proc. Natl. Acad. Sci. USA 113, E968-977 (2016).

Lambrechts et al., Markers of response for the antiangiogenic agent bevacizumab. J. Clin. Oncol. 31, 1219-1230 (2013).

La Venuta et al., The startling properties of fibroblast growth factor 2: How to exit mammalian cells without a signal peptide at hand. J. Biol. Chem. 290, 27015-27020 (2015).

Lidholt et at, A single mutation affects both N-acetylglucosaminyltransferase and glucuronosyltransferase activities in a Chinese hamster ovary cell mutant defective in heparan sulfate biosynthesis. Proc. Natl. Acad. Sci. USA 89, 2267-2271 (1992).

Miles et al., Bevacizumab plus paclitaxel versus placebo plus paclitaxel as first-line therapy for HER2-negative metastatic breast cancer (MERiDiAN): A double-blind placebo-controlled randomised phase III trial with prospective biomarker evaluation. Eur. J. Cancer 70, 146-155 (2017).

Mok et al., A correlative biomarker analysis of the combination of bevacizumab and carboplatin-based chemotherapy for advanced nonsquamous non-small-cell lung cancer: results of the phase IF randomized ABIGAIL study (BO21015). J. Thorac. Oncol. 9, 848-855 (2014).

Muller et al, VEGF and the Fab fragment of a humanized neutralizing antibody: crystal structure of the complex at 2.4 Å resolution and mutational analysis of the interface. Structure 6, 1153-1167 (1998).

Muller et al., Tumor-derived exosomes regulate expression of immune function-related genes in human T cell subsets. Sci. Rep. 6, 20254 (2016).

Nagy et al., Pathogenesis of ascites tumor growth: vascular permeability factor, vascular hyperpermeability, and ascites fluid accumulation. Cancer Res. 55, 360-368 (1995).

Paggetti et al., Exosomes released by chronic lymphocytic leukemia cells induce the transition of stromal cells into cancer-associated fibroblasts. Blood 126, 1106-1117 (2015).

Pötgens et at, Covalent dimerization of vascular permeability factor/vascular endothelial growth factor is essential for its biological activity. Evidence from Cys to Ser mutations. J. Biol. Chem. 269, 32879-32885 (1994).

Rapraeger et al., Requirement of heparan sulfate for bFGF-mediated fibroblast growth and myoblast differentiation. Science 252, 1705-1708 (1991).

Schröder et al., Spectrophotometric determination of iodixanol in subcellular fractions of mammalian cells. Anal. Biochem, 244, 174-176 (1997).

Segura et al., CD8+ dendritic cells use LEA-1 to capture MHC-peptide complexes from exosomes in vivo. J. Immunol. 179, 1489-1496 (2007).

Shojaei et al., Tumor refractoriness to anti-VEGF treatment is mediated by CD11b+Gr1+ myeloid cells. Nat. Biotechnol. 25, 911-920 (2007).

Skog et at, Glioblastoma microvesicles transport RNA and proteins that promote tumour growth and provide diagnostic biomarkers. Nat. Cell Biol. 10, 1470-1476 (2008).

Spillmann et al., Defining the interleukin-8-binding domain of heparan sulfate. J. Biol. Chem. 273, 15487-15493 (1998).

Tang et al., Soluble E-cadherin promotes tumor angiogenesis and localizes to exosome surface. Nat. Commun. 9, 2270 (2018).

Twine, FDA cancels approval for bevacizumab in advanced breast cancer. BMJ 343, d7684 (2011).

Taverna et al., Shedding of membrane vesicles mediates fibroblast growth factor-2 release from cells. J. Biol. Chem, 278, 51911-51919 (2003).

Théry et al., Minimal information for studies of extracellular vesicles 2018 (MISEV2018): a position statement of the International Society for Extracellular Vesicles and update of the MISEV2014 guidelines. J. Extracell. Vesicles 7, 1535750 (2018).

Treps et al., Glioblastoma stem-like cells secrete the pro-angiogenic VEGF-A factor in extracellular vesicles. J. Extracell. Vesicles 6, 1359479 (2017).

Tsujioka et al., A possible clinical adaptation of CRM197 in combination with conventional chemotherapeutic agents for ovarian cancer. Anticancer Res. 31, 2461-2465 (2011).

Wang et al., Cell surface heparan sulfate participates in CXCL1-induced signaling. Biochemistry 42, 1071-1077 (2003).

Wijelath et al., Multiple mechanisms for exogenous heparin modulation of vascular endothelial growth factor activity. J. Cell. Biochem. 111, 461-468 (2010).

Van Cutsem et al., Bevacizumab in combination with che-motherapy as first-line therapy in advanced gastric cancer: a biomarker evaluation from the AVAGAST randomized phase III trial. J. Clin. Oncol. 30, 2119-2127 (2012).

Xu et al., Extracellular vesicles in cancer—implications for future improvements in cancer care. Nat. Rev. Clin. Oncol. 15, 617-638 (2018).

Zhao et al., Hypoxic glioblastoma release exosomal VEGF-A induce the permeability of blood-brain barrier. Biochem. Biophys. Res. Commun. 502, 324-331 (2018).

Zhou et al., Cancer-secreted miR-105 destroys vascular endothelial barriers to promote metastasis. Cancer Cell 25, 501-515 (2014).

What is claimed is:

1. An in vitro method for measuring a level of bevaci-zumab-insensitive vascular endothelial growth factor-A (VEGF-A) in a biological fluid obtained from a cancer patient, the method comprising:

(a) determining an amount of biologically active VEGF-A that is present in the biological fluid by
(i) incubating the biological fluid with a VEGF ligand trap that binds to VEGF-A, and
(ii) detecting the amount of VEGF-A that is bound to the VEGF ligand trap by contacting the bound VEGF-A with a polyclonal VEGF-A antibody;

(b) determining an amount of bevacizumab-sensitive VEGF-A that is present in the biological fluid by (i) incubating the biological fluid with bevacizumab, and
(ii) detecting the amount of VEGF-A that is bound to the bevacizumab by contacting the bound VEGF-A with a polyclonal VEGF-A antibody; and (c) calculating a $\Delta$VEGF value by subtracting the amount of bevacizumab-sensitive VEGF-A from the amount of biologically active VEGF-A, wherein the $\Delta$VEGF value represents the level of bevacizumab-insensitive VEGF-A in the biological fluid, wherein the biological fluid is plasma, serum, ascitic fluid, pleural fluid, peritoneal fluid, or urine.

2. The method of claim 1, wherein the VEGF ligand trap is VEGFR1/R2-Fc.

3. A method of treating a patient having a cancer, the method comprising:

(a) determining a level of bevacizumab-insensitive VEGF-A in a biological fluid obtained from the patient, wherein the level of bevacizumab-insensitive VEGF-A in the biological fluid is measured using the method of claim 1, (b) comparing the level of bevacizumab-insensitive VEGF-A in the biological fluid to a reference level that is a level in a biological fluid of a healthy patient, wherein the biological fluid of the healthy patient corresponds to the biological fluid of the cancer patient, and (c) administering to the patient a therapeutically effective amount of a VEGFR tyrosine kinase inhibitor, a VEGFR neutralizing antibody, or a VEGF ligand trap when the level of bevacizumab-insensitive VEGF-A is elevated relative to the reference level, or administering to the patient a therapeutically effective amount of bevacizumab when the level of bevacizumab-insensitive VEGF-A is not elevated relative to the reference level.

* * * * *